US 8,065,091 B2

(12) United States Patent
Rigoutsos et al.

(10) Patent No.: US 8,065,091 B2
(45) Date of Patent: Nov. 22, 2011

(54) TECHNIQUES FOR LINKING NON-CODING AND GENE-CODING DEOXYRIBONUCLEIC ACID SEQUENCES AND APPLICATIONS THEREOF

(75) Inventors: Isidore Rigoutsos, Astoria, NY (US); Tien Huynh, Yorktown Heights, NY (US); Aristotelis Tsirigos, Astoria, NY (US); Alice Carolyn McHardy, New York, NY (US); Kevin Charles Miranda, McDowall (AU)

(73) Assignee: International Business Machines Corporation, Armonk, NY (US)

( * ) Notice: Subject to any disclaimer, the term of this patent is extended or adjusted under 35 U.S.C. 154(b) by 146 days.

(21) Appl. No.: 11/928,611

(22) Filed: Oct. 30, 2007

(65) Prior Publication Data

US 2008/0052008 A1    Feb. 28, 2008

Related U.S. Application Data

(62) Division of application No. 11/367,512, filed on Mar. 3, 2006.

(51) Int. Cl.
*G01N 33/48* (2006.01)
(52) U.S. Cl. .................. 702/19; 702/20; 703/11; 435/6
(58) Field of Classification Search ........................ None
See application file for complete search history.

(56) References Cited

U.S. PATENT DOCUMENTS

| | | | |
|---|---|---|---|
| 7,186,513 B2 * | 3/2007 | Berka et al. ..................... | 435/6 |
| 7,611,838 B2 * | 11/2009 | Harbison et al. ................. | 435/6 |
| 2004/0241188 A1 | 12/2004 | Collins | |
| 2005/0032056 A1 * | 2/2005 | Freeling et al. .................. | 435/6 |
| 2005/0124010 A1 * | 6/2005 | Short et al. .................. | 435/7.23 |
| 2005/0143928 A1 | 6/2005 | Moser et al. | |
| 2005/0197315 A1 | 9/2005 | Taira et al. | |
| 2005/0244879 A1 | 11/2005 | Schumm et al. | |

FOREIGN PATENT DOCUMENTS

WO    WO 03/012052    2/2003

OTHER PUBLICATIONS

U.S. Appl. No. 11/351,821, filed Feb. 10, 2006, Huynh et al.
I. Rigoutsos et al., "Combinatorial Pattern Discovery in Biological Sequences: The TEIRESIAS Algorithm," Bioinformatics, vol. 14, No. 1, pp. 55-67, 1998.
A. Stabenau et al., "The Ensembl Core Software Libraries," Genome Research, vol. 14, pp. 929-933, 2004.
S.F. Altschul et al., "Basic Local Alignment Search Tool," J Mol Biol., vol. 215, pp. 403-410, 1990.
G. Bejerano et al., "Ultraconserved Elements in the Human Genome," Science Magazine, vol. 304, pp. 1321-1325, May 2004.
M. Ashburner et al., "Gene Ontology: Tool for the Unification of Biology, The Gene Ontology Consortium," Nature Genetics, vol. 25, pp. 25-29, May 2000.
I.L. Hofacker et al., "Fast Folding and Comparison of RNA Secondary Structures," Monatshefte für Chemie (Chemical Monthly), vol. 125, pp. 167-188,1994.
S. Griffiths-Jones et al., "Rfam: An RNA Family Database," Nucleic Acids Research, vol. 31, No. 1, pp. 436-441, 2003.
X. Xie et al., "Systematic Discovery of Regulatory Motifs in Human Promoters and 3' UTRs by Comparison of Several Mammals," Nature Publishing Group, vol. 434, pp. 338-345, Mar. 2005.
S. Iwashita et al., "A Transposable Element-Mediated Gene Divergence that Directly Produced a Novel Type Bovine Bcent Protein Including the Endonuclease Domain of RTE-1," Mol Biol Evol. vol. 20, No. 9, pp. 1556-1563, 2003.
R. Chenna et al., "Multiple Sequence Alignment with the Clustal Series of Programs," Nucleic Acids Research, vol. 31, No. 13, pp. 3497-3500, 2003.
L.P. Lim et al., "Vertebrate MicroRNA Genes," Brevia, Science Magazine, vol. 299, p. 1540, Mar. 2003.
I. Bentwich et al., "Identification of Hundreds of Conserved and Nonconserved Human microRNAs," Nature Genetics, vol. 37, No. 7, pp. 766-770, Jul. 2005.
J.C. Wootton et al., "Statistics of Local Complexity in Amino Acid Sequences and Sequence Databases," Computers and Chemistry, Vol. 17, No. 2, pp. 149-163, 1993.
G. Lev-Maor et al., "The Birth of an Alternatively Spliced Exon: 3' Splice-Site Selection in *Alu* Exons," Science Magazine, vol. 300, pp. 1288-1291, May 2003.
N. Jiang et al., "Pack-Mule Transposable Elements Mediate Gene Evolution in Plants," Nature Publishing Group, vol. 431, 569-573, Sep. 2004.
R.A. Jorgensen, "Restructuring the Genome in Response to Adaptive Challenge: McClintock'Bold Conjecture Revisited," Cold Spring harbor Symposia on Quantitative Biology, vol. LXIX, pp. 349-354, 2004.

* cited by examiner

*Primary Examiner* — Carolyn L. Smith
(74) *Attorney, Agent, or Firm* — Ryan, Mason & Lewis, LLP

(57) ABSTRACT

Techniques for linking non-coding and gene coding regions of a genome are provided. In one aspect, a method of determining associations between non-coding sequences and gene coding sequences in a genome of an organism comprises the following steps. At least one conserved region is identified from one or more non-coding sequences. Additional instances of the conserved region are located in the untranslated or amino acid coding regions of one or more genes in the organism under consideration, and the conserved region is associated with the one or more biological processes in which these one or more genes participate.

16 Claims, 23 Drawing Sheets

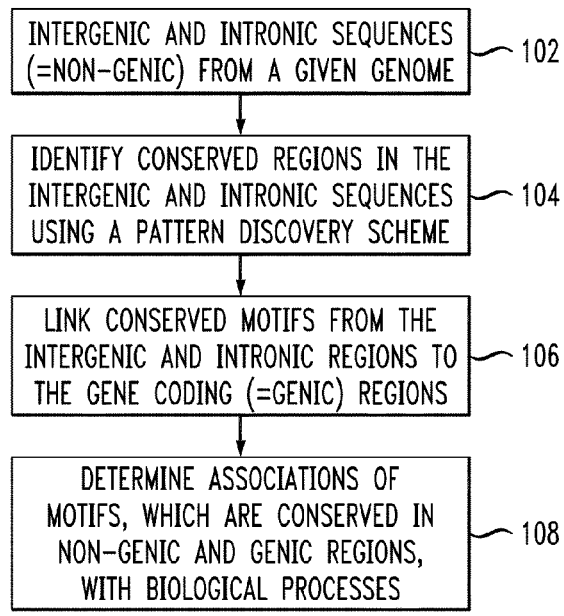
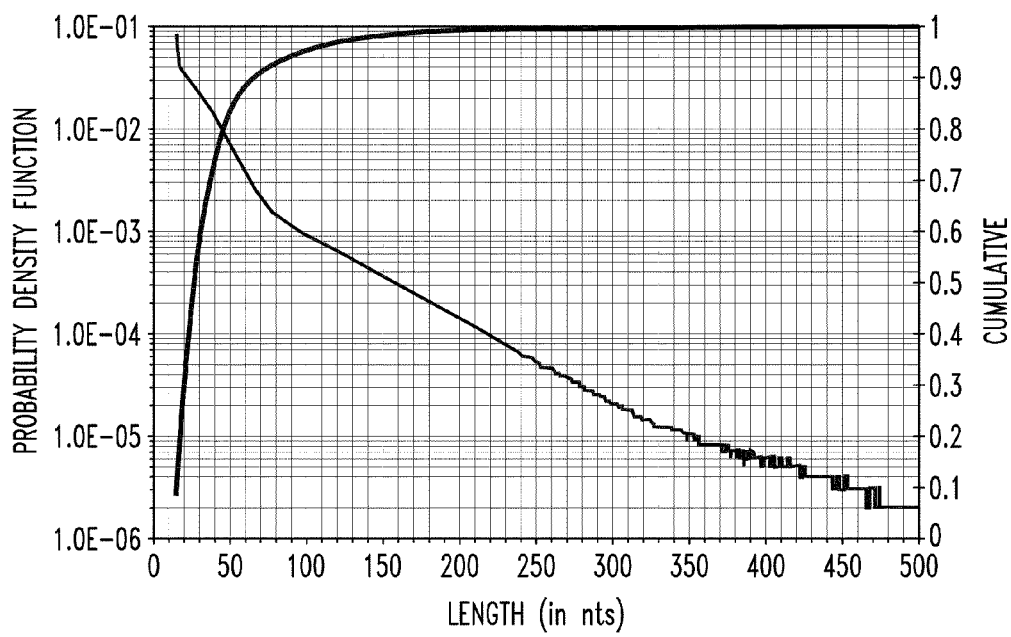
NOTE: THE PROBABILTY DENSITY AND CUMULATIVE FUNCTIONS FOR THE LENGTHS THE ENTIRE COLLECTION OF BLOCKS, $P_{init}$, THAT THE PATTERN DISCOVERY STEP IDENTIFIED IN THE HUMAN INTERGENIC AND INTRONIC REGIONS.

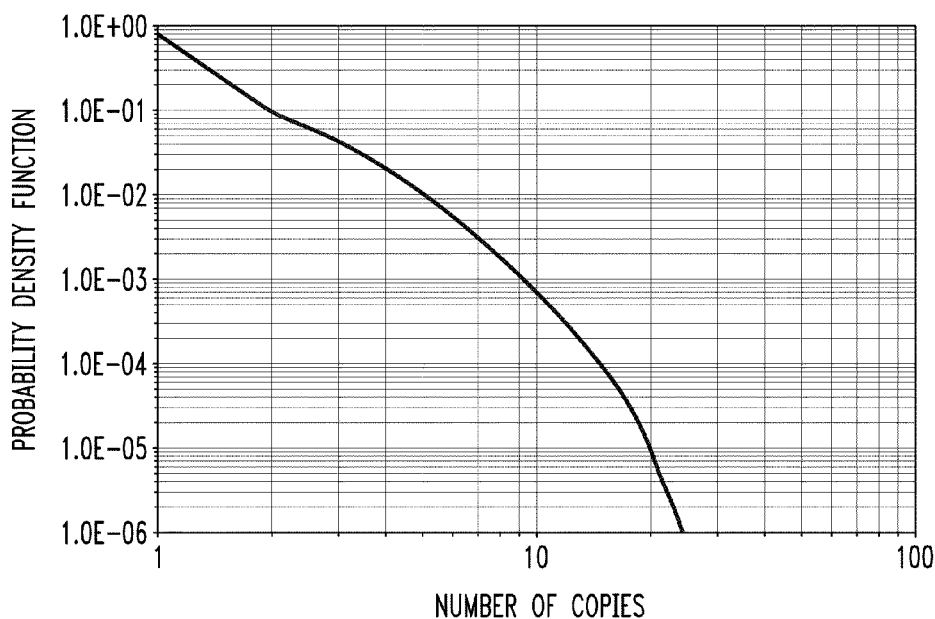

FIG. 3

NOTE: THE PROBABILITY DENSITY FUNCTION FOR THE NUMBER OF INTERGENIC/INTRONIC COPIES OF FIXED-SIZE 16-mers THAT ARE DISCOVERED IN A RANDOMLY-SHUFFLED VERSION OF THE INPUT SET.

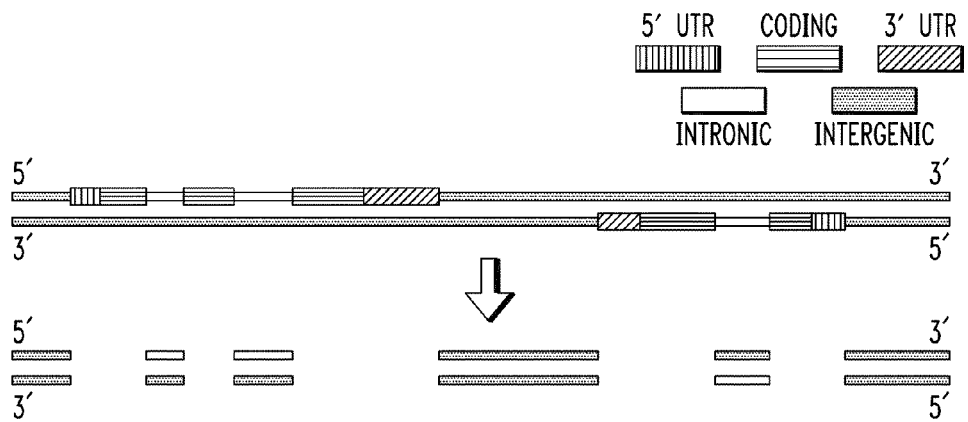

FIG. 4

NOTE: PREPROCESSING OF THE INTERGENIC/INTRONIC SEQUENCES PRIOR TO CARRYING OUT PATTERN DISCOVERY. ALL SEQUENCE SEGMENTS THAT CORRESPOND TO THE UNTRANSLATED AND CODING REGIONS OF KNOWN GENES OR THAT ARE THE REVERSE COMPLEMENT OF THE UNTRANSLATED AND CODING REGIONS OF KNOWN GENES ARE REMOVED. TOP: GENOMIC INPUT BEFORE THE PREPROCESSING. BOTTOM: INPUT ON WHICH PATTERN DISCOVERY WILL BE RUN.

FIG. 5

| | | |
|---:|:---|:---|
| 10 | TCCCATACCACGGGGATT | (SEQ ID NO: 2) |
| 9 | TCCCATACCACGGGGATTA | (SEQ ID NO: 3) |
| 9 | CTCCCATACCACGGGGATT | (SEQ ID NO: 4) |
| 8 | CTCCCATACCACGGGGATTA | (SEQ ID NO: 5) |
| 8 | TCCCATACCACGGGGATTAC | (SEQ ID NO: 6) |
| 7 | GCCTCCCATACCACGGGGATT | (SEQ ID NO: 7) |
| 7 | TCCCATACCACGGGGATTACA | (SEQ ID NO: 8) |
| 5 | GCCTCCCATACCACGGGGATTA | (SEQ ID NO: 9) |
| 4 | GCCTCCCATACCACGGGGATTACA | (SEQ ID NO: 10) |
| 4 | GGCCTCCCATACCACGGGGATTA | (SEQ ID NO: 11) |

NOTE: AN EXAMPLE OF VARIATIONS ON THE SAME THEME. SEVERAL VARIATIONS OF THE SAME CORE PATTERN (SHOWN IN BOX) ARE LISTED IN ORDER OF INCREASING SPECIFICITY AND THUS IN ORDER OF DECREASING NUMBER OF APPEARANCES. THE NUMBER OF APPEARANCES PRECEDES EACH PATTERN.

FIG. 6

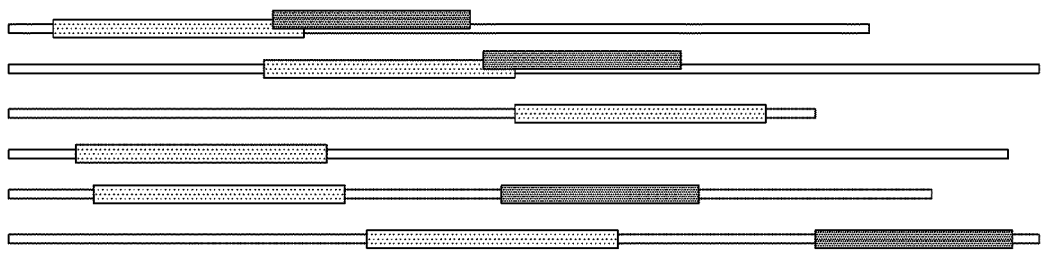

NOTE: DETERMINING LOGICALLY DISTINCT PATTERNS. THE LIGHTER RECTANGLE REPRESENTS ONE BLOCK WITH SIX INSTANCES WHEREAS THE DARKER RECTANGLE REPRESENTS ANOTHER BLOCK WITH FOUR INSTANCES.

NOTE: THE PROBABILITY DENSITY FUNCTION FOR THE LENGTHS OF THE PYKNONS – IT IS SHOWN SEPARATELY FOR EACH OF $P_{5'UTR}$ (LINE MARKED WITH △), $P_{CODING}$ (LINE MARKED WITH (○) AND $P_{3'UTR}$ (LINE MARKED WITH □).

NOTE: NUMBER OF BLOCKS THAT ARE SHARED BY THE THREE SETS WHOSE UNION MAKES UP THE PYKNON COLLECTION.

NOTE: THE CUMULATIVE FUNCTION FOR THE NUMBER OF INTERGENIC AND INTRONIC COPIES OF THE PYKNONS – IT IS SHOWN SEPARATELY FOR EACH OF THE SET $P_{5'UTR}$ (DASHED LINE), $P_{CODING}$ (DASHED-DOT LINE) AND $P_{3'UTR}$ (SOLID LINE).

NOTE: CUMULATIVE FUNCTION THAT SHOWS WHAT PERCENTAGE OF THE AFFECTED 30,675 TRANSCRIPTS CONTAINS N OR MORE PYKNON INSTANCES IN THEM.

FIG. 11A

Note: Combinatorial arrangements of pyknons in 3'UTRs: 3'UTRs are shown for the apoptosis inhibitor *birc4* (shown above the horizontal line) and nine more genes. The sequences below the horizontal line contain some of *birc4*'s pyknons but in different arrangements; they also contain instances of other pyknons that are not present in *birc4*'s 3'UTR. Each of the ten 3'UTRs is a mosaic pyknons. The pyknons in this Figure, have by definition 40 or more instances in the genome's intergenic/intronic regions and *additional* copies in the untranslated and coding regions of these and other genes. The string -(xx)- indicates that xx nucleotides separate the pyknons that surround it. To appreciate the importance of this picture it suffices to keep track of the number of copies and the relative position of the four pyknons TGCACTCCAGCCTGG (SEQ ID NO: 12), TAATCCCAGCACTTTGGGA (SEQ ID NO: 13), GGCTGAGGCAGGAGAAT (SEQ ID NO: 14) and GAGGTTGCAGTGAGCC (SEQ ID NO: 15) in these ten 3'UTRs. Of the nine transcripts shown below the horizontal line: ENST00000338356 encodes a carboxypeptidase M precursor; ENST00000313852 encodes a protein with a bipartite nuclear localization signal; ENST00000361561 encodes a protein with an instance of the RUN domain; ENST00000305513 encodes a protein with a zinc-finger domain; ENST00000259393 encodes a high-affinity copper-uptake protein; ENST00000356694 encodes a protein with an ankyrin repeat; ENST00000295102 encodes a protein phosphatase 2A regulatory subunit that contains a WD-40 repeat; and, ENST00000360166 and ENST00000362058 encode proteins with unknown function.

(SEQ ID NO: 16):

```
>3'UTR OF ENST00000245836[ENSG00000101966_CHR=X_STRAND=FORWARD
-(162)-TTCTGATTTTCAG-(104)-ATACTGATTTAATTC-(208)-ATTTCTTTTAAAGTT-(91)-ACTGACATGGAAAGAT-(243)-TGTATTACTTTTGTAA-(5)-AT
TTTTAGAAAGTATT-(146)-TGGATGAAAAATATT-(591)-CTCACACAACAAACCTAT-(139)-ATTCATTTAAAACATT-(27)-CTTTTGAGATGGAGTCTT-(8)-CCCA
GGCTGGAGTGCA-(8)-ATCTCTGCTCACTGCA-(6)-GCCTTCTGGGTTCAAG-(2)-ATTCTCGTGCCTCAGC-(6)-AGTAGCTGGAATTACAG-(6)-GCCACCATGCC
CGACTA-(39)-TTGGCCAGGCTGGTAT-(2)-AACTCCTGACCTCAAG-(19)-TCCCAAAGTGCTGGGATTACAGGCTTGAGCCACCA-(724)-TTATTTACATTTA
G-(333)-AAATTTGTATTTGAA-(186)-CAGTGGCTCACGCCTGTAATCCCAGCACTTTGGGA-(14)-GATCACGAGGTCAGGAG-(4)-AGACCATCCTGGCTAAC
A-(13)-TCTCTACTAAAAACA-(5)-TTAGCCGGGCGTGGTG-(7)-CTGTAGTCCCAGCTACT-(5)-GGCTGAGGCAGGAGAATGGTGTGAACCCGGAGG-(2)-G
AGCTTGCAGTGAGCC-(13)-TGCACTCCAGCCTGGG-(4)-AGAGCAAGACTCTGTC-(101)-TCTGTGAAAGGAAAT-(69)-ACTCCATCCTAATAC-(137)-CGGT
GGCTCATGCCTGTAATCCCAGCACTTTGGGA-(14)-GATCACCTGAGGTCGGGAGG-(3)-AGACCAGCCTGACCAA-(35)-TTAGCTGGGCGTGGTG-(8)-CTGTA
ATCCCAGCTACT-(5)-GGCTGAGGCAGGAGAAT-(2)-CTTGAACCCAGGAGGC-(1)-GAGGTTGTGGTGAGCG-(13)-TGCACTCCAGCCTGGGCAACAAGAGCA
AAACT-(58)-TTAGCCAGGCGTGGTG-(16)-GCAGCTACTCTGGAGG-(1)-AGAGGCAGGAGGATCACTTGAGCCCATGAATT-(1)-GAGGCAGCAGTGAGCT-(13
)-TGTACTCCAGTCTGGG-(2)-ACAGAGTGAGACCCCA-(50)-TTGAAAAGATTATTCT-(166)-TCATTTTACAGGTGAG-(258)-CCATGGATTCAACCAA-(93)-CTG
TTGTTAAGCAACA-(3)-TAACAACTATTTTACAT-(37)-AGCAATTATTTTTAAA-(12)-ATTGTATTAGGTATA-(33)-CCAGCCTGGACAAAAG-(3)-AAACCCTGTC
TCTACAAAA-(10)-TTAGCTGGGCATGGTG-(9)-TGTAGTCCTGGCTACT-(15)-GGAGGATCGCTTGAGT-(10)-GAGGCTGCATTGAGCT-(13)-TGCATTCCAGCC
TGGG-(10)-AGACCTGTCTCAGAA-(31)-ATTATATGCAAATACT-(23)-CAGTCTCACTGTGTG-(4)-GGATGGAGTGCAATGGCACAATCTTGGCTCAT-(20)-C
AGCTGGGACTACAGG-(11)-GTGCCCAGGCTACCA-(47)-TTGACCAGGCTGGTCT-(2)-AACTCCTGATCTCAGGTGAT-(8)-CTCGGCCTCACAAAGTGCTGGGATTACA
GTGTGAACCAC-(125)-GGCACGGTGGCTCACGCCT-(16)-CCGAGGCTGAGGCAGG-(3)-CTCACCTGAGGTCAGGAGTT-(2)-AGACCAGCCTGGCCAA-(11)-
CCTGTCTGTACAAAA-(7)-ATAGCTGGGCATGGTG-(8)-CTGTAGTCCCAGCTACT-(6)-ACTGAGGCAGGAGAAT-(2)-CTTGAACCTGGGAGGC-(1)-GAGGT
GCAGGGAGCC-(13)-CGCACTCCAGCCTAGG-(1)-GATAGAGTGAGACTCC-(327)-ATGTTTTGAGACAGAG-(56)-GAAAACTAAGAAAATT-(41)-TTATTTTCT
GTGAAT-(10)-CAATAAAATACTATTC-(10)
```

FIG. 11B (SEQ ID NO: 17):
>3'UTR OF ENST00000305513|ENSG00000186532_CHR=17_STRAND=REVERSE
-(66)-GCCAGGTATGGTGGCT-(8)-TAATCCCAGCACTTTGGGA-(15)-ATCACCTGATGTCAGGAGTT-(2)-AGACCAGCCTGGCCAA-(36)-ACTAGCCAGGCGTG
GTG-(8)-CTGTAATCCCAGCTACT-(5)-GGCTGAGGCAGGAGAAT-(2)-CTTGAACCCAGGAGGC-(1)-GAGGTTGCAGTGAGCC-(10)-CACTGCACTCCAGCCC-(
2)-GTGACAGTGTGAGACT-(32)-CGGTGGCTCAAGCCACTTGGGA-(14)-GATCACGAGGTCAGGAG-(4)-AGACCATCCTGGCTAACA-(37)
-TAGTCGGGCCGTGGTGG-(6)-CCTGTATTCACAGCTA-(5)-GAGGTTGAGGCAGGAG-(4)-GGGTGAACCCGGGAGG-(2)-GAGCTTGCAGTGAGCC-(13)-TGCAC
TCCAGCCTGGG-(1)-GACAGAGCCAGACTCC-(11)-AGGCTCACACCTGTAATCC-(1)-CTGTAGTCCCACCTACT-(14)-AGGGTCACCTGAGCCT-(8)-GAGGCTG
GCAATATAGTGAGA-(8)-CTACAAAAAAGTTTT-(11)-AGCATGGTGGCACATG-(1)-CTGTAGTCCCACCTACT-(14)-AGGGTCACCTGAGCCT-(8)-GAGGCTG
CAGTGAGCC-(13)-TGCACTCCAGCCTGGG-(4)-AGAGTAAGACCCTGTC-(547)-TTTTATTGAGCAGTTT-(121)-

(SEQ ID NO: 18):
>3'UTR OF ENST00000338356|ENSG00000135678_CHR=12_STRAND=REVERSE
-(312)-AAAGAAGATCATTTG-(83)-AGCAGTGGCTCACACCT-(2)-TAATCCCAGCACTTTGGGA-(5)-AGGTGGGCGGATCACCC-(16)-AAACCAGCCTGACCA
ACATGGTGAAACCCTGTCTCTACTAAAAT-(1)-TTAGCGGGGTGGTG-(4)-GCACCTGTAATCGCAG-(8)-GAGGCTGAGACAGGAG-(5)-CTTGAACCCTAGAG
GC-(1)-GAGTTGCAGTGAGCC-(9)-CCATTGTACTCCAGCT-(10)-AGTAAGACTCTGTCTC-(525)-TGGGAGTCATCCTTGA-(56)-GGCCAGCTATGGTGGC-(9)-
TAATCCCAGCACTTTGGGA-(21)-TGAAGGTCAGGAGGTCAAGACCAGCCTGGCCAA-(40)-TAGTCGGGCGTGGTGG-(7)-CTGTAATCCCAGCTACT-(5)-GGCT
GAGGCAGGAGAAT-(2)-CTTGAACCCTAGGAGGC-(1)-GAGGTTGCAGTGAGGC-(13)-GAGCTCTTTGAGGCCA-(46)-CCTAGCACATAGTAGG-(3)-TGAATGAATGAA
TATTGATG-(279)-CAGCTCCACTAGGAAG-(18)-CCATTCAATTCCATTT-(132)-GAGCTCTTTGAGGCCA-(46)-CCTAGCACATAGTAGG-(3)-AGCATTAGGCCATTT
-(646)-AAATGGTATTTAGAAA-(14)-CGGTGGCTCATGCCTGTAATCCCAGCACTTTGGGA-(3)-TGAGGCAGGCGGATCACT-(16)-AGACCAGCTGGCCAA-(4
0)-TTAGCCGGGCGTGGTGG-(7)-CTGTAATCCCAGCTACT-(4)-AGGCTGAGGCAGGAGAAAA-(3)-CCTGAACCCAGAAGGC-(1)-GAGGTTGCAGTGAGCC-(15)-
CACTGCACTCCAGCCG-(15)-CCTCTGTCTCAAAAAAA-(65)-TTTCTTTATCTGTAAA-(419)-GTTTAGAAAGTAAAAA-(458)-CCCAGGTTGGAGTGCA-(13)-GG
CTCACTGCAACCTC-(1)-GCCTCCCGGTTCAAG-(5)-CTCCTGTCTCAGCCTC-(2)-GAGTACCTGGGACTAC-(16)-GCCCGGCTAATTTTTGTATTTGTAGTAG
AGA-(13)-TGTTAGCCAGGATGGTCT-(4)-CTCCTGACCTCATGATC-(20)-TCCCAAAGTGCTGGGATTACAGGCGTGAGCCCCCG-(151)-

(SEQ ID NO: 19):
>3'UTR OF ENST00000360166|ENSG00000197291_CHR=17_STRAND=REVERSE
-(62)-CCTGTTGTGGGAGGG-(794)-CGGTGGCTCATGCCTG-(1)-CATCCCAGCACTTTGGGA-(17)-AACCTGAGGTCAGGAGTT-(13)-AACAACATGGTGAAA
C-(42)-TGCCTGCCTGTAATCC-(10)-GAGGCTGAGGCAGGAGAAAA-(3)-CTTGAACCCGAAAGGC-(1)-GAGGTTGCAGTGCC-(10)-CACTGCAACTCCAGCCT-(3
)-CAACAAGAGTGAAACT-(111)-TATTGAACACTTACTA-(148)-GGCAGAGCCAGGATTT-(244)-TGTTTTTAAAAGAA-(386)-TTTACAGACAAGGAAA-(23)-
GGCCAGGCATGTGGCT-(9)-TAATCCCAGCAGTTTGGGAGGCTGAGGTGGGAGGAG-(23)-AGACCAGCCTAGGCCAA-(11)-CCCATCTCTACAAAA-(1)-TTAT
CTGGGCCTGGTG-(8)-CTGTAGTCCCAGCTACT-(2)-AGAGGCTGAGGCAGGAGGTTGAGGCTGCAGTGAGCC-(13)-TGTACTCCAGCC
TGGG-(3)-CAAAGCAAAACCCTGT-(27)-CGGTGGCTCACACCTGTAAT CCCAACACTTTGGGA-(15)-ATCACCTGAGGTCAGGAGTT-(2)-AGACCAGCTGGCC
CAA-(14)-CCTCTACTGAAAATACAAAA-(9)-GCATTGTGGCACATGC-(12)-ATCACCTGAGGTCAGGAGT-(1)-AGACCAGCCTGGCCAA-(36)-TTAGCTGGGC
GTGGTG-(8)-CTGTAGTCCCAGCTACT-(5)-GGCTGAGGCAGGAGAAT-(2)-CTTGAACCTGGGAGGT-(1)-GAGGTTGCAGTAAGCC-(13)-TGCACTCCAGCCTG
GG-(6)-

FIG. 11C (SEQ ID NO: 20):

>3'UTR OF ENST00000313852|ENSG00000180488 CHR=1 STRAND=FORWARD
-(140)-ACTGTACTGTATTTAT-(86)-ATATTTACAGAAATA-(201)-TTATTCATTTGTTTAA-(129)-CAGTGGCTCATGCCTG-(14)-GCTGAGGCAGGAGGACAGT
TTGAGGCCAGGAG-(4)-AGACTAGCCTGGACAA-(16)-TCTCTACAAAAACATAAAATTAGCTGG-(45)-AAAAATAGGCTGGGTGTGGTGGTTCATGCC
TGTAATCCTAGCACTTTGGGA-(13)-GGATCACCTGAGGTCAGGT-(16)-CCCAATATGGTGAAAC-(26)-TAGCCAGGTGTGGTGG-(7)-CTGTAGTCCCAGCTAC
T-(3)-GAGGCTGACACAGGAG-(5)-CTTGAACCCAGGAAGT-(1)-GAGGCTGCAGTGAGCC-(13)-TGCACTCCAGCCTGGG-(6)-AGTGAGACTCTGTC-(36)-G
TGTGGTGGCATGTGT-(1)-TGTGGTCCCAGCTACT-(31)-CCAGAAGGTCAAGGCT-(4)-TGAGCTGTGATTGCAT-(3)-TGCACTCCAGCCTGGG-(4)-AGCAAGAC
CCTATCTC-(51)-AATTTACAATTTACAA-(60)-CCTGTAATCCCAGCTACT-(1)-TGTGGTCCCAGCTACT-(31)-CCAGAAGGCTCTCGCT-(6)-CCCAGGCTGGAG
TGCA-(15)-TAGCTCACTGCAGTCT-(45)-AAATGCATTTTAAAA-(27)-TTTCTGATTAATAAAT-(55)-TGTATGTGCCACATTT-(276)-CACACACACATGTGTG-(5
9)-CAGTGGCTCACGCCTGTAATCCCAGCACTTTGGGA-(17)-AACCTGAGGTCAGGAGTT-(2)-AGACCAGCCTGACCAA-(36)-TTAGCCAGGCATGGTG-(8)-C
TGTAATCCCAGCTACT-(5)-GGCTGAGGCAGGAGAAT-(2)-CTTGAACCCGGGAGGC-(1)-GAGGTTGCAGTTAGCC-(13)-TGCACTCCAGCCTGGGCAACAAG
AGTAAAACT-(7)-

(SEQ ID NO: 21):

>3'UTR OF ENST00000259393|ENSG00000136868 CHR=9 STRAND=FORWARD
-(128)-CACACACACACACCCCTG-(50)-AATTGTTTTTCTAAT-(135)-CTTTTGAATTTTTAA-(153)-CAGTGGCCCATGCCTGTAATCCCAGCACTTTGGG-(16)-
ATCACCTGAGGACAGGAGTT-(2)-AGACCAGTCTGGCCAA-(37)-TAGCCGGGCATGGTGG-(7)-CTGTAGTCCCAGCTACT-(5)-GGCTGAGGCAGGAGAAT-(2)-
CTTGAACCTAGGAGGC-(1)-GAGGTTGCAGTGAGCC-(13)-TGCACTCCAGCCTGGG-(1)-GACAAGAGTGAAACTC-(340)-TTTGAATTAATTTTC-(23)-GCCTC
TAAAACTGTGA-(17)-GCATCAGAATCACCTG-(1)-AGGGCTTGTTAAAACA-(227)-ACATTTATTGAGCTCC-(502)-AGGGCAGAGGAAACAA-(424)-CAATGGC
TCATGCCTGTAATCCCAACACTTTGGGAGGCCAAGGTGGGAGGA-(21)-AGACCAGCCTGGACAA-(3)-AGTGAGATCCTATCTC-(16)-TTAGCCAGGCATGGT
G-(7)-CCTATAGTCCTGGCTA-(8)-GCTGAGGCAGGAGGAT-(20)-AGGCTGCAGTAAGCCA-(7)-GCCACTGCACTCAGCC-(10)-AGCAAGACCCTGTCTC-(880)-
TCTGGGCTGGGCACAG-(7)-CACACTTTGGGAGGCC-(14)-ATCACCTGAGGTCAGGAGTT-(2)-AGACCAGCCTGGCCAA-(36)-TTAGCTGGGGCGTGGTG-(8)-C
TGTAATCCCAGCTACT-(5)-GGCTGAGGCAGGAGAAT-(2)-CTTGAACCCAGGAGGC-(1)-GAGGTTGCAGTGAGCC-(13)-TGCACTCCAGCCTGGG-(1)-GACAA
GAGCAAAACTC-(183)-

(SEQ ID NO: 22):

>3'UTR OF ENST00000362058|ENSG00000186543 CHR=1 STRAND=REVERSE
-(776)-TGTCACCCAGCTGGAG-(90)-TGGTTGGAGCAGGAGG-(330)-CAGTGGCTCACGCCTA-(17)-GAAGCCGAGGCGGGTGGATCAC-(16)-AGACCATCCT
GGCTAACA-(9)-CCTATCTCTACAAAAA-(1)-TTAGCTGGGTGTGGTG-(8)-CTGTAGTCCCAGCTACT-(5)-GGCTGAGGCAGGAGAAT-(6)-AACCTCTGCCTCCG
GG-(14)-CCTGCCTCAGCGTCCC-(1)-AGTAGCAGGGACTACA-(2)-CGTGCACCACCACCG-(10)-GTATTTTAGTAGAGA-(15)-TTGGCCAGGCTGGTCT-(
2)-AACTCTTGACCTCAAG-(10)-GCCAAAGTGCTGGGATTATAGGCGTGAGCCACCG-(116)-CTGCCAGGACTGGGTT-(688)-TGGGGACTTGGGGGGAA-(142
)-CCTCTCTGGGCTGCAG-(699)-AGTTTCACTCTTGTTGCCCAGGCTGGAGTGCA-(14)-GCTCACCTCAACCTCCAGGTTCAAG-(2)-ATTCTCCTGC
CTCAGCC-(5)-AGTAGCTGGATTACAG-(12)-ATGCCTGGATTACAG-(22)-AGCTGGTCTCGAACTC-(13)-ATCTGCCCACTCTGCCC
TCCCAAAGTGCTGGATTA-(1)-AGGCATGAGCCACCGC-(21)-GAGACAGAGTCTCACT-(7)-CCCAGGTTGGAGTGCA-(8)-ATCTGAGCTCACTGCA-(6)-GCC
TCTTGGGTTCAAG-(2)-ATTCTCCTGCCTCAGCCAC-(11)-TCCCAAAGTGCTGGGATTA-(6)-TGAGCCACCATGGCACCTG-(90)-GGAAAGGGGTCAGGC-(23)-TTGGCCAGGC
TGGTCT-(10)-ACCTAAGGTGATCCAC-(11)-TCCCAAAGTGCTGGGATTA-(6)-TGAGCCACCATGGCACCTG-(90)-GGAAAGGGGTCAGGC-(23)-TGGAAACTGAG
GCCCAG-(51)-CTCTGCCTCTGGGATT-(213)-GTGGGCACCAGGAG-(107)-CATCTGTGAAATGGGA-(289)-TGCCTGGGTTTGAATC-(37)-TCTGTGCCTTC
ATTTC-(318)-GCTGGGATTCCAGGCA-(61)-TAATCCCAGCACTTTGGGA-(14)-GATCACGAGGTCAGGAG-(4)-AGACCATCCTAGCTAACA-(1)-AGTGAAACC
CTATCTC-(18)-TTAGCTGGGCATGGTG-(9)-TGTAGTCCCAGATACT-(8)-TAAGGCAGAGAAGAATCGCTTCAACCTGGGAGGC-(1)-GAGGTTGCAGTGAGCC-(13
)-TGCACTCCAGCCTGGG-(21)-

*FIG. 11D*

(SEQ ID NO: 23):
>3'UTR OF ENST00000361561|ENSG00000198863_CHR=17_STRAND=FORWARD
-(225)-CGGTGGCTCACACCTGTAATCCCAGCTACT-(5)-GGCTGAGGCAGGAGAATGGCGTGAACCCAGGAGG-(4)-AGACCATTCTGTCTAACA-(33)-AAATTAGTCGGACATG-(11)-CTGTAGTCCCAGCTACT-(5)-GGCTGAGGCAGGAGAATGGCGTGAACCCAGGAGG-(2)-GAGCTTGCAGTGAGCC-(13)-TGCACTCCAGCCTGGG-(1)-GACAGAGTGAGACTCC-(86)-CAGTGGCTCACGCCTG-(9)-CACATTGGGAGGCTGAGG-(7)-ATCACCTGAGGTCAGGAGTT-(2)-AGACCAGCCTGGCCAA-(60)-CTGTAATCCCAGCTACT-(3)-GAGGCTGAGGCGGGAGAA-(3)-CTTGAGCCCGAGAGGT-(12)-AAGCCAAGATCATGCCA-(1)-TGCACTCCAGCCTGGGCAACA
CAGGGAGACTC-(84)-TTTGAGAGGCCTAGGC-(160)-TTTTTCTTGTAGAGGT-(492)-CAAAAATGGGCAAAAT-(344)-

(SEQ ID NO: 24):
>3'UTR OF ENST00000356694|ENSG00000197256_CHR=19_STRAND=REVERSE
-(41)-TTTTTGTTTTTGAGGC-(14)-TCGCCCAGGGTGGAGT-(16)-GGCTCATTGCAACCTC-(1)-GCCTCCCGGGCTTCAAG-(5)-CTGCTGCCTCAGCCTC-(2)-GAG
TAGCTGGGATAACAGGTGTGTGGCCACCATGCCT-(7)-CAGCTATTCTGGAGGCT-(15)-CTTGAACCCAGGAGGT-(1)-GAGGTTGCAGTGAGCC-(18)-CAACAA
GAGCAAAACT-(82)-AAGAGATGACATTTGA-(62)-TGCAAAGGCCCTGAGG-(15)-TAATCCCAGCACTTTGGGA-(15)-ATCACCTGAGGTCAGGAGTT-(2)-AGA
CCAGCCTGGCCAA-(36)-TTAGCTGGGTGTGGTG-(8)-CTGTAATCCCAGATACT-(6)-GCTGAGGCATGAGAAT-(2)-CTTGAACCTGGGAGGC-(6)-TGCAGTGA
GCTGAGAT-(8)-TGCACTCCAGCCTGGG-(1)-TAGCTGGGACTACT-(3)-GAGGCTAAGGCAGGAG-(29)-CTGTGAGCTATGA
TTG-(6)-TATACTCCAGCCTGGC-(6)-GCAAGACCCTGTCTT-(4)-AAAAAAAATCTAGGC-(2)-GGCACGGTGGCTCACGCCT-(1)-TAATCTCAACACTTTG-(18
)-ATCACCTGAGGTCAGGAGTT-(2)-AGACCAGACTGACCAA-(15)-TCTCTACTAAAAACGCAAA-(1)-TTAGCCGGGCGTGGTGG-(7)-CTGTAATCCCAGCTAC
T-(5)-GGCTGAGGCAGGAGAAT-(2)-CTTGAACCCAGGAGGC-(6)-TGCAGTGAGCTGAGAT-(8)-TGCACTCCAGCCTGGGCAACAAGAGTGAAACT-(7)-

(SEQ ID NO: 25):
>3'UTR OF ENST00000295102|ENSG00000143940_CHR=2_STRAND=FORWARD
-(112)-TCCTCTGTCTCTGCCT-(363)-TTGAATTTTGTAAAAT-(182)-CAGTGGCTCACACCTGTAATCCCAGCCCTTTGGGA-(2)-CTGAGGCAGGTGGATT-(1)-C
TTGAGCCCAGGAGTT-(16)-CTCATCTCTACAAAAA-(11)-GTGGTGGCGTGTACCTCTAGTCCCAGCTACCC-(43)-CTAGCGTGCAGTGAGC-(14)-TGCACTCC
AGCCTGGT-(2)-ACAGTGAGGCCCTGTC-(175)-AAAAAAAAATTTTCTG-(54)-ACTGAGCACTTTTAAA-(148)-AAAATGTTACTGAAT-(43)-ATCATGTTATTTT
TCT-(116)-TTGGAAATTATTTTAA-(284)-TTTTGTTGAAAGCAAA-(1695)-ATATTCACTTTTTAAA-(826)-ATACATATTTACATAA-(63)-ATAGAAAACTTTAAAA-
(10)-GGGCACTTTGCTCAC-(5)-TAATCCCAGCACTTTGT-(6)-GAGGTGGCCGATCTCTAGGTACTCAGGAGGAGGCAGGAAAAT-(2)-CTTGAACCTGGGAGGC-(1)-GAGGTTGCAGTG
AGCC-(13)-TGCACTCCAGCCTGGG-(1)-GACAGAGTGAGACTCC-(413)-TGAGAATATTTAAAT-(80)-ATTTTATTTCAAGAT-(130)-TCATTCCAATTTAGT-(
258)-CAAAGGCCGGGCGCGG-(13)-TAATCCCAGCACTTTGGGA-(14)-GATCACGAGGTCAGGAG-(4)-AGACCATCCTGGCTAACA-(34)-ATTAGCCAGGCCT
GGT-(9)-CTGTAGTCCCAGCTACT-(3)-GAGGCTGAGGCAGGAGAACGGCGTGAACCCGGGAGG-(2)-GAGCTTGCAGTGAGCC-(13)-TGCACTCCAGCCTAGG
-(1)-GGCAGAGCCAGACTCC-(5)

*FIG. 11*

| FIG. 11A |
|----------|
| FIG. 11B |
| FIG. 11C |
| FIG. 11D |

FIG. 12A

Note: 5'UTRs for ENSG00000196809 a human gene of unknown function and eight more genes. The shown 5'UTRs are mosaics composed of pyknons. The shown pyknons have 40 or more copies in the genome's intergenic and intronic regions. The string (xx) indicates the number of nucleotides, xx, that separate the surrounding pyknons. To appreciate the importance of the result in this Figure, it suffices to keep track of the number of copies and relative arrangement in each of the shown 9 genes of the four pyknons TCCCAAAGTGCTGGATTA (SEQ ID NO: 26), CCCAGGCTGGAGTGCA (SEQ ID NO: 27), AGTAGCTGGGATTACAG (SEQ ID NO: 28) and AACTCCTGACCTCAGGTGAT (SEQ ID NO: 29). Below the solid line are the 5'UTRs for eight other transcripts: ENST00000314752, a monoamine-sulfating phenol sulfotransferase which is involved in catecholamine/lipid/steroid metabolism; ENST00000287474, a gene whose product has dopamine beta-monooxygenase activity and is involved in catecholamine metabolism; ENST00000344420, that encodes a centromere protein involved in nucleosome assembly, chromosome organization and biogenesis; ENST00000355921 a zinc finger protein involved in transcription regulation; ENST00000358920, that encodes a gene of unknown function; ENST00000357256, a surfeit locus protein; ENST00000355587, a Huntingtin interacting protein; and, ENST00000326880, that encodes a peptide-chain release factor.

(SEQ ID NO: 30):

>5'UTR OF ENST00000358509|ENSG00000196809_CHR=22_STRAND=FORWARD_UPSTREAM_UTR
-(704)-TTTCTTCATTCATTCA-(53)-GACAGTCTCGCTCGT-(2)-CCCAGGCTGGAGTGCA-(8)-ATCTCAGCTCACTGCA-(6)-GCCTTCCAGGTTCAAG-(2)-AGTC
TCCTGCCTCAGCCTC-(3)-AGTAGCTGGGATTACAG-(9)-ACCACGCCTGGCTAATT-(4)-CATTTTAGTAGAGACG-(3)-CTTCACCATGTTGGCCA-(11)-AACTC
CTGACCTCAGGTAAT-(11)-TCCCAAAGTGCTGAGATTA-(5)-GTGAGCTACCGTGCCC-(216)-GGTGGTCAGGGAAGGC-(64)-AGGCAGGAGGAACAGC-(192)-
TTCATTCAACAAATAT-(931)-TTGCCCAGGCTGGAGTT-(10)-AGCTCACTGCAACCTCCACCTCCAGATTCAAGTGATTCT-(17)-AATAGTGGGACTACA-(5)
-ATGTCACCATGCCCAG-(42)-TTGGCCAGGCTGGTCT-(2)-AACTCCTGGCCTCAAA-(1)-ACCTCCGGGTTCAAG-(13)-TCAGCTTCCTGAGTAGCT-(5)-TACAGGCACT
GAGCCACCG-(87)-CCCAGGCTGGAGTGCA-(13)-GGCTCATTGCAACCTC-(1)-AACTCCTGACCTCAGGTGAT-(15)-TCCCAAAGTGCTGGCATTA-(2)-GGCTTGAGC
TGCCAC-(32)-GACAGGGTTTGCCATCT-(1)-TTGGCCAGGCTGGAGTGCA-(13)-AACTCCTGACCTCAGGTGAT-(15)-TCCCAAAGTGCTGGCATTA-(2)-GGCTTGAGC
CACCACG-(351)-GGAGTCTCGCTCTGTC-(6)-GCTGGAGTGCAGTGAC-(1)-TGATCTCGGCTCACTGCAG-(1)-CTCCGCCTTCTGGGTTCA-(4)-ATTCTCCTGC
CTCAGCCTC-(3)-AGTAGCTGGGACTACAG-(7)-CCACCTCGCCTGGCTA-(36)-TGTTAGCCAGGATGGTCT-(4)-CTCGTGACCTCGTGATC-(2)-CCAGCCTCGG
CCTCCC-(20)-TGAGATGGAGTTCGC-(9)-TCAGGCTGGAGTGCAATG-(5)-ATCTCAGCTCACTGCA-(6)-GCCTCCCAGGTTCAAG-(2)-ATTCTCCCACCTCAG
C-(6)-AGTAGCTGGGATTACAG-(45)-GGGGTTCACTATGTTGGCCCAAGCTGGTCTTGAACTCCTGACCTCAGGTGAT-(15)-TCCCAAAGTGCTGGGATTA-(14
5)-TGGAGGTAGGGCCTGG-(49)-TGAATGAAAGAATGAA-(4)-TTTGGGAGGCCAAGGTGGGT-(2)-ATCACCTGAGGTCAGGAGTT-(2)-AGACCAGCCTGGCC
AA-(15)-CCCTCTACTAAAAATACAAAAAATTAGCTGGGCGT-(9)-TGCCTGTAATCACAGC-(7)-GAGGCTGAGGCAGGAGAAT-(19)-GAGGTTGCAGTGAGCC-(
7)-TGCCATTGCACTCCAG-(4)-GGCAACAGAGCGAGACT-(584)-

FIG. 12B (SEQ ID NO: 31):
>5'UTR OF ENST00000314752|ENSG00000132207_CHR=16_STRAND=FORWARD_UPSTREAM_UTR
-(5)-GAGTCTTGCTCTGTTG-(2)-GGAGGCTGGAGTGCAGTGATCTCAGCTCACTGGA-(6)-GCCTCCTGGGTTCAAG-(11)-TCTCAACCTCCCAAGT-(1)-TGCCAC
CACACCTGCC-(11)-TTTTTAGTAGGGATGG-(11)-TTGGGCAGGCTGGTCT-(2)-AACTCCTGACCTCAAG-(19)-TCCCAGAGTGCTGGGATTA-(6)-TGAGCCAC
CATGCCTG-(8)-CCTGTCTCTAAAACA-(190)-CAGAAATTTTCTTTTT-(23)-GAGACAGAGTCTACT-(3)-TCGCTCAGGCTGGAGT-(11)-ATCTCAGCTCACTG
CAACCTCTGCCTCCTGGT-(11)-CTCCTTCCTCAGCCTC-(3)-AGTAGCTGGGATTACAC-(7)-CCACCGCGCCTGGCTA-(38)-TTGGCCAGGCTGGTCT-(2)-AACT
CCTGACCTCAGGTGAT-(12)-AGCCTCCCAAAATGCT-(7)-CAGGCATGAGCCACCG-(239)-CTCAGTTTCTTCATTT-(77)-GGGGTTGCTGCCAGCTG-(262)-

(SEQ ID NO: 32):
>5'UTR OF ENST00000287474|ENSG00000156869_CHR=1_STRAND=REVERSE_UPSTREAM_UTR
-(4)-TGCTGGGATTACAGGCGC-(5)-ACCACGCCCGGCTAAT-(23)-GGGTTTCACTGTGTTG-(3)-AGGATGGTCTCTATCTC-(8)-GTGATATGCCGCCTC-(4)-TC
CCAAAGTGCTGGGATTACAGGCTTGAGCCACCG-(5)-GGCCTATTTATTTATT-(6)-GAGACGGAGTGTTGCT-(7)-CCCAGGCTGGAGTGCA-(13)-GGCTCACT
GCAACCTC-(1)-GCCTCCGGGTTCAAG-(2)-ATTCTCCTGCCTCAGCCTC-(3)-AGTAGCTGGGATTACAG-(12)-ACACCCGGCTAATTTTGTATTTTAGTAGAA
A-(2)-GGGTTTCTCCATGTTG-(6)-CTGGTTTCGAACTCCC-(8)-GTCATCTGCCTGCCTC-(4)-TCCCAAAGTGCTGGGATTACAGGCGTGAGCCACCG-(12)-TCT
GTATTTTAAAAA-(21)-TAAATGATTTGCCCAA-(72)-

(SEQ ID NO: 33):
>5'UTR OF ENST00000344420|ENSG00000115163_CHR=2_STRAND=FORWARD_UPSTREAM_UTR
-(1260)-ACAACACCCAAGTCCT-(47)-GCCTGAGTGCAGTGGC-(142)-TCTTCAAAGAAGAAA-(53)-TTTGAGACAGAGTCTC-(9)-CCCAGGCTGGAGTGCA-(1
6)-GGCTCACTACAACCTC-(1)-GCCTCCCAGGTTCAAA-(2)-ATTCTCCTGCCTCAGCCTC-(3)-AGTAGCTGGGATTACAG-(26)-ATAGAGATGGGGTTTC-(6)-TT
GGCCAGGCTGGTCT-(2)-AACTCCTGACCTCAGGTGAT-(15)-TCCCAAAGTGCTGGGATTA-(11)-CACCACACCCAGCCAT-(8)-ATTATGTTTCTAAAA-(46)-C
AGACTCTGCCTCAAA-(237)-GAGTCTTGCTCTGTTG-(3)-CGCTGGAGTGCAGTGG-(9)-GGCTCACTGCAACCTC-(2)-GCTCCCAGGTTCAAGC-(10)-AGTAGC
TGGGACTACAG-(12)-ACATCCGGCTAATTTT-(12)-ATAGAGACGGGGTTT-(6)-TTGGCCAGGATGGTCT-(4)-CTCCTGACCTCATGATC-(10)-AGCCTCCCAA
AGTGCTGGGG-(4)-AGGCATGAGCCACCACG-(42)-GTCTTGCTCTGTCACC-(14)-CCTCCTGCCTCAGCCTCCCGA-(13)-ACAG
GTATGTACCACC (SEQ ID NO: 34):
>5'UTR OF ENST00000358920|ENSG00000198037_CHR=12_STRAND=FORWARD_UPSTREAM_UTR
-(504)-AGAGTCTTGCTCTGTCGCCCAGGCTGGAGTGCA-(13)-GGCTCACTGCAACCTC-(1)-GCCTCCCAGGTTCAAG-(2)-ATTCTCCTGCCTCAGCCTC-(3)-T
GTAGCTGGGATTACAGGC-(6)-CACCATGCCCGGCTAAT-(4)-TTATTTTAGTAGAGA-(15)-TTGGCCAGGCTGGTCT-(2)-AACTCCTGACCTCAGGTGAT-(15)-
TCCCAAAGTGCTGGGATTACAGGCGTGAGCCACCG-(29)-TGGTCTTGCTGTGTCACCCAGGCTGGAGTGCA-(25)-TCTTGAATTCCTGGGC-(19)-AAGCCTC
CCAAGTAGCT-(7)-CAGGACACATACTACCA-(21)-TTTTGTAGAGACAGG-(4)-TTACTATGTTGCCCAGACTGGTCTTGAACTCC-(41)-ATTACAGGTGTGAGCC
T-(57)-GTTTTTGAGACAGGGT-(12)-CCCAGGCTGGAGTGCA-(13)-GGCTCACTGCAGCCTCAGG-(2)-CCTCCCAAGGCTCAGG-(2)-ATCCTCTGCCTCAGC-(16
)-ACCAAGTAGCTGGGAC-(1)-

FIG. 12

| FIG. 12A |
| FIG. 12B |
| FIG. 12C |

FIG. 12C (SEQ ID NO: 35):

>5'UTR OF ENST00000357256|ENSG00000148297_CHR=9_STRAND=REVERSE_UPSTREAM_UTR
-(66)-GGCTGGAGGGCAGAGG-(128)-CCCAGGCTGGAGTGCA-(7)-GATCTCGGCTCACTGCG-(24)-ATTCTCCTGCCTCAGCCTC-(3)-AGTAGCTGGGATTACA
G-(7)-CCATCACGCCCGGCTA-(37)-TTGGTCAGGCTAGTCT-(2)-AACTCCTGACCTCAGGTGAT-(13)-TCCCAAAGTGCTGGGATTACAGGCGTGAGCCACCG-
(44)-GCAGAGACTGGAGGGA-(63)-

(SEQ ID NO: 36):

>5'UTR OF ENST00000355921|ENSG00000174652_CHR=19_STRAND=REVERSE_UPSTREAM_UTR
-(7)-TCTGTTGCCAGGCTGGAGTGCCTGGAGTCTCGGCTCACTGCAACCTC-(3)-CTCTCAGGTTCAAGCGATTCTCCTGCCTCAGCCTCCTCAGTAGCT
GGGATT-(3)-AGGCATGCACTACCAT-(25)-TAGAGATGGGGTTTCACCAC-(1)-TGCCCAGGCTGGTCT-(2)-AACTCCTGACCTCAAC-(19)-TCCCAAAGTGCT
GGGATTACAGGCGTGAGCCACCG-(2)-CCCGGCCCTGATTTTT-(257)-CTGGATAAAGAGAATG-(295)-GAGTCTTGCTCTGTTGCTCAGGCTGGAGTGCA-(7)-
GATCTCAGCTCATTGC-(7)-GCCCCCCAGGTTCAAG-(5)-TTCCTGCCTCAGCCTC-(3)-AGTAGCTGGGATTACAG-(12)-ACACCTGGCTAATTT-(5)-ATTTAG
TAGAGATGG-(12)-TTGGCCAGGATGGTCT-(4)-CTCTTGACCTCGTGATC-(14)-CTCCAAGTGCTGGGATTACAGGCGTGAGCCATCA-(80)-TTTCCTTATCT
GTAAA-(156)-GAATGACTTTGGGGTA-(41)-TTCTTTCTTTTCCATG-(633)-

(SEQ ID NO: 37):

>5'UTR OF ENST00000355587|ENSG00000140264_CHR=15_STRAND=FORWARD_UPSTREAM_UTR
-(255)-ACATATTTTAAATTCT-(1004)-GAGTCTTGCTCTGTTGCCCAGGCTGGAGTGCA-(8)-GTCTCAGCTCACTGCA-(6)-GCCTCTTGGGGTTCAAG-(6)-TCCTA
CCTCAGCCTCCT-(1)-AGTAGCTGGGATTACAG-(5)-TACCACCACATGTCCAGC-(12)-TTTTACTAGAGATGGGGTTT-(7)-TTGGCCAGGCTGGTCT-(4)-CTCCTGA
CCTCATGATC-(14)-TCCCAAAGTGCTGGGATTACAGGCATGAGCCACCG-(253)-GAATGGGCAAAAGCTG-(125)-GTCTTGCTCTGTCACC-(1)-AGGCTAGAG
TGCAGTG-(7)-TTCAGCTCACTGCAACCT-(2)-GCCTCCCAGGGTTCAAG-(10)-GCCTCCACCTTCCTGAAGCAGCTGGGATTACAGG-(7)-CACCATGCCCGGCTAA
T-(34)-TGTTAGCCAGGATGTGT-(4)-CTCTTGACCTCGTGATC-(14)-TCCCAAAGTGCTGGGATTACAGGGCGTGAGCCACCTG-(379)-CAATGTTTTACAGTTT-(7
0)-CTCAAGGTTACACAGC-(321)-GAGTGTGTGTGAGAGA-(406)-AACCCAGGAGGGTTGAA-(124)-ATCTGACCTTTCTCTC-(214)-TGTGCCAGGCCCAGGG-(3
03)-

(SEQ ID NO: 38):

>5'UTR OF ENST00000326880|ENSG00000120662_CHR=13_STRAND=REVERSE_UPSTREAM_UTR
-(101)-TTGTCGCCCACGCTGG-(13)-ATCTCAGTTCACTGCA-(6)-GCCTCCCAGGTTCAAG-(9)-TGCCTCAGCTTCCCGA-(2)-AGCTAGGACTACAGGT-(10)-ACG
CTCAGCTAATTT-(18)-GATGGGGTTTCCCAT-(1)-TTGGCCAGGCTGGTCT-(2)-AACTCCTGACCTCAGA-(38)-CAGGCGTGAGCCACTG-(8)-ACATTTTGGTAT
GTTT-(282)-TGAACAGGCAACTTACA-(105)-AATATATTTTCTTCA-(312)-TGCTGGAGTGCAATGG-(9)-GGCTCACTGCAACCTC-(1)-GCCTCCTGGGTTCAGG-
(5)-CCCTGCCTCAGACTC-(3)-AGTAGCTGGGATTACAG-(2)-GCCTGCCACCACGCCCGG-(27)-GTGTTTCACTATGTTG-(3)-GGGCTGGTCTCGAACT-(1)-CTG
CCCTCAGTCAGTGATC-(14)-TCCCAAAGTGCTGGGATTA-(2)-GGCCGTGAGCCACTGCT-(46)-TAGATGAAACAAGATT-(24)-TATGCATGTATCTTTA-(7)-TTTTTTTT
AAAGACT-(26)

FIG. 13A

Note: Amino acid-coding regions for ten genes. The shown coding regions are mosaics composed of the 124 instances of 11 pyknons in various arrangements. It is important to remember that the shown pyknons have 40 or more copies in the genome's intergenic and intronic regions. The string (xx) indicates the number of nucleotides, xx, that separate the surrounding pyknons. To appreciate the importance of this picture it suffices to keep track of the number of copies and relative arrangement of the four pyknons AAATGTGAAGAATGTG (SEQ ID NO: 39), TCATACTGGAGAGAAA (SEQ ID NO: 40), ACAAGTGTGAAGAATG (SEQ ID NO: 41) and CATACTGAAGAGAAAC (SEQ ID NO: 42) in each of the shown sequences. All of these genes encode C2H2 type zinc-finger proteins: ENST00000356096 codes for a negative regulator of osteoclast differentiation and is involved in DNA-dependent regulation of transcription; ENST00000357002 encodes a hematopoietic-cell-derived zinc-finger protein that is involved in the negative regulation of transcription from the Pol-II promoter; the products of ENST00000335117 and ENST00000331027 are known to be involved in DNA-dependent transcription regulation.

(SEQ ID NO: 43):

>AMINO-ACID CODING REGION OF ENST00000335117||ENSG00000160321_CHR=19_STRAND=REVERSE
-(166)-AAGGAAAAAAACCTTT-(74)-AGCAGAGCATAAAAGA-(50)-ATTTACAGTTTAAAAA-(259)-AAATGTGAAGAATGTG-(46)-TCATACTGGAGAGAAA-(90)-AAATGTGAAGAATGTG-(46)-TCATACTGGAGAGAAA-(6)-AAATGTGAAGAATGTG-(68)-AAATGTGAAGAATGTG-(46)-TCATACTGGAGAGAAA-(6)-AAAT GTGAAGAATGTG-(68)-AAATGTGAAGAATGTG-(46)-TCATACTGGAGAGAAA-(6)-AAATGTGAAGAATGTG-(130)-TCATACTGGAGAGAAA-(6)-AAATGTGA AGAATGTG-(46)-TCATACTGGAGAGAAA-(66)-

(SEQ ID NO: 44):

>AMINO-ACID CODING REGION OF ENST00000331027||ENSG00000182111_CHR=7_STRAND=FORWARD
-(48)-AAATGTGAAGAATGTG-(83)-AAATGTGAAGAATGTG-(46)-TCATACTGGAGAGAAA-(65)-TCATACTGGAGAGAAA-(90)-AAATGTGAAGAATGTG-(130)-TCATACTGGAGAGAAA-(68)-TCATACTGGAGAGAAA-(6)-AAATGTGAAGAATGTG-(46)-TCATACTGGAGAGAAA-(6)-AAAT GTAAAGAATGTG-(46)-TCATACTGGAGAGAAA-(6)-AAATGTGAAGAATGTG-(80)-

FIG. 13B (SEQ ID NO: 45):

>AMINO-ACID CODING REGION OF ENST00000341265||ENSG00000182141_CHR=13_STRAND=REVERSE
-(204)-AAATGTGAAGAATGTG-(46)-TCATACTGGAGAGAAA-(6)-AAATGTGAAGAATGTG-(236)-AAATGTGAAGAATGTG-(47)-CATACTGAAGAGAAAC-(5)-
AAATGTGAAGAATGTG-(56)-TGTGAAAAATGTGGCA-(191)-AAATGTGAAGAATGTG-(65)-AAATGTGAAGAATGTG-(68)-AAATGTGAAGAATGTG-(46)-TCA
TACTGGAGAGAAA-(36)-

(SEQ ID NO: 46):

>AMINO-ACID CODING REGION OF ENST00000357002||ENSG00000183850_CHR=19_STRAND=FORWARD
-(93)-AATTTATATAGAAATG-(185)-TCTTTCAAAAAGCAA-(34)-TTTACAGTTAAGAAAA-(95)-TGATAAATATTTGAAA-(147)-AAATGTAAAGAATGTG-(152)-
AAATGTGAAGAATGTG-(46)-TCATACTGGAGAGAAA-(4)-ACAAGTGTGAAGAATG-(68)-ACACTGGAGAGAAACC-(4)-AAAT
GTGAAGAATGTG-(46)-TCATACTGGAGAGAAA-(152)-ACAAGTGTGAAGAATG-(4)-ACAAGTGTGAAGAATG-(70)-AAATGTGAAGAATGTG-(48)-ACACTGG
AGAGAAACC-(4)-AAATGTGAAGAATGTG-(46)-TCATACTGGAGAGAAA-(6)-AAATGTGAAGAATGTG-(47)-CATACTGAAGAGAAAC-(8)-TGTGAAAAATGT
GGCA-(43)-TCATACTGGAGAGAAA-(6)-AAATGTGAAGAATGTG-(158)-

(SEQ ID NO: 47):

>AMINO-ACID CODING REGION OF ENST00000330020||ENSG00000184624_CHR=18_STRAND=FORWARD
-(204)-AAATGTGAAGAATGTG-(10)-TAAACAATTCTCAAAA-(20)-TCATACTGGAGAGAAA-(6)-AAATGTGAAGAATGTG-(236)-AAATGTGAAGAATGTG-(47)-
CATACTGAAGAGAAAC-(5)-AAATGTGAAGAATGTG-(31)-TCATACTGAAGAATGTG-(9)-TGTGAAAAATGTGGCA-(197)-AAATGTGAAGAATGTG-(47)-CATA
CTGAAGAGAAAC-(68)-CATACTGAAGAGAAAC-(5)-AAATGTGAAGAATGTG-(46)-TCATACTGGAGAGAAA-(36)-

(SEQ ID NO: 48):

>AMINO-ACID CODING REGION OF ENST00000355326||ENSG00000185037_CHR=7_STRAND=REVERSE
-(21)-CAGCCAGAGCAGGGCA-(232)-AAAGAAACATTTCAAA-(143)-TCATACTGGAGAGAAA-(68)-TCATACTGGAGAGAAA-(90)-AAATGTGAAGAATGTG-(4
6)-TCATACTGGAGAGAAA-(149)-TCATACTGGAGAGAAA-(174)-AAATGTGAAGAATGTG-(130)-TCATACTGGAGAGAAA-(6)-AAATGTGAAGAATGTG-(152)
.

FIG. 13C (SEQ ID NO: 49):
>AMINO-ACID CODING REGION OF ENST00000356194||ENSG00000196081_CHR=7_STRAND=FORWARD
-(132)-AAATGTGAAGAATGTG-(65)-AAATGTGAAGAATGTG-(68)-AAATGTGAAGAATGTG-(130)-TCATACTGGAGAGAAA-(6
8)-TCATACTGGAGAGAAA-(65)-AATTCATATGGAATTG-(9)-AAATGTGAAGAATGTG-(29)-ACTAATCATAAGAAGAA-(3)-ACACTGGAGAGAAACC-(4)-AAAT
GTGAAGAATGTG-(68)-AAATGTGAAGAATGTG-(13)-

(SEQ ID NO: 50):
>AMINO-ACID CODING REGION OF ENST00000356096||ENSG00000197372_CHR=19_STRAND=REVERSE
-(307)-AAAAATGTGGAAATGA-(130)-TTTAATAAATTTCAC-(44)-AAATGTAAAGAATGTG-(39)-AAAGAAATTATACCAA-(94)-AAATGTGAAGAATGTG-(68)-
AAATGTGAAGAATGTG-(152)-AAATGTGAAGAATGTG-(13)-ACACTCCTCAGCCCTT-(19)-ACACTGGAGAGAAACC-(4)-AAA
TGTGAAGAATGTG-(68)-AAATGTGAAGAATGTG-(66)-ACAAGTGTGAAGAATGTG-(70)-AAATGTGAAGAATGTG-(46)-TCATACTGGAGAGAAA-(105)-

(SEQ ID NO: 51):
>AMINO-ACID CODING REGION OF ENST00000345030||ENSG00000198153_CHR=7_STRAND=FORWARD
-(21)-CAGCCAGAGCAGGGCA-(232)-AAAGAAACATTTCAAA-(143)-TCATACTGGAGAGAAA-(68)-TCATACTGGAGAGAAA-(90)-AAATGTGAAGAATGTG-(4
6)-TCATACTGGAGAGAAA-(152)-TCATACTGGAGAGAAA-(174)-AAATGTGAAGAATGTG-(130)-TCATACTGGAGAGAAA-(6)-AAATGTGAAGAATGTG-(253)
-TCATACTGGAGAGAAA-(6)-AAATGTGAAGAATGTG-(17)-

(SEQ ID NO: 52):
>AMINO-ACID CODING REGION OF ENST00000357051||ENSG00000198584_CHR=10_STRAND=REVERSE
-(230)-TTTACAAATAAGAAAA-(174)-AAATGTAAAGAATGTG-(47)-CATACTGAAGAGAAAC-(87)-ACAAGTGTGAAGAATG-(70)-AAATGTGAAGAATGTG-(16
1)-AAATGTGAAGAATGTG-(68)-AAATGTGAAGAATGTG-(47)-CATACTGAAGAGAAAC-(5)-AAATGTGAAGAATGTG-(47)-CATACTGAAGAGAAAC-(10)-TG
AAGAATGTATCAGA-(41)-TCATACTGGAGAGAAA-(30)-

FIG. 13

| FIG. 13A |
| FIG. 13B |
| FIG. 13C |

NOTE: PROBABILITY DENSITY FUNCTION (SOLID LINE) AND THE CORRESPONDING
CUMULATIVE (DASHED LINE) FOR THE VARIABLE REPRESENTING THE FRACTION OF THE
INSTANCES OF PYKNONS WHICH ARE LOCATED IN REGIONS THAT ARE FREE OF REPEATS.

FIG. 15

| GO TERM | 5' UTR | | CODING | | 3' UTR | |
|---|---|---|---|---|---|---|
| | ENRICHMENT DEPLETION | \|log(p-value)\| | ENRICHMENT DEPLETION | \|log(p-value)\| | ENRICHMENT DEPLETION | \|log(p-value)\| |
| DNA CATABOLISM | 39.54 | 19.88 | | | 89.64 | 23.05 |
| MUSCLE CELL DIFFERENTIATION | 33.85 | 27.11 | 47.16 | 28.08 | | |
| REGULATION OF TRANSCRIPTION, DNA-DEPENDENT | 235.36 | 10.88 | 381.97 | 5.49 | 965.04 | 27.11 |
| REGULATION OF PHYSIOLOGICAL PROCESS | 244.20 | 8.66 | 425.77 | 5.14 | 1006.37 | 22.11 |
| NUCLEO-{BASE, SIDE, TIDE} AND NUCLEIC ACID METABOLISM | 290.72 | 11.57 | 1269.93 | 46.78 | 743.14 | 10.27 |
| REGULATION OF METABOLISM | 233.19 | 9.58 | 494.99 | 8.95 | 1018.81 | 27.33 |
| DNA TRANSPOSITION | | | 462.51 | 229.02 | 37.92 | 13.86 |
| DNA METABOLISM | 82.90 | 2.84 | 1219.01 | 155.71 | -316.84 | 8.61 |
| DNA REPLICATION | | | 660.51 | 154.68 | -149.86 | 7.10 |
| MORPHOGENESIS | -117.23 | 3.27 | 287.34 | 4.43 | -488.46 | 9.93 |
| ORGANOGENESIS | -135.48 | 6.58 | 208.11 | 2.34 | -428.31 | 9.26 |
| DEFENSE RESPONSE TO BACTERIA | -27.87 | 4.33 | -94.99 | 10.88 | -185.21 | 34.41 |
| DETECTION OF EXTERNAL STIMULUS | -74.31 | 5.18 | -331.11 | 13.97 | -318.25 | 15.72 |
| ORGANISMAL PHYSIOLOGICAL PROCESS | -136.14 | 3.06 | -607.27 | 15.84 | -616.45 | 11.86 |
| RESPONSE TO EXTERNAL STIMULUS | -156.16 | 7.91 | -725.13 | 34.01 | -684.40 | 23.25 |

NOTE: PARTIAL LIST OF BIOLOGICAL PROCESSES WHOSE CORRESPONDING GENES SHOW SIGNIFICANT ENRICHMENT (LIGHT SHADED CELLS) OR DEPLETION (DARK SHADED CELLS) IN PYKNON INSTANCES IN THEIR 5'UTR, CR OR 3'UTR. ALL SHOWN log(p-values) HAVE BEEN BONFERRONI-CORRECTED. THOSE OF THE TERMS THAT ARE CONSISTENTLY ENRICHED (RESP. DEPLETED) IN ALL THREE REGIONS ARE COLORED LIGHT SHADE (RESP. DARK SHADE).

NOTE: PYKNONS AND THEIR NATURAL BOUNDARIES: PROBABILITY DENSITY FUNCTIONS FOR THE DISTANCE BETWEEN THE STARTING POINTS OF CONSECUTIVE INSTANCES OF THE PYKNONS, SHOWN SEPARATELY FOR EACH OF THE THREE STUDIED REGIONS, NAMELY 5'UTRs, CRs AND 3'UTRs. THE DISTRIBUTIONS ARE TAIL-HEAVY AND ONLY A PORTION OF THEM IS SHOWN. NOTE THE PEAKS AT ABSCISSAS 18, 22, 24, 26, 29, 30 AND 31.

NOTE: PYKNONS AND THEIR NATURAL BOUNDARIES. PROBABILITY DENSITY FUNCTIONS FOR THE NUMBER OF INTERGENIC (TOP) AND INTRONIC (BOTTOM) COPIES OF THE VARIABLE-LENGTH STRINGS DERIVED BY COUNTING THE INSTANCES OF 3'UTR-CONSERVED PYKNONS AFTER HAVING SHIFTED THEM TO THE RIGHT BY d POSITIONS. IN BOTH CASES, THE CURVES THAT CORRESPOND TO d=0 ARE FOR THE PYKNONS IN $P_{3'UTR}$.

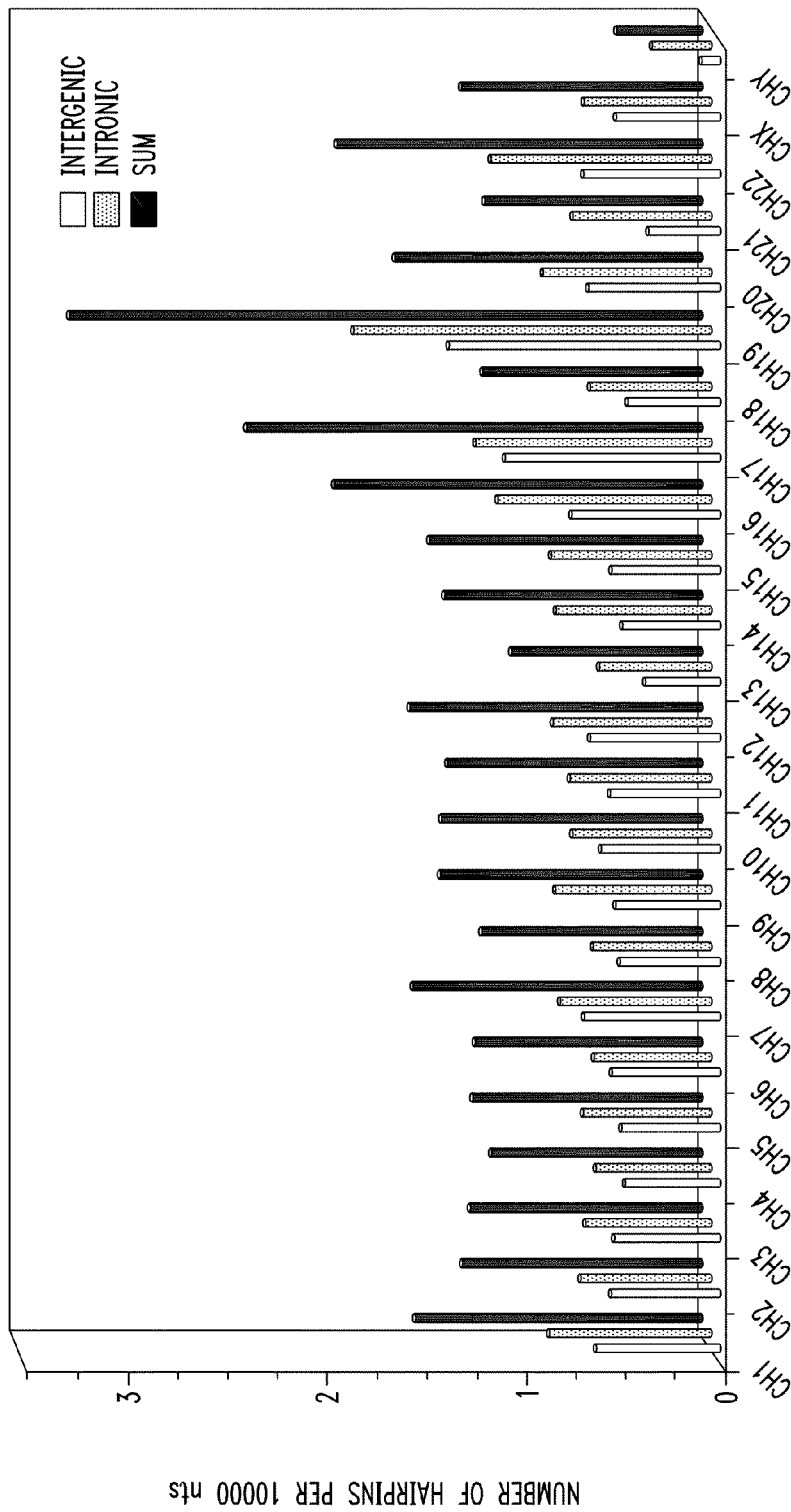

FIG. 18

NOTE: NUMBER OF INTERGENIC/INTRONIC NEIGHBORHOODS, GENERALLY 60 TO 80 NUCLEOTIDES IN LENGTH, EACH OF WHICH CONTAINS THE REVERSE-COMPLEMENT OF A PYKNON AND IS PREDICTED TO FORM DOUBLE-STRANDED, ENERGETICALLY-STABLE, HAIRPIN-SHAPED RNA SECONDARY STRUCTURES - THE NUMBER IS GIVEN PER 10,000 nts OF SEQUENCE. RESULTS ARE SHOWN SEPARATELY FOR EACH CHROMOSOME AND FOR THE INTERGENIC AND INTRONIC REGIONS. THE AVERAGE NUMBER OF HAIRPINS PER 10,000 nts INDEPENDENT OF PROVENANCE IS ALSO SHOWN IN SUM.

FIG. 19

| PATTERN SET/ REGION | POSITIONS COVERED IN CORRESPONDING REGION OF LISTED GENOME PER 10,000 NUCLEOTIDES | | | | | | |
|---|---|---|---|---|---|---|---|
| | HAS | CFA | MMU | RNO | GGA | DME | CEL |
| $P_{5'UTR}$/5'UTR | 382.2 | 43.0 | 20.7 | 14.2 | 9.7 | 22.4 | 5.8 |
| $P_{CODING}$/CODING | 304.1 | 88.3 | 57.4 | 61.1 | 28.4 | 25.2 | 14.7 |
| $P_{3'UTR}$/3'UTR | 733.3 | 152.4 | 82.6 | 64.9 | 42.1 | 65.9 | 57.1 |

NOTE: FOR EACH OF THE THREE REGIONS AND EACH GENOME IN TURN, WE REPORT THE NUMBER OF POSITIONS PER 10,000 NUCLEOTIDES THAT ARE COVERED BY INSTANCES OF THE HUMAN PYKNONS: WE USE THE PATTERNS CONTAINED IN THE SET $P_X$ TO SEARCH REGION X OF THE GENOME X={5'UTR, CODING, 3'UTR} - HSA=HUMAN, CFA=DOG, MMU=MOUSE, RNO=RAT, GGA=CHICKEN, DME=FRUIT-FLY, CEL=WORM.

FIG. 20

| GENOME | NUMBER OF HUMAN PYKNONS WITH ≥ 1 INSTANCE IN THE CORRESPONDING REGION OF LISTED GENOME | | | TOTAL SIZE OF INTERGENIC/INTRONIC REGION (BOTH STRANDS) | INTERGENIC/INTRONIC POSITIONS (BOTH STRANDS) COVERED BY HUMAN PYKNONS | |
|---|---|---|---|---|---|---|
| | $P_{5'UTR}$ | $P_{CODING}$ | $P_{3'UTR}$ | | in nts | per 10,000 nts |
| HSA | 12,267 | 54,396 | 67,544 | 6,093,304,675 | 692,393,548 | 1,136 |
| CFA | 234 | 6,170 | 1,351 | 4,826,002,769 | 87,572,989 | 181.5 |
| MMU | 400 | 8,767 | 6,160 | 5,216,777,897 | 89,568,584 | 171.7 |
| RNO | 170 | 3,424 | 1,644 | 5,409,179,291 | 82,635,080 | 152.8 |
| GGA | 51 | 1,786 | 718 | 1,855,717,211 | 9,262,198 | 49.91 |
| DME | 174 | 1,335 | 1,175 | 228,181,521 | 1,562,508 | 68.5 |
| CEL | 20 | 996 | 790 | 170,879,577 | 1,634,993 | 95.7 |

NOTE: SEEKING INSTANCES OF THE HUMAN PYKNONS IN THE INTERGENIC/INTRONIC REGIONS OF OTHER GENOMES. SEPARATELY FOR SEVEN GENOMES AND FOR EACH 5'UTR, CR AND 3'UTR WE SHOW THE NUMBER OF HUMAN PYKNONS THAT ARE CONSERVED IN THE HUMAN GENOME AND THE CORRESPONDING REGION OF THE j-th GENOME. ALSO, FOR ALL THE PYKNONS WHOSE INSTANCES APPEAR IN COUNTERPART REGIONS OF BOTH THE HUMAN AND THE j-th GENOME, WE SEARCH THE j-th GENOME'S INTERGENIC/INTRONIC REGIONS FOR INSTANCES OF THESE COMMON PYKNONS AND REPORT THE TOTAL NUMBER OF POSITIONS COVERED BY THEIR COPIES; ALSO LISTED IS THE NUMBER OF COVERED POSITIONS PER 10,000 NUCLEOTIDES. HSA=HUMAN, CFA=DOG, MMU=MOUSE, RNO=RAT, GGA=CHICKEN, DME=FRUIT-FLY, CEL=WORM.

SEQUENCE LISTING

```
<160> NUMBER OF SEQ ID NOS: 52

<210> SEQ ID NO 1
<211> LENGTH: 18
<212> TYPE: DNA
<213> ORGANISM: Unknown
<220> FEATURE:
<223> OTHER INFORMATION: The pattern is a representation of an 18-
      nucleotide core motif presently assumed to be present in all
      variations of the logical unit which appears several times in
      the intergenic/intronic regions of the human genome.

<400> SEQUENCE: 1
tcccatacca cggggatt                                                   18

<210> SEQ ID NO 2
<211> LENGTH: 18
<212> TYPE: DNA
<213> ORGANISM: Unknown
<220> FEATURE:
<223> OTHER INFORMATION: The pattern is a representation of a core
      pattern presently assumed to be present in all variations of the
      logical unit which appears several times in the intergenic/
      intronic regions of the human genome.
```

```
<400> SEQUENCE: 2
tcccatacca cggggatt                                                    18

<210> SEQ ID NO 3
<211> LENGTH: 19
<212> TYPE: DNA
<213> ORGANISM: Unknown
<220> FEATURE:
<223> OTHER INFORMATION: The pattern is a representation of a core
      pattern presently assumed to be present in all variations of the
      logical unit which appears several times in the intergenic/
      intronic regions of the human genome.

<400> SEQUENCE: 3
tcccatacca cggggatta                                                   19

<210> SEQ ID NO 4
<211> LENGTH: 19
<212> TYPE: DNA
<213> ORGANISM: Unknown
<220> FEATURE:
<223> OTHER INFORMATION: The pattern is a representation of a core
      pattern presently assumed to be present in all variations of the
      logical unit which appears several times in the intergenic/
      intronic regions of the human genome.

<400> SEQUENCE: 4
ctcccatacc acggggatt                                                   19

<210> SEQ ID NO 5
<211> LENGTH: 20
<212> TYPE: DNA
<213> ORGANISM: Unknown
<220> FEATURE:
<223> OTHER INFORMATION: The pattern is a representation of a core
      pattern presently assumed to be present in all variations of the
      logical unit which appears several times in the intergenic/
      intronic regions of the human genome.

<400> SEQUENCE: 5
ctcccatacc acggggatta                                                  20

<210> SEQ ID NO 6
<211> LENGTH: 20
<212> TYPE: DNA
<213> ORGANISM: Unknown
<220> FEATURE:
<223> OTHER INFORMATION: The pattern is a representation of a core
      pattern presently assumed to be present in all variations of the
      logical unit which appears several times in the intergenic/
      intronic regions of the human genome.

<400> SEQUENCE: 6
tcccatacca cggggattac                                                  20

<210> SEQ ID NO 7
<211> LENGTH: 21
<212> TYPE: DNA
<213> ORGANISM: Unknown
<220> FEATURE:
<223> OTHER INFORMATION: The pattern is a representation of a core
      pattern presently assumed to be present in all variations of the
      logical unit which appears several times in the intergenic/
      intronic regions of the human genome.

<400> SEQUENCE: 7
gcctcccata ccacggggat t                                                21
```

```
<210> SEQ ID NO 8
<211> LENGTH: 21
<212> TYPE: DNA
<213> ORGANISM: Unknown
<220> FEATURE:
<223> OTHER INFORMATION: The pattern is a representation of a core
      pattern presently assumed to be present in all variations of the
      logical unit which appears several times in the intergenic/
      intronic regions of the human genome.

<400> SEQUENCE: 8
tcccatacca cggggattac a                                              21

<210> SEQ ID NO 9
<211> LENGTH: 22
<212> TYPE: DNA
<213> ORGANISM: Unknown
<220> FEATURE:
<223> OTHER INFORMATION: The pattern is a representation of a core
      pattern presently assumed to be present in all variations of the
      logical unit which appears several times in the intergenic/
      intronic regions of the human genome.

<400> SEQUENCE: 9
gcctcccata ccacggggat ta                                             22

<210> SEQ ID NO 10
<211> LENGTH: 24
<212> TYPE: DNA
<213> ORGANISM: Unknown
<220> FEATURE:
<223> OTHER INFORMATION: The pattern is a representation of a core
      pattern presently assumed to be present in all variations of the
      logical unit which appears several times in the intergenic/
      intronic regions of the human genome.

<400> SEQUENCE: 10
gcctcccata ccacggggat taca                                           24

<210> SEQ ID NO 11
<211> LENGTH: 23
<212> TYPE: DNA
<213> ORGANISM: Unknown
<220> FEATURE:
<223> OTHER INFORMATION: The pattern is a representation of a core
      pattern presently assumed to be present in all variations of the
      logical unit which appears several times in the intergenic/
      intronic regions of the human genome.

<400> SEQUENCE: 11
ggcctcccat accacgggga tta                                            23

<210> SEQ ID NO 12
<211> LENGTH: 16
<212> TYPE: DNA
<213> ORGANISM: Unknown
<220> FEATURE:
<223> OTHER INFORMATION: The pattern is an example of a pyknon.

<400> SEQUENCE: 12
tgcactccag cctggg                                                    16

<210> SEQ ID NO 13
<211> LENGTH: 19
<212> TYPE: DNA
<213> ORGANISM: Unknown
<220> FEATURE:
<223> OTHER INFORMATION: The pattern is an example of a pyknon.
```

-continued

<400> SEQUENCE: 13
taatcccagc actttggga					19

<210> SEQ ID NO 14
<211> LENGTH: 17
<212> TYPE: DNA
<213> ORGANISM: Unknown
<220> FEATURE:
<223> OTHER INFORMATION: The pattern is an example of a pyknon.

<400> SEQUENCE: 14
ggctgaggca ggagaat					17

<210> SEQ ID NO 15
<211> LENGTH: 16
<212> TYPE: DNA
<213> ORGANISM: Unknown
<220> FEATURE:
<223> OTHER INFORMATION: The pattern is an example of a pyknon.

<400> SEQUENCE: 15
gaggttgcag tgagcc					16

<210> SEQ ID NO 16
<211> LENGTH: 1748
<212> TYPE: DNA
<213> ORGANISM: Unknown
<220> FEATURE:
<223> OTHER INFORMATION: The pattern is a combinatorial arrangement
      of pyknons in 3'UTRs.
<220> FEATURE:
<221> NAME/KEY: misc_feature
<223> OTHER INFORMATION: n indicates the number of nucleotides
      separating the pyknons that surround it, as specified by Figure
      11A.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)

-continued

```
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (260)..(260)
<223> OTHER INFORMATION: n is a, c, g, or t
<220> FEATURE:
<221> NAME/KEY: misc_feature
<222> LOCATION: (278)..(278)
<223> OTHER INFORMATION: n is a, c, g, or t
<220> FEATURE:
<221> NAME/KEY: misc_feature
<222> LOCATION: (295)..(295)
<223> OTHER INFORMATION: n is a, c, g, or t
<220> FEATURE:
<221> NAME/KEY: misc_feature
<222> LOCATION: (312)..(312)
<223> OTHER INFORMATION: n is a, c, g, or t
<220> FEATURE:
<221> NAME/KEY: misc_feature
<222> LOCATION: (348)..(348)
<223> OTHER INFORMATION: n is a, c, g, or t
<220> FEATURE:
<221> NAME/KEY: misc_feature
<222> LOCATION: (365)..(365)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (436)..(436)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (490)..(490)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (560)..(560)
```

-continued

```
<223> OTHER INFORMATION: n is a, c, g, or t
<220> FEATURE:
<221> NAME/KEY: misc_feature
<222> LOCATION: (577)..(577)
<223> OTHER INFORMATION: n is a, c, g, or t
<220> FEATURE:
<221> NAME/KEY: misc_feature
<222> LOCATION: (594)..(594)
<223> OTHER INFORMATION: n is a, c, g, or t
<220> FEATURE:
<221> NAME/KEY: misc_feature
<222> LOCATION: (611)..(611)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
<221> NAME/KEY: misc_feature
<222> LOCATION: (685)..(685)
<223> OTHER INFORMATION: n is a, c, g, or t
<220> FEATURE:
<221> NAME/KEY: misc_feature
<222> LOCATION: (702)..(702)
<223> OTHER INFORMATION: n is a, c, g, or t
<220> FEATURE:
<221> NAME/KEY: misc_feature
<222> LOCATION: (719)..(719)
<223> OTHER INFORMATION: n is a, c, g, or t
<220> FEATURE:
<221> NAME/KEY: misc_feature
<222> LOCATION: (737)..(737)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (772)..(772)
<223> OTHER INFORMATION: n is a, c, g, or t
<220> FEATURE:
<221> NAME/KEY: misc_feature
<222> LOCATION: (789)..(789)
<223> OTHER INFORMATION: n is a, c, g, or t
<220> FEATURE:
<221> NAME/KEY: misc_feature
<222> LOCATION: (822)..(822)
<223> OTHER INFORMATION: n is a, c, g, or t
<220> FEATURE:
<221> NAME/KEY: misc_feature
<222> LOCATION: (839)..(839)
<223> OTHER INFORMATION: n is a, c, g, or t
<220> FEATURE:
<221> NAME/KEY: misc_feature
<222> LOCATION: (856)..(856)
<223> OTHER INFORMATION: n is a, c, g, or t
<220> FEATURE:
<221> NAME/KEY: misc_feature
<222> LOCATION: (889)..(889)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (923)..(923)
<223> OTHER INFORMATION: n is a, c, g, or t
<220> FEATURE:
<221> NAME/KEY: misc_feature
<222> LOCATION: (940)..(940)
<223> OTHER INFORMATION: n is a, c, g, or t
<220> FEATURE:
<221> NAME/KEY: misc_feature
<222> LOCATION: (957)..(957)
```

-continued

```
<223> OTHER INFORMATION: n is a, c, g, or t
<220> FEATURE:
<221> NAME/KEY: misc_feature
<222> LOCATION: (974)..(974)
<223> OTHER INFORMATION: n is a, c, g, or t
<220> FEATURE:
<221> NAME/KEY: misc_feature
<222> LOCATION: (991)..(991)
<223> OTHER INFORMATION: n is a, c, g, or t
<220> FEATURE:
<221> NAME/KEY: misc_feature
<222> LOCATION: (1008)..(1008)
<223> OTHER INFORMATION: n is a, c, g, or t
<220> FEATURE:
<221> NAME/KEY: misc_feature
<222> LOCATION: (1025)..(1025)
<223> OTHER INFORMATION: n is a, c, g, or t
<220> FEATURE:
<221> NAME/KEY: misc_feature
<222> LOCATION: (1042)..(1042)
<223> OTHER INFORMATION: n is a, c, g, or t
<220> FEATURE:
<221> NAME/KEY: misc_feature
<222> LOCATION: (1059)..(1059)
<223> OTHER INFORMATION: n is a, c, g, or t
<220> FEATURE:
<221> NAME/KEY: misc_feature
<222> LOCATION: (1076)..(1076)
<223> OTHER INFORMATION: n is a, c, g, or t
<220> FEATURE:
<221> NAME/KEY: misc_feature
<222> LOCATION: (1096)..(1096)
<223> OTHER INFORMATION: n is a, c, g, or t
<220> FEATURE:
<221> NAME/KEY: misc_feature
<222> LOCATION: (1113)..(1113)
<223> OTHER INFORMATION: n is a, c, g, or t
<220> FEATURE:
<221> NAME/KEY: misc_feature
<222> LOCATION: (1130)..(1130)
<223> OTHER INFORMATION: n is a, c, g, or t
<220> FEATURE:
<221> NAME/KEY: misc_feature
<222> LOCATION: (1147)..(1147)
<223> OTHER INFORMATION: n is a, c, g, or t
<220> FEATURE:
<221> NAME/KEY: misc_feature
<222> LOCATION: (1164)..(1164)
<223> OTHER INFORMATION: n is a, c, g, or t
<220> FEATURE:
<221> NAME/KEY: misc_feature
<222> LOCATION: (1181)..(1181)
<223> OTHER INFORMATION: n is a, c, g, or t
<220> FEATURE:
<221> NAME/KEY: misc_feature
<222> LOCATION: (1198)..(1198)
<223> OTHER INFORMATION: n is a, c, g, or t
<220> FEATURE:
<221> NAME/KEY: misc_feature
<222> LOCATION: (1215)..(1215)
<223> OTHER INFORMATION: n is a, c, g, or t
<220> FEATURE:
<221> NAME/KEY: misc_feature
<222> LOCATION: (1232)..(1232)
<223> OTHER INFORMATION: n is a, c, g, or t
<220> FEATURE:
<221> NAME/KEY: misc_feature
<222> LOCATION: (1265)..(1265)
<223> OTHER INFORMATION: n is a, c, g, or t
<220> FEATURE:
<221> NAME/KEY: misc_feature
<222> LOCATION: (1282)..(1282)
<223> OTHER INFORMATION: n is a, c, g, or t
<220> FEATURE:
<221> NAME/KEY: misc_feature
<222> LOCATION: (1319)..(1319)
<223> OTHER INFORMATION: n is a, c, g, or t
<220> FEATURE:
<221> NAME/KEY: misc_feature
<222> LOCATION: (1336)..(1336)
```

-continued

```
<223> OTHER INFORMATION: n is a, c, g, or t
<220> FEATURE:
<221> NAME/KEY: misc_feature
<222> LOCATION: (1353)..(1353)
<223> OTHER INFORMATION: n is a, c, g, or t
<220> FEATURE:
<221> NAME/KEY: misc_feature
<222> LOCATION: (1389)..(1389)
<223> OTHER INFORMATION: n is a, c, g, or t
<220> FEATURE:
<221> NAME/KEY: misc_feature
<222> LOCATION: (1406)..(1406)
<223> OTHER INFORMATION: n is a, c, g, or t
<220> FEATURE:
<221> NAME/KEY: misc_feature
<222> LOCATION: (1427)..(1427)
<223> OTHER INFORMATION: n is a, c, g, or t
<220> FEATURE:
<221> NAME/KEY: misc_feature
<222> LOCATION: (1468)..(1468)
<223> OTHER INFORMATION: n is a, c, g, or t
<220> FEATURE:
<221> NAME/KEY: misc_feature
<222> LOCATION: (1488)..(1488)
<223> OTHER INFORMATION: n is a, c, g, or t
<220> FEATURE:
<221> NAME/KEY: misc_feature
<222> LOCATION: (1505)..(1505)
<223> OTHER INFORMATION: n is a, c, g, or t
<220> FEATURE:
<221> NAME/KEY: misc_feature
<222> LOCATION: (1526)..(1526)
<223> OTHER INFORMATION: n is a, c, g, or t
<220> FEATURE:
<221> NAME/KEY: misc_feature
<222> LOCATION: (1543)..(1543)
<223> OTHER INFORMATION: n is a, c, g, or t
<220> FEATURE:
<221> NAME/KEY: misc_feature
<222> LOCATION: (1560)..(1560)
<223> OTHER INFORMATION: n is a, c, g, or t
<220> FEATURE:
<221> NAME/KEY: misc_feature
<222> LOCATION: (1577)..(1577)
<223> OTHER INFORMATION: n is a, c, g, or t
<220> FEATURE:
<221> NAME/KEY: misc_feature
<222> LOCATION: (1595)..(1595)
<223> OTHER INFORMATION: n is a, c, g, or t
<220> FEATURE:
<221> NAME/KEY: misc_feature
<222> LOCATION: (1612)..(1612)
<223> OTHER INFORMATION: n is a, c, g, or t
<220> FEATURE:
<221> NAME/KEY: misc_feature
<222> LOCATION: (1629)..(1629)
<223> OTHER INFORMATION: n is a, c, g, or t
<220> FEATURE:
<221> NAME/KEY: misc_feature
<222> LOCATION: (1646)..(1646)
<223> OTHER INFORMATION: n is a, c, g, or t
<220> FEATURE:
<221> NAME/KEY: misc_feature
<222> LOCATION: (1663)..(1663)
<223> OTHER INFORMATION: n is a, c, g, or t
<220> FEATURE:
<221> NAME/KEY: misc_feature
<222> LOCATION: (1680)..(1680)
<223> OTHER INFORMATION: n is a, c, g, or t
<220> FEATURE:
<221> NAME/KEY: misc_feature
<222> LOCATION: (1697)..(1697)
<223> OTHER INFORMATION: n is a, c, g, or t
<220> FEATURE:
<221> NAME/KEY: misc_feature
<222> LOCATION: (1714)..(1714)
<223> OTHER INFORMATION: n is a, c, g, or t
<220> FEATURE:
<221> NAME/KEY: misc_feature
<222> LOCATION: (1731)..(1731)
```

<223> OTHER INFORMATION: n is a, c, g, or t
<220> FEATURE:
<221> NAME/KEY: misc_feature
<222> LOCATION: (1748)..(1748)
<223> OTHER INFORMATION: n is a, c, g, or t

<400> SEQUENCE: 16

```
ntttcttgat ttttcagnat actgatttaa tttcnatttt cttttaaagt tnactgacat      60
ggaaagatnt gtattacttt tgtaanattt ttagaaagta ttntggatga aaaatatttn     120
ctcacaacaa acctatnatt catttaaaac attncttttt gagatggagt cttncccagg     180
ctggagtgca natctctgct cactgcangc cttctgggtt caagnattct cgtgcctcag     240
cnagtagctg gaattacagn gccaccatgc ccgactantt ggccaggctg gtatnaactc     300
ctgacctcaa gntcccaaag tgctgggatt acaggcttga gccaccantt attttacatt     360
ttagnaaatt tgtattttga ancagtggct cacgcctgta atcccagcac tttggganga     420
tcacgaggtc aggagnagac catcctggct aacantctct actaaaaaac anttagccgg     480
gcgtggtggn ctgtagtccc agctactngg ctgaggcagg agaatggtgt gaacccggga     540
ggngagcttg cagtgagccn tgcactccag cctgggnaga gcaagactct gtcntctgtg     600
aaaggaaaat nactcccatc ctaatacncg gtggctcatg cctgtaatcc cagcactttg     660
ggangatcac ctgaggtcgg gaggnagacc agcctgacca anttagctgg gcgtggtgnc     720
tgtaatccca gctactnggc tgaggcagga gaatncttga acccaggagg cngaggttgt     780
ggtgagcgnt gcactccagc ctgggcaaca agagcaaaac tnttagccag gcgtggtgng     840
cagctactct ggaggnagag gcaggaggat cacttgagcc catgaattng aggcagcagt     900
gagctntgta ctccagtctg ggnacagagt gagaccccan ttgaaaagat tattctntca     960
ttttacaggt gagnccatgg attcaaccaa nctgttgtta agcaacanta acaactattt    1020
acatnagcaa ttattttaa anattgtatt aggtattanc cagcctggac aaaagnaaac    1080
cctgtctcta caaaanttag ctgggcatgg tgntgtagtc ctggctactn ggaggatcgc    1140
ttgagtngag gctgcattga gctntgcatt ccagcctggg nagaccttgt ctcagaanat    1200
tatatgcaaa tactncagtc tcactgtgtt gnggatggag tgcaatggca caatcttggc    1260
tcatncagct gggactacag gngtgcccag ttaatttttt ttgtattctt agtagagant    1320
tggccaggct agtctnaatt tctgacctca agntcccaaa gtgctgggat tacaggcgtg    1380
agccaccant tgaccaggct ggtctnaact cctgatctca ggtgatnctc ggcctcacaa    1440
agtgctggga ttacaggtgt gaaccacngg cacggtggct cacgcctncc gaggctgagg    1500
caggnctcac ctgaggtcag gagtttnagac cagcctggcc aanccctgtct gtacaaaaan    1560
atagctgggc atggtgnctg tagtcccagc tactnactga ggcaggagaa tncttgaacc    1620
tgggaggcng aggttgcagg gagccncgca ctccagccta ggngatagag tgagactccn    1680
atgttttgag acagagngaa aactaagaaa attnttattt ttctgtgaat ncaataaaat    1740
actattcn                                                             1748
```

<210> SEQ ID NO 17
<211> LENGTH: 603
<212> TYPE: DNA
<213> ORGANISM: Unknown
<220> FEATURE:
<223> OTHER INFORMATION: The pattern is a combinatorial arrangement of
      pyknons in 3'UTRs.
<220> FEATURE:
<221> NAME/KEY: misc_feature
<223> OTHER INFORMATION: n indicates the number of nucleotides
      separating the pyknons that surround it, as specified by Figure

```
        11B.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (94)..(94)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (130)..(130)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (164)..(164)
<223> OTHER INFORMATION: n is a, c, g, or t
<220> FEATURE:
<221> NAME/KEY: misc_feature
<222> LOCATION: (181)..(181)
<223> OTHER INFORMATION: n is a, c, g, or t
<220> FEATURE:
<221> NAME/KEY: misc_feature
<222> LOCATION: (198)..(198)
<223> OTHER INFORMATION: n is a, c, g, or t
<220> FEATURE:
<221> NAME/KEY: misc_feature
<222> LOCATION: (234)..(234)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (288)..(288)
<223> OTHER INFORMATION: n is a, c, g, or t
<220> FEATURE:
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (322)..(322)
<223> OTHER INFORMATION: n is a, c, g, or t
<220> FEATURE:
<221> NAME/KEY: misc_feature
<222> LOCATION: (339)..(339)
<223> OTHER INFORMATION: n is a, c, g, or t
<220> FEATURE:
<221> NAME/KEY: misc_feature
<222> LOCATION: (356)..(356)
```

<223> OTHER INFORMATION: n is a, c, g, or t
<220> FEATURE:
<221> NAME/KEY: misc_feature
<222> LOCATION: (373)..(373)
<223> OTHER INFORMATION: n is a, c, g, or t
<220> FEATURE:
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (410)..(410)
<223> OTHER INFORMATION: n is a, c, g, or t
<220> FEATURE:
<221> NAME/KEY: misc_feature
<222> LOCATION: (448)..(448)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (535)..(535)
<223> OTHER INFORMATION: n is a, c, g, or t
<220> FEATURE:
<221> NAME/KEY: misc_feature
<222> LOCATION: (552)..(552)
<223> OTHER INFORMATION: n is a, c, g, or t
<220> FEATURE:
<221> NAME/KEY: misc_feature
<222> LOCATION: (569)..(569)
<223> OTHER INFORMATION: n is a, c, g, or t
<220> FEATURE:
<221> NAME/KEY: misc_feature
<222> LOCATION: (586)..(586)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t

<400> SEQUENCE: 17

| | | | | | |
|---|---|---|---|---|---|
| ngccaggtat | ggtggctnta | atcccagcac | tttgggganat | cacctgatgt | caggagttna | 60 |
| gaccagcctg | gccaanacta | gccaggcgtg | gtgnctgtaa | tcccagctac | tnggctgagg | 120 |
| caggagaatn | cttgaaccca | ggaggcngag | gttgcagtga | gccncactgc | actccagccc | 180 |
| ngtgacagtg | tgagactncg | gtggctcaag | cctgtaatcc | cagcactttg | ggangatcac | 240 |
| gaggtcagga | gnagaccatc | ctggctaaca | ntagtcgggc | gtggtggncc | tgtattcaca | 300 |
| gctangaggt | tgaggcagga | gngggtgaac | ccgggaggng | agcttgcagt | gagccntgca | 360 |
| ctccagcctg | ggngacagag | ccagactccn | aggctcacac | ctgtaatccn | gacgctgagg | 420 |
| tgggaggatc | acttgagccc | aggagttntg | gcaatatag | tgaganctac | aaaaaagttt | 480 |
| ttnagcatgg | tggcacatgn | ctgtagtccc | acctactnag | ggtcacctga | gcctngaggc | 540 |
| tgcagtgagc | cntgcactcc | agcctgggna | gagtaagacc | ctgtcntttt | attgagcagt | 600 |
| ttn | | | | | | 603 |

<210> SEQ ID NO 18

```
<211> LENGTH: 1070
<212> TYPE: DNA
<213> ORGANISM: Unknown
<220> FEATURE:
<223> OTHER INFORMATION: The pattern is a combinatorial arrangement of
      pyknons in 3'UTRs.
<220> FEATURE:
<221> NAME/KEY: misc_feature
<223> OTHER INFORMATION: n indicates the number of nucleotides
      separating the pyknons that surround it, as specified by Figure
      11B.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (118)..(118)
<223> OTHER INFORMATION: n is a, c, g, or t
<220> FEATURE:
<221> NAME/KEY: misc_feature
<222> LOCATION: (135)..(135)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (169)..(169)
<223> OTHER INFORMATION: n is a, c, g, or t
<220> FEATURE:
<221> NAME/KEY: misc_feature
<222> LOCATION: (186)..(186)
<223> OTHER INFORMATION: n is a, c, g, or t
<220> FEATURE:
<221> NAME/KEY: misc_feature
<222> LOCATION: (203)..(203)
<223> OTHER INFORMATION: n is a, c, g, or t
<220> FEATURE:
<221> NAME/KEY: misc_feature
<222> LOCATION: (220)..(220)
<223> OTHER INFORMATION: n is a, c, g, or t
<220> FEATURE:
<221> NAME/KEY: misc_feature
<222> LOCATION: (237)..(237)
<223> OTHER INFORMATION: n is a, c, g, or t
<220> FEATURE:
<221> NAME/KEY: misc_feature
<222> LOCATION: (254)..(254)
<223> OTHER INFORMATION: n is a, c, g, or t
<220> FEATURE:
<221> NAME/KEY: misc_feature
<222> LOCATION: (271)..(271)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
```

-continued

```
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (377)..(377)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (411)..(411)
<223> OTHER INFORMATION: n is a, c, g, or t
<220> FEATURE:
<221> NAME/KEY: misc_feature
<222> LOCATION: (428)..(428)
<223> OTHER INFORMATION: n is a, c, g, or t
<220> FEATURE:
<221> NAME/KEY: misc_feature
<222> LOCATION: (445)..(445)
<223> OTHER INFORMATION: n is a, c, g, or t
<220> FEATURE:
<221> NAME/KEY: misc_feature
<222> LOCATION: (462)..(462)
<223> OTHER INFORMATION: n is a, c, g, or t
<220> FEATURE:
<221> NAME/KEY: misc_feature
<222> LOCATION: (479)..(479)
<223> OTHER INFORMATION: n is a, c, g, or t
<220> FEATURE:
<221> NAME/KEY: misc_feature
<222> LOCATION: (496)..(496)
<223> OTHER INFORMATION: n is a, c, g, or t
<220> FEATURE:
<221> NAME/KEY: misc_feature
<222> LOCATION: (513)..(513)
<223> OTHER INFORMATION: n is a, c, g, or t
<220> FEATURE:
<221> NAME/KEY: misc_feature
<222> LOCATION: (530)..(530)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (581)..(581)
<223> OTHER INFORMATION: n is a, c, g, or t
<220> FEATURE:
<221> NAME/KEY: misc_feature
<222> LOCATION: (598)..(598)
<223> OTHER INFORMATION: n is a, c, g, or t
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (632)..(632)
<223> OTHER INFORMATION: n is a, c, g, or t
<220> FEATURE:
<221> NAME/KEY: misc_feature
<222> LOCATION: (649)..(649)
<223> OTHER INFORMATION: n is a, c, g, or t
<220> FEATURE:
<221> NAME/KEY: misc_feature
<222> LOCATION: (685)..(685)
<223> OTHER INFORMATION: n is a, c, g, or t
<220> FEATURE:
```

```
<221> NAME/KEY: misc_feature
<222> LOCATION: (704)..(704)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t
<220> FEATURE:
<221> NAME/KEY: misc_feature
<222> LOCATION: (739)..(739)
<223> OTHER INFORMATION: n is a, c, g, or t
<220> FEATURE:
<221> NAME/KEY: misc_feature
<222> LOCATION: (757)..(757)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t
<220> FEATURE:
<221> NAME/KEY: misc_feature
<222> LOCATION: (793)..(793)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (845)..(845)
<223> OTHER INFORMATION: n is a, c, g, or t
<220> FEATURE:
<221> NAME/KEY: misc_feature
<222> LOCATION: (862)..(862)
<223> OTHER INFORMATION: n is a, c, g, or t
<220> FEATURE:
<221> NAME/KEY: misc_feature
<222> LOCATION: (879)..(879)
<223> OTHER INFORMATION: n is a, c, g, or t
<220> FEATURE:
<221> NAME/KEY: misc_feature
<222> LOCATION: (896)..(896)
<223> OTHER INFORMATION: n is a, c, g, or t
<220> FEATURE:
<221> NAME/KEY: misc_feature
<222> LOCATION: (913)..(913)
<223> OTHER INFORMATION: n is a, c, g, or t
<220> FEATURE:
<221> NAME/KEY: misc_feature
<222> LOCATION: (930)..(930)
<223> OTHER INFORMATION: n is a, c, g, or t
<220> FEATURE:
<221> NAME/KEY: misc_feature
<222> LOCATION: (947)..(947)
<223> OTHER INFORMATION: n is a, c, g, or t
<220> FEATURE:
<221> NAME/KEY: misc_feature
<222> LOCATION: (964)..(964)
<223> OTHER INFORMATION: n is a, c, g, or t
<220> FEATURE:
<221> NAME/KEY: misc_feature
<222> LOCATION: (997)..(997)
<223> OTHER INFORMATION: n is a, c, g, or t
<220> FEATURE:
<221> NAME/KEY: misc_feature
<222> LOCATION: (1016)..(1016)
<223> OTHER INFORMATION: n is a, c, g, or t
<220> FEATURE:
<221> NAME/KEY: misc_feature
<222> LOCATION: (1034)..(1034)
<223> OTHER INFORMATION: n is a, c, g, or t
<220> FEATURE:
<221> NAME/KEY: misc_feature
<222> LOCATION: (1070)..(1070)
<223> OTHER INFORMATION: n is a, c, g, or t
```

-continued

<400> SEQUENCE: 18

```
naaagaagat cattttgnag cagtggctca cacctntaat cccagcactt tggganaggt      60
gggcggatca cccnaaacca gcctgaccaa catggtgaaa ccctgtctct actaaatntt     120 agcgggtgt ggtgngcacc tgtaatcgca gngaggctga dacaggagnc ttgaaccta      180 gaggcngagt ttgcagtgag ccnccattgt actccagctn agtaagactc tgtctcntgg     240
gagtcatcct tganggccag gcatggtggc ntaatcccag catttggga ntgaggtcag     300 gagctcaaga ccagcctggc caantagtcg ggcgtggtgg nctgtaatcc cagctactng     360
gctgaggcag gagaatnctt gaacctggga ggcngaggtt gcagtgagcc ntgtactcca     420
gcctgggnag tgagactctg tcttnctgat aaatattgat gncagctcca ctaggaagnc     480
cattcaattc catttngagc tctttgaggc cancctagca catagtaggn tgaatgaatg     540
aatgaantca ttttatgaag ctantttat cagaaaaaaa nacttaatcc ccagtgtnac     600
aaaggaatga agagnagcat ttaggccatt tnaaatggta tttagaaanc ggtggctcat     660
gcctgtaatc ccagcacttt gggantgagg caggcggatc actnagacca gcctggccaa     720
nttagccggg cgtggtggnc tgtaatccca gctactnagg ctgaggcagg agaaancctg     780
aacccagaag gcngaggttg cagtgagccn cactgcactc cagccgncct ctgtctcaaa     840
aaaantttct ttatctgtaa angtttagaa agtaaaaanc ccaggttgga gtgcanggct     900
cactgcaacc tcngcctccc gggttcaagn ctcctgtctc agcctcngag tacctgggac     960
tacngcccgg ctaattttt gtatttgtag tagagantgt tagccaggat ggtctnctcc    1020
tgacctcatg atcntcccaa agtgctggga ttacaggcgt gagcccccgn              1070
```

```
<210> SEQ ID NO 19
<211> LENGTH: 723
<212> TYPE: DNA
<213> ORGANISM: Unknown
<220> FEATURE:
<223> OTHER INFORMATION: The pattern is a combinatorial arrangement
      of pyknons in 3'UTRs.
<220> FEATURE:
<221> NAME/KEY: misc_feature
<223> OTHER INFORMATION: n indicates the number of nucleotides
      separating the pyknons that surround it, as specified by Figure
      11B.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (90)..(90)
<223> OTHER INFORMATION: n is a, c, g, or t
<220> FEATURE:
<221> NAME/KEY: misc_feature
<222> LOCATION: (107)..(107)
<223> OTHER INFORMATION: n is a, c, g, or t
<220> FEATURE:
```

```
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (211)..(211)
<223> OTHER INFORMATION: n is a, c, g, or t
<220> FEATURE:
<221> NAME/KEY: misc_feature
<222> LOCATION: (228)..(228)
<223> OTHER INFORMATION: n is a, c, g, or t
<220> FEATURE:
<221> NAME/KEY: misc_feature
<222> LOCATION: (245)..(245)
<223> OTHER INFORMATION: n is a, c, g, or t
<220> FEATURE:
<221> NAME/KEY: misc_feature
<222> LOCATION: (262)..(262)
<223> OTHER INFORMATION: n is a, c, g, or t
<220> FEATURE:
<221> NAME/KEY: misc_feature
<222> LOCATION: (279)..(279)
<223> OTHER INFORMATION: n is a, c, g, or t
<220> FEATURE:
<221> NAME/KEY: misc_feature
<222> LOCATION: (316)..(316)
<223> OTHER INFORMATION: n is a, c, g, or t
<220> FEATURE:
<221> NAME/KEY: misc_feature
<222> LOCATION: (333)..(333)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (452)..(452)
<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t
<220> FEATURE:
```

```
<221> NAME/KEY: misc_feature
<222> LOCATION: (526)..(526)
<223> OTHER INFORMATION: n is a, c, g, or t
<220> FEATURE:
<221> NAME/KEY: misc_feature
<222> LOCATION: (543)..(543)
<223> OTHER INFORMATION: n is a, c, g, or t
<220> FEATURE:
<221> NAME/KEY: misc_feature
<222> LOCATION: (564)..(564)
<223> OTHER INFORMATION: n is a, c, g, or t
<220> FEATURE:
<221> NAME/KEY: misc_feature
<222> LOCATION: (581)..(581)
<223> OTHER INFORMATION: n is a, c, g, or t
<220> FEATURE:
<221> NAME/KEY: misc_feature
<222> LOCATION: (602)..(602)
<223> OTHER INFORMATION: n is a, c, g, or t
<220> FEATURE:
<221> NAME/KEY: misc_feature
<222> LOCATION: (619)..(619)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (672)..(672)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (723)..(723)
<223> OTHER INFORMATION: n is a, c, g, or t

<400> SEQUENCE: 19
ncctgttgtg gggagggncg gtggctcatg cctgncatcc cagcactttg gganaacctg      60
aggtcaggag ttnaacaaca tggtgaaacn tgcctgcctg taatccngag ctgaggcag      120 gaaaancttg aacccgaaag gcngaggttg cagtgtgccn cactgaactc cagcctncaa    180
caagagtgaa actntattga acacttacta nggcagagcc aggatttntg tttttttaaaa   240 agaantttac agacaaggaa anggccaggc atggtggcnt aatcccagca gtttgggagg    300
ctgaggtggg aggagnagac cagcctaggc aanccccatct ctacaaaaan ttatctgggc   360
ctggtgnctg tagtcccagc tactnagagg ctgaggtggg ancttgagcc cagaagttga    420
ggctgcagtg agccntgtac tccagcctgg gncaaagcaa aaccctgtnc ggtggctcac    480
acctgtaatc ccaacacttt gganatcac ctgaggtcag gagttnagac cagcctggcc    540
aancctctac tgaaaataca aaangcattg tggcacatgc natcacctga ggtcaggagt    600
tnagaccagc ctggccaant tagctgggcg tggtgnctgt agtcccagct actnggctga    660
ggcaggagaa tncttgaacc tgggaggtng aggttgcagt aagccntgca ctccagcctg    720 ggn                                                                723

<210> SEQ ID NO 20
<211> LENGTH: 826
<212> TYPE: DNA
```

```
-continued

<213> ORGANISM: Unknown
<220> FEATURE:
<223> OTHER INFORMATION: The pattern is a combinatorial arrangement of
      pyknons in 3'UTRs.
<220> FEATURE:
<221> NAME/KEY: misc_feature
<223> OTHER INFORMATION: n indicates the number of nucleotides
      separating the pyknons that surround it, as specified by Figure
      11B.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (102)..(102)
<223> OTHER INFORMATION: n is a, c, g, or t
<220> FEATURE:
<221> NAME/KEY: misc_feature
<222> LOCATION: (119)..(119)
<223> OTHER INFORMATION: n is a, c, g, or t
<220> FEATURE:
<221> NAME/KEY: misc_feature
<222> LOCATION: (152)..(152)
<223> OTHER INFORMATION: n is a, c, g, or t
<220> FEATURE:
<221> NAME/KEY: misc_feature
<222> LOCATION: (204)..(204)
<223> OTHER INFORMATION: n is a, c, g, or t
<220> FEATURE:
<221> NAME/KEY: misc_feature
<222> LOCATION: (224)..(224)
<223> OTHER INFORMATION: n is a, c, g, or t
<220> FEATURE:
<221> NAME/KEY: misc_feature
<222> LOCATION: (241)..(241)
<223> OTHER INFORMATION: n is a, c, g, or t
<220> FEATURE:
<221> NAME/KEY: misc_feature
<222> LOCATION: (258)..(258)
<223> OTHER INFORMATION: n is a, c, g, or t
<220> FEATURE:
<221> NAME/KEY: misc_feature
<222> LOCATION: (276)..(276)
<223> OTHER INFORMATION: n is a, c, g, or t
<220> FEATURE:
<221> NAME/KEY: misc_feature
<222> LOCATION: (293)..(293)
<223> OTHER INFORMATION: n is a, c, g, or t
<220> FEATURE:
<221> NAME/KEY: misc_feature
<222> LOCATION: (310)..(310)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
<220> FEATURE:
<221> NAME/KEY: misc_feature
<222> LOCATION: (361)..(361)
```

```
<223> OTHER INFORMATION: n is a, c, g, or t
<220> FEATURE:
<221> NAME/KEY: misc_feature
<222> LOCATION: (378)..(378)
<223> OTHER INFORMATION: n is a, c, g, or t
<220> FEATURE:
<221> NAME/KEY: misc_feature
<222> LOCATION: (395)..(395)
<223> OTHER INFORMATION: n is a, c, g, or t
<220> FEATURE:
<221> NAME/KEY: misc_feature
<222> LOCATION: (412)..(412)
<223> OTHER INFORMATION: n is a, c, g, or t
<220> FEATURE:
<221> NAME/KEY: misc_feature
<222> LOCATION: (429)..(429)
<223> OTHER INFORMATION: n is a, c, g, or t
<220> FEATURE:
<221> NAME/KEY: misc_feature
<222> LOCATION: (446)..(446)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (497)..(497)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (549)..(549)
<223> OTHER INFORMATION: n is a, c, g, or t
<220> FEATURE:
<221> NAME/KEY: misc_feature
<222> LOCATION: (566)..(566)
<223> OTHER INFORMATION: n is a, c, g, or t
<220> FEATURE:
<221> NAME/KEY: misc_feature
<222> LOCATION: (583)..(583)
<223> OTHER INFORMATION: n is a, c, g, or t
<220> FEATURE:
<221> NAME/KEY: misc_feature
<222> LOCATION: (600)..(600)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (634)..(634)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (689)..(689)
<223> OTHER INFORMATION: n is a, c, g, or t
<220> FEATURE:
<221> NAME/KEY: misc_feature
<222> LOCATION: (706)..(706)
<223> OTHER INFORMATION: n is a, c, g, or t
<220> FEATURE:
<221> NAME/KEY: misc_feature
<222> LOCATION: (723)..(723)
```

```
<223> OTHER INFORMATION: n is a, c, g, or t
<220> FEATURE:
<221> NAME/KEY: misc_feature
<222> LOCATION: (741)..(741)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (776)..(776)
<223> OTHER INFORMATION: n is a, c, g, or t
<220> FEATURE:
<221> NAME/KEY: misc_feature
<222> LOCATION: (793)..(793)
<223> OTHER INFORMATION: n is a, c, g, or t
<220> FEATURE:
<221> NAME/KEY: misc_feature
<222> LOCATION: (826)..(826)
<223> OTHER INFORMATION: n is a, c, g, or t

<400> SEQUENCE: 20
nactgtactg tatttatnat attttacaga aatanttatt catttgttta ancagtggct      60
catgcctgng ctgaggcagg aggacagttt gaggccagga gnagactagc ctggacaant     120
ctctacaaaa acataaaaat aaattagctg gnaaaaatag gctgggtgtg gtggttcatg     180
cctgtaatcc tagcactttg gganggatca cctgaggtca ggtncccaat atggtgaaac     240
ntagccaggt gtggtggnct gtagtcccag ctactngagg ctgacacagg agncttgaac     300
ccaggaagtn gaggctgcag tgagccntgc actccagcct gggnagtgag actctgtctc     360
ngtgtggtgg catgtgtntg tggtcccagc tactnccaga aggtcaaggc tntgagctgt     420
gattgcatnt gcactccagc ctgggnagca agaccctatc tcnaatttac aatttacaan     480
ctgaagaact ttctttnatt ttgtttctaa atanagagat ggggtctcgc tncccaggct     540
ggagtgcant agctcactgc agtctnaaat gcatttttaa aantttctga ttaataaatn     600
tgtatgtgcc acatttncac acacacatgt gtgncagtgg ctcacgcctg taatcccagc     660
actttgggan aacctgaggt caggagttna gaccagcctg accaanttag ccaggcatgg     720
tgnctgtaat cccagctact nggctgaggc aggagaatnc ttgaacccgg gaggcngagg     780
ttgcagttag ccntgcactc cagcctgggc aacaagagta aaactn                    826

<210> SEQ ID NO 21
<211> LENGTH: 730
<212> TYPE: DNA
<213> ORGANISM: Unknown
<220> FEATURE:
<223> OTHER INFORMATION: The pattern is a combinatorial arrangement of
      pyknons in 3'UTRs.
<220> FEATURE:
<221> NAME/KEY: misc_feature
<223> OTHER INFORMATION: n indicates the number of nucleotides
      separating the pyknons that surround it, as specified by Figure
      11B.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
```

-continued

```
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (126)..(126)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (196)..(196)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (401)..(401)
<223> OTHER INFORMATION: n is a, c, g, or t
<220> FEATURE:
<221> NAME/KEY: misc_feature
<222> LOCATION: (418)..(418)
<223> OTHER INFORMATION: n is a, c, g, or t
<220> FEATURE:
<221> NAME/KEY: misc_feature
<222> LOCATION: (435)..(435)
<223> OTHER INFORMATION: n is a, c, g, or t
<220> FEATURE:
<221> NAME/KEY: misc_feature
<222> LOCATION: (452)..(452)
```

<223> OTHER INFORMATION: n is a, c, g, or t
<220> FEATURE:
<221> NAME/KEY: misc_feature
<222> LOCATION: (469)..(469)
<223> OTHER INFORMATION: n is a, c, g, or t
<220> FEATURE:
<221> NAME/KEY: misc_feature
<222> LOCATION: (486)..(486)
<223> OTHER INFORMATION: n is a, c, g, or t
<220> FEATURE:
<221> NAME/KEY: misc_feature
<222> LOCATION: (503)..(503)
<223> OTHER INFORMATION: n is a, c, g, or t
<220> FEATURE:
<221> NAME/KEY: misc_feature
<222> LOCATION: (520)..(520)
<223> OTHER INFORMATION: n is a, c, g, or t
<220> FEATURE:
<221> NAME/KEY: misc_feature
<222> LOCATION: (537)..(537)
<223> OTHER INFORMATION: n is a, c, g, or t
<220> FEATURE:
<221> NAME/KEY: misc_feature
<222> LOCATION: (554)..(554)
<223> OTHER INFORMATION: n is a, c, g, or t
<220> FEATURE:
<221> NAME/KEY: misc_feature
<222> LOCATION: (571)..(571)
<223> OTHER INFORMATION: n is a, c, g, or t
<220> FEATURE:
<221> NAME/KEY: misc_feature
<222> LOCATION: (592)..(592)
<223> OTHER INFORMATION: n is a, c, g, or t
<220> FEATURE:
<221> NAME/KEY: misc_feature
<222> LOCATION: (609)..(609)
<223> OTHER INFORMATION: n is a, c, g, or t
<220> FEATURE:
<221> NAME/KEY: misc_feature
<222> LOCATION: (626)..(626)
<223> OTHER INFORMATION: n is a, c, g, or t
<220> FEATURE:
<221> NAME/KEY: misc_feature
<222> LOCATION: (644)..(644)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
<221> NAME/KEY: misc_feature
<222> LOCATION: (696)..(696)
<223> OTHER INFORMATION: n is a, c, g, or t
<220> FEATURE:
<221> NAME/KEY: misc_feature
<222> LOCATION: (713)..(713)
<223> OTHER INFORMATION: n is a, c, g, or t
<220> FEATURE:
<221> NAME/KEY: misc_feature
<222> LOCATION: (730)..(730)
<223> OTHER INFORMATION: n is a, c, g, or t

<400> SEQUENCE: 21
ncacacacac acccctgnaa ttgttttttc taatncttt tgaattttta ancagtggcc      60
catgcctgta atcccagcac tttggggnat cacctgagga caggagttna gaccagtctg    120
gccaantagc cgggcatggt ggnctgtaat cccagctact nggctgaggc aggagaatnc    180
ttgaacctag gaggcngagg ttgcagtgag ccntgcactc cagcctgggn gacaagagtg    240
aaactcnttt gaattaattt ttcngcctct aaaactgtga ngcatcagaa tcacctgnag    300
ggcttgttaa aacanacatt tattgagctc cnagggcaga ggaaacaanc aatggctcat    360

```
gcctgtaatc ccaacacttt gggaggccaa ggtgggagga nagaccagcc tggacaanag    420
tgagatccta tctcnttagc caggcatggt gncctatagt cctggctang ctgaggcagg    480
aggatnaggc tgcagtaagc cangccactg cactcagccn agcaagaccc tgtctcntct    540
gggctgggca cagncacact ttgggaggcc natcacctga ggtcaggagt tnagaccagc    600
ctggccaant tagctgggcg tggtgnctgt aatcccagct actnggctga ggcaggagaa    660
tncttgaacc caggaggcng aggttgcagt gagccntgca ctccagcctg ggngacaaga    720 gcaaaactcn                                                           730

<210> SEQ ID NO 22
<211> LENGTH: 1097
<212> TYPE: DNA
<213> ORGANISM: Unknown
<220> FEATURE:
<223> OTHER INFORMATION: The pattern is a combinatorial arrangement of
      pyknons in 3'UTRs.
<220> FEATURE:
<221> NAME/KEY: misc_feature
<223> OTHER INFORMATION: n indicates the number of nucleotides
      separating the pyknons that surround it, as specified by Figure
      11B.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (76)..(76)
<223> OTHER INFORMATION: n is a, c, g, or t
<220> FEATURE:
<221> NAME/KEY: misc_feature
<222> LOCATION: (95)..(95)
<223> OTHER INFORMATION: n is a, c, g, or t
<220> FEATURE:
<221> NAME/KEY: misc_feature
<222> LOCATION: (112)..(112)
<223> OTHER INFORMATION: n is a, c, g, or t
<220> FEATURE:
<221> NAME/KEY: misc_feature
<222> LOCATION: (129)..(129)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (165)..(165)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (216)..(216)
<223> OTHER INFORMATION: n is a, c, g, or t
<220> FEATURE:
```

```
<221> NAME/KEY: misc_feature
<222> LOCATION: (235)..(235)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (285)..(285)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (337)..(337)
<223> OTHER INFORMATION: n is a, c, g, or t
<220> FEATURE:
<221> NAME/KEY: misc_feature
<222> LOCATION: (355)..(355)
<223> OTHER INFORMATION: n is a, c, g, or t
<220> FEATURE:
<221> NAME/KEY: misc_feature
<222> LOCATION: (372)..(372)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (438)..(438)
<223> OTHER INFORMATION: n is a, c, g, or t
<220> FEATURE:
<221> NAME/KEY: misc_feature
<222> LOCATION: (456)..(456)
<223> OTHER INFORMATION: n is a, c, g, or t
<220> FEATURE:
<221> NAME/KEY: misc_feature
<222> LOCATION: (474)..(474)
<223> OTHER INFORMATION: n is a, c, g, or t
<220> FEATURE:
<221> NAME/KEY: misc_feature
<222> LOCATION: (507)..(507)
<223> OTHER INFORMATION: n is a, c, g, or t
<220> FEATURE:
<221> NAME/KEY: misc_feature
<222> LOCATION: (524)..(524)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (578)..(578)
<223> OTHER INFORMATION: n is a, c, g, or t
<220> FEATURE:
<221> NAME/KEY: misc_feature
<222> LOCATION: (595)..(595)
<223> OTHER INFORMATION: n is a, c, g, or t
<220> FEATURE:
<221> NAME/KEY: misc_feature
<222> LOCATION: (612)..(612)
<223> OTHER INFORMATION: n is a, c, g, or t
<220> FEATURE:
<221> NAME/KEY: misc_feature
<222> LOCATION: (629)..(629)
<223> OTHER INFORMATION: n is a, c, g, or t
<220> FEATURE:
<221> NAME/KEY: misc_feature
<222> LOCATION: (646)..(646)
<223> OTHER INFORMATION: n is a, c, g, or t
<220> FEATURE:
<221> NAME/KEY: misc_feature
<222> LOCATION: (664)..(664)
<223> OTHER INFORMATION: n is a, c, g, or t
<220> FEATURE:
```

-continued

```
<221> NAME/KEY: misc_feature
<222> LOCATION: (681)..(681)
<223> OTHER INFORMATION: n is a, c, g, or t
<220> FEATURE:
<221> NAME/KEY: misc_feature
<222> LOCATION: (698)..(698)
<223> OTHER INFORMATION: n is a, c, g, or t
<220> FEATURE:
<221> NAME/KEY: misc_feature
<222> LOCATION: (715)..(715)
<223> OTHER INFORMATION: n is a, c, g, or t
<220> FEATURE:
<221> NAME/KEY: misc_feature
<222> LOCATION: (732)..(732)
<223> OTHER INFORMATION: n is a, c, g, or t
<220> FEATURE:
<221> NAME/KEY: misc_feature
<222> LOCATION: (749)..(749)
<223> OTHER INFORMATION: n is a, c, g, or t
<220> FEATURE:
<221> NAME/KEY: misc_feature
<222> LOCATION: (769)..(769)
<223> OTHER INFORMATION: n is a, c, g, or t
<220> FEATURE:
<221> NAME/KEY: misc_feature
<222> LOCATION: (786)..(786)
<223> OTHER INFORMATION: n is a, c, g, or t
<220> FEATURE:
<221> NAME/KEY: misc_feature
<222> LOCATION: (803)..(803)
<223> OTHER INFORMATION: n is a, c, g, or t
<220> FEATURE:
<221> NAME/KEY: misc_feature
<222> LOCATION: (820)..(820)
<223> OTHER INFORMATION: n is a, c, g, or t
<220> FEATURE:
<221> NAME/KEY: misc_feature
<222> LOCATION: (837)..(837)
<223> OTHER INFORMATION: n is a, c, g, or t
<220> FEATURE:
<221> NAME/KEY: misc_feature
<222> LOCATION: (854)..(854)
<223> OTHER INFORMATION: n is a, c, g, or t
<220> FEATURE:
<221> NAME/KEY: misc_feature
<222> LOCATION: (871)..(871)
<223> OTHER INFORMATION: n is a, c, g, or t
<220> FEATURE:
<221> NAME/KEY: misc_feature
<222> LOCATION: (888)..(888)
<223> OTHER INFORMATION: n is a, c, g, or t
<220> FEATURE:
<221> NAME/KEY: misc_feature
<222> LOCATION: (905)..(905)
<223> OTHER INFORMATION: n is a, c, g, or t
<220> FEATURE:
<221> NAME/KEY: misc_feature
<222> LOCATION: (922)..(922)
<223> OTHER INFORMATION: n is a, c, g, or t
<220> FEATURE:
<221> NAME/KEY: misc_feature
<222> LOCATION: (942)..(942)
<223> OTHER INFORMATION: n is a, c, g, or t
<220> FEATURE:
<221> NAME/KEY: misc_feature
<222> LOCATION: (960)..(960)
<223> OTHER INFORMATION: n is a, c, g, or t
<220> FEATURE:
<221> NAME/KEY: misc_feature
<222> LOCATION: (979)..(979)
<223> OTHER INFORMATION: n is a, c, g, or t
<220> FEATURE:
<221> NAME/KEY: misc_feature
<222> LOCATION: (996)..(996)
<223> OTHER INFORMATION: n is a, c, g, or t
<220> FEATURE:
<221> NAME/KEY: misc_feature
<222> LOCATION: (1013)..(1013)
<223> OTHER INFORMATION: n is a, c, g, or t
<220> FEATURE:
```

<221> NAME/KEY: misc_feature
<222> LOCATION: (1030)..(1030)
<223> OTHER INFORMATION: n is a, c, g, or t
<220> FEATURE:
<221> NAME/KEY: misc_feature
<222> LOCATION: (1063)..(1063)
<223> OTHER INFORMATION: n is a, c, g, or t
<220> FEATURE:
<221> NAME/KEY: misc_feature
<222> LOCATION: (1080)..(1080)
<223> OTHER INFORMATION: n is a, c, g, or t
<220> FEATURE:
<221> NAME/KEY: misc_feature
<222> LOCATION: (1097)..(1097)
<223> OTHER INFORMATION: n is a, c, g, or t

<400> SEQUENCE: 22

```
ntgtcaccca gctggagntg gttggagcag gaggncagtg gctcacgcct angaagccga      60
ggcgggtgga tcaccnagac catcctggct aacanccctat ctctacaaaa anttagctgg     120
gtgtggtgnc tgtagtccca gctactnggc tgaggcagga gaatnaacct ctgcctccgg     180
gnccctgcctc agcgtcccna gtagcaggga ctacancgtg caccaccatg cccgngtatt   240
tttagtagag attggccagg ctggtctnaa ctcttgacct caagngccaa agtgctggga     300
ttataggcgt gagccaccgn ctgccaggac tgggttntgg ggacttgggg ggaancctct    360
ctgggctgca gnagtttcac tcttgttgcc caggctggag tgcangctca cctcaacctc    420
cgcctcccag gttcaagnat tctcctgcct cagccnagta gctgggatta cagnatgcct    480
ggctaatttt gtattttttag tagaganagc tggtctcgaa ctcnatctgc ccacttcggc   540
ctcccaaagt gctgggatta naggcatgag ccaccgcnga gacagagtct cactncccag    600
gttggagtgc anatctgagc tcactgcang cctcttgggt tcaagnattc tcctgcctca    660
gccnagtagc taggactaca ncaccatgcc cagctaangt attttttagta gaganttggc   720
caggctggtc tnacctaagg tgatccacnt cccaaagtgc tgggattant gagccatggc    780
acctgnggaa aggggtcagg gcnggaaact gaggcccagn ctctgcctct gggattngtg    840
ggcagcccag gagncatctg tgaaatggga ntgcctgggt ttgaatcntc tgtgccttca    900
tttcngctgg gattccaggc antaatccca gcactttggg angatcacga ggtcaggagn    960
agaccatcct agctaacana gtgaaaccct atctcnttag ctgggcatgg tgntgtagtc   1020
ccagatactn taaggcagaa gaatcgcttc aacctgggag gcngaggttg cagtgagccn  1080
tgcactccag cctgggn                                                 1097
```

<210> SEQ ID NO 23
<211> LENGTH: 425
<212> TYPE: DNA
<213> ORGANISM: Unknown
<220> FEATURE:
<223> OTHER INFORMATION: The pattern is a combinatorial arrangement of
      pyknons in 3'UTRs.
<220> FEATURE:
<221> NAME/KEY: misc_feature
<223> OTHER INFORMATION: n indicates the number of nucleotides
      separating the pyknons that surround it, as specified by Figure
      11B.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (55)..(55)

-continued

```
<223> OTHER INFORMATION: n is a, c, g, or t
<220> FEATURE:
<221> NAME/KEY: misc_feature
<222> LOCATION: (74)..(74)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (195)..(195)
<223> OTHER INFORMATION: n is a, c, g, or t
<220> FEATURE:
<221> NAME/KEY: misc_feature
<222> LOCATION: (212)..(212)
<223> OTHER INFORMATION: n is a, c, g, or t
<220> FEATURE:
<221> NAME/KEY: misc_feature
<222> LOCATION: (231)..(231)
<223> OTHER INFORMATION: n is a, c, g, or t
<220> FEATURE:
<221> NAME/KEY: misc_feature
<222> LOCATION: (252)..(252)
<223> OTHER INFORMATION: n is a, c, g, or t
<220> FEATURE:
<221> NAME/KEY: misc_feature
<222> LOCATION: (269)..(269)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:
<221> NAME/KEY: misc_feature
<222> LOCATION: (306)..(306)
<223> OTHER INFORMATION: n is a, c, g, or t
<220> FEATURE:
<221> NAME/KEY: misc_feature
<222> LOCATION: (323)..(323)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (374)..(374)
<223> OTHER INFORMATION: n is a, c, g, or t
<220> FEATURE:
<221> NAME/KEY: misc_feature
<222> LOCATION: (391)..(391)
<223> OTHER INFORMATION: n is a, c, g, or t
<220> FEATURE:
<221> NAME/KEY: misc_feature
<222> LOCATION: (408)..(408)
<223> OTHER INFORMATION: n is a, c, g, or t
<220> FEATURE:
<221> NAME/KEY: misc_feature
<222> LOCATION: (425)..(425)
<223> OTHER INFORMATION: n is a, c, g, or t

<400> SEQUENCE: 23
```

```
ncggtggctc acacctgtaa tcccagcact ttgggangat cacaaggtca ggagnagacc      60
atcctgtcta acanaaatta gtcggacatg nctgtagtcc cagctactng gctgaggcag     120
gagaatggcg tgaacccagg aggngagctt gcagtgagcc ntgcactcca gcctgggnga     180
cagagtgaga ctccncagtg gctcacgcct gncacattgg gaggctgagg natcacctga     240
ggtcaggagt tnagaccagc ctggccaanc tgtaatccca gctactngag gctgaggccg     300
gagaancttg agcccgagag gtnaagccaa gatcatgcca ntgcactcca gcctgggcaa     360
cacagggaga ctcntttgag aggcctaggc nttttcttg tagaggtnca aaaatgggca      420 aaatn                                                                 425
```

<210> SEQ ID NO 24
<211> LENGTH: 721
<212> TYPE: DNA
<213> ORGANISM: Unknown
<220> FEATURE:
<223> OTHER INFORMATION: The pattern is a combinatorial arrangement of
      pyknons in 3'UTRs.
<220> FEATURE:
<221> NAME/KEY: misc_feature
<223> OTHER INFORMATION: n indicates the number of nucleotides
      separating the pyknons that surround it, as specified by Figure
      11B.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (123)..(123)
<223> OTHER INFORMATION: n is a, c, g, or t
<220> FEATURE:
<221> NAME/KEY: misc_feature
<222> LOCATION: (141)..(141)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (209)..(209)
<223> OTHER INFORMATION: n is a, c, g, or t
<220> FEATURE:
<221> NAME/KEY: misc_feature
<222> LOCATION: (226)..(226)

-continued

```
<223> OTHER INFORMATION: n is a, c, g, or t
<220> FEATURE:
<221> NAME/KEY: misc_feature
<222> LOCATION: (246)..(246)
<223> OTHER INFORMATION: n is a, c, g, or t
<220> FEATURE:
<221> NAME/KEY: misc_feature
<222> LOCATION: (283)..(283)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (369)..(369)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (403)..(403)
<223> OTHER INFORMATION: n is a, c, g, or t
<220> FEATURE:
<221> NAME/KEY: misc_feature
<222> LOCATION: (420)..(420)
<223> OTHER INFORMATION: n is a, c, g, or t
<220> FEATURE:
<221> NAME/KEY: misc_feature
<222> LOCATION: (437)..(437)
<223> OTHER INFORMATION: n is a, c, g, or t
<220> FEATURE:
<221> NAME/KEY: misc_feature
<222> LOCATION: (454)..(454)
<223> OTHER INFORMATION: n is a, c, g, or t
<220> FEATURE:
<221> NAME/KEY: misc_feature
<222> LOCATION: (471)..(471)
<223> OTHER INFORMATION: n is a, c, g, or t
<220> FEATURE:
<221> NAME/KEY: misc_feature
<222> LOCATION: (488)..(488)
<223> OTHER INFORMATION: n is a, c, g, or t
<220> FEATURE:
<221> NAME/KEY: misc_feature
<222> LOCATION: (505)..(505)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t
<220> FEATURE:
<221> NAME/KEY: misc_feature
<222> LOCATION: (563)..(563)
<223> OTHER INFORMATION: n is a, c, g, or t
<220> FEATURE:
<221> NAME/KEY: misc_feature
<222> LOCATION: (580)..(580)
<223> OTHER INFORMATION: n is a, c, g, or t
<220> FEATURE:
<221> NAME/KEY: misc_feature
<222> LOCATION: (600)..(600)
```

-continued

<223> OTHER INFORMATION: n is a, c, g, or t
<220> FEATURE:
<221> NAME/KEY: misc_feature
<222> LOCATION: (618)..(618)
<223> OTHER INFORMATION: n is a, c, g, or t
<220> FEATURE:
<221> NAME/KEY: misc_feature
<222> LOCATION: (636)..(636)
<223> OTHER INFORMATION: n is a, c, g, or t
<220> FEATURE:
<221> NAME/KEY: misc_feature
<222> LOCATION: (654)..(654)
<223> OTHER INFORMATION: n is a, c, g, or t
<220> FEATURE:
<221> NAME/KEY: misc_feature
<222> LOCATION: (671)..(671)
<223> OTHER INFORMATION: n is a, c, g, or t
<220> FEATURE:
<221> NAME/KEY: misc_feature
<222> LOCATION: (688)..(688)
<223> OTHER INFORMATION: n is a, c, g, or t
<220> FEATURE:
<221> NAME/KEY: misc_feature
<222> LOCATION: (721)..(721)
<223> OTHER INFORMATION: n is a, c, g, or t

<400> SEQUENCE: 24 nttttgttt tgaggcntc gcccagggtg gagtnggctc attgcaacct cngcctcccg        60
gcttcaagnc tgctgcctca gcctcngagt agctgggata acaggtgtgg tggcgcatgc    120
ctncagctat tctggaggct ncttgaaccc aggaggtnga ggttgcagtg agccncaaca    180
agagcaaaac tnaagagatg acatttgant gcaaaggccc tgaggntaat cccagcactt    240 tgggana tca cctgaggtca ggagttagac cagcctggcc aanttagctg ggtgtggtgn    300
ctgtaatccc agatactngc tgaggcatga gaatncttga acctgggagg cntgcagtga    360
gctgagatnt gcactccagc ctgggntagc tgggcctggt ggntatagtc ccagctactn    420
gaggctaagg caggagnctg tgagctatga ttgntatact ccagcctggc ngcaagaccc    480
tgtctttnaa aaaaaatct aggcnggcac ggtggctcac gcctntaatc tcaacacttt     540
gnatcacctg aggtcaggag ttnagaccag actgaccaan tctctactaa aaacgcaaan    600
ttagccgggc gtggtggnct gtaatcccag ctactnggct gaggcaggag aatncttgaa    660
cccaggaggc ntgcagtgag ctgagatntg cactccagcc taggcaacaa gagtgaaact    720 n                                                                    721

<210> SEQ ID NO 25
<211> LENGTH: 830
<212> TYPE: DNA
<213> ORGANISM: Unknown
<220> FEATURE:
<223> OTHER INFORMATION: The pattern is a combinatorial arrangement of
      pyknons in 3'UTRs.
<220> FEATURE:
<221> NAME/KEY: misc_feature
<223> OTHER INFORMATION: n indicates the number of nucleotides
      separating the pyknons that surround it, as specified by Figure
      11B.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:

```
<221> NAME/KEY: misc_feature
<222> LOCATION: (71)..(71)
<223> OTHER INFORMATION: n is a, c, g, or t
<220> FEATURE:
<221> NAME/KEY: misc_feature
<222> LOCATION: (88)..(88)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (155)..(155)
<223> OTHER INFORMATION: n is a, c, g, or t
<220> FEATURE:
<221> NAME/KEY: misc_feature
<222> LOCATION: (172)..(172)
<223> OTHER INFORMATION: n is a, c, g, or t
<220> FEATURE:
<221> NAME/KEY: misc_feature
<222> LOCATION: (189)..(189)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (308)..(308)
<223> OTHER INFORMATION: n is a, c, g, or t
<220> FEATURE:
<221> NAME/KEY: misc_feature
<222> LOCATION: (325)..(325)
<223> OTHER INFORMATION: n is a, c, g, or t
<220> FEATURE:
<221> NAME/KEY: misc_feature
<222> LOCATION: (342)..(342)
<223> OTHER INFORMATION: n is a, c, g, or t
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (376)..(376)
<223> OTHER INFORMATION: n is a, c, g, or t
<220> FEATURE:
<221> NAME/KEY: misc_feature
<222> LOCATION: (394)..(394)
<223> OTHER INFORMATION: n is a, c, g, or t
<220> FEATURE:
<221> NAME/KEY: misc_feature
<222> LOCATION: (427)..(427)
<223> OTHER INFORMATION: n is a, c, g, or t
<220> FEATURE:
```

```
<221> NAME/KEY: misc_feature
<222> LOCATION: (444)..(444)
<223> OTHER INFORMATION: n is a, c, g, or t
<220> FEATURE:
<221> NAME/KEY: misc_feature
<222> LOCATION: (463)..(463)
<223> OTHER INFORMATION: n is a, c, g, or t
<220> FEATURE:
<221> NAME/KEY: misc_feature
<222> LOCATION: (480)..(480)
<223> OTHER INFORMATION: n is a, c, g, or t
<220> FEATURE:
<221> NAME/KEY: misc_feature
<222> LOCATION: (514)..(514)
<223> OTHER INFORMATION: n is a, c, g, or t
<220> FEATURE:
<221> NAME/KEY: misc_feature
<222> LOCATION: (531)..(531)
<223> OTHER INFORMATION: n is a, c, g, or t
<220> FEATURE:
<221> NAME/KEY: misc_feature
<222> LOCATION: (548)..(548)
<223> OTHER INFORMATION: n is a, c, g, or t
<220> FEATURE:
<221> NAME/KEY: misc_feature
<222> LOCATION: (565)..(565)
<223> OTHER INFORMATION: n is a, c, g, or t
<220> FEATURE:
<221> NAME/KEY: misc_feature
<222> LOCATION: (582)..(582)
<223> OTHER INFORMATION: n is a, c, g, or t
<220> FEATURE:
<221> NAME/KEY: misc_feature
<222> LOCATION: (599)..(599)
<223> OTHER INFORMATION: n is a, c, g, or t
<220> FEATURE:
<221> NAME/KEY: misc_feature
<222> LOCATION: (616)..(616)
<223> OTHER INFORMATION: n is a, c, g, or t
<220> FEATURE:
<221> NAME/KEY: misc_feature
<222> LOCATION: (633)..(633)
<223> OTHER INFORMATION: n is a, c, g, or t
<220> FEATURE:
<221> NAME/KEY: misc_feature
<222> LOCATION: (650)..(650)
<223> OTHER INFORMATION: n is a, c, g, or t
<220> FEATURE:
<221> NAME/KEY: misc_feature
<222> LOCATION: (670)..(670)
<223> OTHER INFORMATION: n is a, c, g, or t
<220> FEATURE:
<221> NAME/KEY: misc_feature
<222> LOCATION: (688)..(688)
<223> OTHER INFORMATION: n is a, c, g, or t
<220> FEATURE:
<221> NAME/KEY: misc_feature
<222> LOCATION: (707)..(707)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (742)..(742)
<223> OTHER INFORMATION: n is a, c, g, or t
<220> FEATURE:
<221> NAME/KEY: misc_feature
<222> LOCATION: (779)..(779)
<223> OTHER INFORMATION: n is a, c, g, or t
<220> FEATURE:
<221> NAME/KEY: misc_feature
<222> LOCATION: (796)..(796)
<223> OTHER INFORMATION: n is a, c, g, or t
<220> FEATURE:
<221> NAME/KEY: misc_feature
<222> LOCATION: (813)..(813)
<223> OTHER INFORMATION: n is a, c, g, or t
<220> FEATURE:
```

-continued

```
<221> NAME/KEY: misc_feature
<222> LOCATION: (830)..(830)
<223> OTHER INFORMATION: n is a, c, g, or t

<400> SEQUENCE: 25
ntcctctgtc tctgcctntt gaattttgta aaatncagtg gctcacacct gtaatcccag      60 cccctttggga nctgaggcag gtggattnct tgagcccagg agttnctcat ctctacaaaa    120
angtggtggc gtgtacctct agtcccagct acccnctagg ctgcagtgag cntgcactcc    180
agcctggtna cagtgaggcc ctgtcnaaaa aaaattttc tgnactgagc acttaaaatn    240
aaaatgttac tgaaatnatc atgttatttt tctnttggaa attattttaa nttttgttga    300
aagcaaanat attcactttt taaanataca tatttacata anatagaaac ttttaaaang    360
ggcatggtgg ctcacntaat cccagcactt tgtngaggtg ggcggatctc ctaaggtcag    420
gagttcnaga ccagcctggc caanatggtg aaaccccgtc ttnttagcca ggcgtggtgn    480
ctgtaatcct agctactcag gaggcaggaa aatncttgaa cctgggaggc ngaggttgca    540
gtgagccntg cactccagcc tgggngacag agtgagactc cntgagaata ttttaaatna    600
ttttattttc aagatntcat tccaatttta gtncaaaggc cgggcgcggn taatcccagc    660
actttgggan gatcacgagg tcaggagnag accatcctgg ctaacanatt agccaggcct    720
ggtnctgtag tcccagctac tngaggctga ggcaggagaa cggcgtgaac ccggagggng    780
agcttgcagt gagccntgca ctccagccta ggnggcagag ccagactccn              830

<210> SEQ ID NO 26
<211> LENGTH: 19
<212> TYPE: DNA
<213> ORGANISM: Unknown
<220> FEATURE:
<223> OTHER INFORMATION: The pattern is an example of a pyknon.

<400> SEQUENCE: 26
tcccaaagtg ctgggatta                                                  19

<210> SEQ ID NO 27
<211> LENGTH: 16
<212> TYPE: DNA
<213> ORGANISM: Unknown
<220> FEATURE:
<223> OTHER INFORMATION: The pattern is an example of a pyknon.

<400> SEQUENCE: 27
cccaggctgg agtgca                                                     16

<210> SEQ ID NO 28
<211> LENGTH: 17
<212> TYPE: DNA
<213> ORGANISM: Unknown
<220> FEATURE:
<223> OTHER INFORMATION: The pattern is an example of a pyknon.

<400> SEQUENCE: 28
agtagctggg attacag                                                    17

<210> SEQ ID NO 29
<211> LENGTH: 20
<212> TYPE: DNA
<213> ORGANISM: Unknown
<220> FEATURE:
<223> OTHER INFORMATION: The pattern is an example of a pyknon.

<400> SEQUENCE: 29
```
aactcctgac ctcaggtgat     20

<210> SEQ ID NO 30
<211> LENGTH: 1222
<212> TYPE: DNA
<213> ORGANISM: Homo sapiens
<220> FEATURE:
<221> NAME/KEY: misc_feature
<223> OTHER INFORMATION: n indicates a number of nucleotides that
      separate the surrounding pyknons, as specified in Figure 12.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (106)..(106)
<223> OTHER INFORMATION: n is a, c, g, or t
<220> FEATURE:
<221> NAME/KEY: misc_feature
<222> LOCATION: (124)..(124)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (178)..(178)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t
<220> FEATURE:
<221> NAME/KEY: misc_feature
<222> LOCATION: (219)..(219)
<223> OTHER INFORMATION: n is a, c, g, or t
<220> FEATURE:
<221> NAME/KEY: misc_feature
<222> LOCATION: (236)..(236)
<223> OTHER INFORMATION: n is a, c, g, or t
<220> FEATURE:
<221> NAME/KEY: misc_feature
<222> LOCATION: (253)..(253)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (287)..(287)
<223> OTHER INFORMATION: n is a, c, g, or t
<220> FEATURE:

-continued

```
<221> NAME/KEY: misc_feature
<222> LOCATION: (305)..(305)
<223> OTHER INFORMATION: n is a, c, g, or t
<220> FEATURE:
<221> NAME/KEY: misc_feature
<222> LOCATION: (346)..(346)
<223> OTHER INFORMATION: n is a, c, g, or t
<220> FEATURE:
<221> NAME/KEY: misc_feature
<222> LOCATION: (363)..(363)
<223> OTHER INFORMATION: n is a, c, g, or t
<220> FEATURE:
<221> NAME/KEY: misc_feature
<222> LOCATION: (380)..(380)
<223> OTHER INFORMATION: n is a, c, g, or t
<220> FEATURE:
<221> NAME/KEY: misc_feature
<222> LOCATION: (397)..(397)
<223> OTHER INFORMATION: n is a, c, g, or t
<220> FEATURE:
<221> NAME/KEY: misc_feature
<222> LOCATION: (414)..(414)
<223> OTHER INFORMATION: n is a, c, g, or t
<220> FEATURE:
<221> NAME/KEY: misc_feature
<222> LOCATION: (431)..(431)
<223> OTHER INFORMATION: n is a, c, g, or t
<220> FEATURE:
<221> NAME/KEY: misc_feature
<222> LOCATION: (466)..(466)
<223> OTHER INFORMATION: n is a, c, g, or t
<220> FEATURE:
<221> NAME/KEY: misc_feature
<222> LOCATION: (483)..(483)
<223> OTHER INFORMATION: n is a, c, g, or t
<220> FEATURE:
<221> NAME/KEY: misc_feature
<222> LOCATION: (500)..(500)
<223> OTHER INFORMATION: n is a, c, g, or t
<220> FEATURE:
<221> NAME/KEY: misc_feature
<222> LOCATION: (517)..(517)
<223> OTHER INFORMATION: n is a, c, g, or t
<220> FEATURE:
<221> NAME/KEY: misc_feature
<222> LOCATION: (536)..(536)
<223> OTHER INFORMATION: n is a, c, g, or t
<220> FEATURE:
<221> NAME/KEY: misc_feature
<222> LOCATION: (553)..(553)
<223> OTHER INFORMATION: n is a, c, g, or t
<220> FEATURE:
<221> NAME/KEY: misc_feature
<222> LOCATION: (570)..(570)
<223> OTHER INFORMATION: n is a, c, g, or t
<220> FEATURE:
<221> NAME/KEY: misc_feature
<222> LOCATION: (587)..(587)
<223> OTHER INFORMATION: n is a, c, g, or t
<220> FEATURE:
<221> NAME/KEY: misc_feature
<222> LOCATION: (608)..(608)
<223> OTHER INFORMATION: n is a, c, g, or t
<220> FEATURE:
<221> NAME/KEY: misc_feature
<222> LOCATION: (628)..(628)
<223> OTHER INFORMATION: n is a, c, g, or t
<220> FEATURE:
<221> NAME/KEY: misc_feature
<222> LOCATION: (645)..(645)
<223> OTHER INFORMATION: n is a, c, g, or t
<220> FEATURE:
<221> NAME/KEY: misc_feature
<222> LOCATION: (662)..(662)
<223> OTHER INFORMATION: n is a, c, g, or t
<220> FEATURE:
<221> NAME/KEY: misc_feature
<222> LOCATION: (679)..(679)
<223> OTHER INFORMATION: n is a, c, g, or t
<220> FEATURE:
```

```
<221> NAME/KEY: misc_feature
<222> LOCATION: (699)..(699)
<223> OTHER INFORMATION: n is a, c, g, or t
<220> FEATURE:
<221> NAME/KEY: misc_feature
<222> LOCATION: (718)..(718)
<223> OTHER INFORMATION: n is a, c, g, or t
<220> FEATURE:
<221> NAME/KEY: misc_feature
<222> LOCATION: (738)..(738)
<223> OTHER INFORMATION: n is a, c, g, or t
<220> FEATURE:
<221> NAME/KEY: misc_feature
<222> LOCATION: (756)..(756)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (792)..(792)
<223> OTHER INFORMATION: n is a, c, g, or t
<220> FEATURE:
<221> NAME/KEY: misc_feature
<222> LOCATION: (810)..(810)
<223> OTHER INFORMATION: n is a, c, g, or t
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (844)..(844)
<223> OTHER INFORMATION: n is a, c, g, or t
<220> FEATURE:
<221> NAME/KEY: misc_feature
<222> LOCATION: (863)..(863)
<223> OTHER INFORMATION: n is a, c, g, or t
<220> FEATURE:
<221> NAME/KEY: misc_feature
<222> LOCATION: (880)..(880)
<223> OTHER INFORMATION: n is a, c, g, or t
<220> FEATURE:
<221> NAME/KEY: misc_feature
<222> LOCATION: (897)..(897)
<223> OTHER INFORMATION: n is a, c, g, or t
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (932)..(932)
<223> OTHER INFORMATION: n is a, c, g, or t
<220> FEATURE:
<221> NAME/KEY: misc_feature
<222> LOCATION: (985)..(985)
<223> OTHER INFORMATION: n is a, c, g, or t
<220> FEATURE:
<221> NAME/KEY: misc_feature
<222> LOCATION: (1005)..(1005)
<223> OTHER INFORMATION: n is a, c, g, or t
<220> FEATURE:
<221> NAME/KEY: misc_feature
<222> LOCATION: (1022)..(1022)
<223> OTHER INFORMATION: n is a, c, g, or t
<220> FEATURE:
<221> NAME/KEY: misc_feature
<222> LOCATION: (1039)..(1039)
<223> OTHER INFORMATION: n is a, c, g, or t
<220> FEATURE:
<221> NAME/KEY: misc_feature
<222> LOCATION: (1060)..(1060)
<223> OTHER INFORMATION: n is a, c, g, or t
<220> FEATURE:
<221> NAME/KEY: misc_feature
<222> LOCATION: (1081)..(1081)
<223> OTHER INFORMATION: n is a, c, g, or t
<220> FEATURE:
```

```
<221> NAME/KEY: misc_feature
<222> LOCATION: (1098)..(1098)
<223> OTHER INFORMATION: n is a, c, g, or t
<220> FEATURE:
<221> NAME/KEY: misc_feature
<222> LOCATION: (1133)..(1133)
<223> OTHER INFORMATION: n is a, c, g, or t
<220> FEATURE:
<221> NAME/KEY: misc_feature
<222> LOCATION: (1150)..(1150)
<223> OTHER INFORMATION: n is a, c, g, or t
<220> FEATURE:
<221> NAME/KEY: misc_feature
<222> LOCATION: (1170)..(1170)
<223> OTHER INFORMATION: n is a, c, g, or t
<220> FEATURE:
<221> NAME/KEY: misc_feature
<222> LOCATION: (1187)..(1187)
<223> OTHER INFORMATION: n is a, c, g, or t
<220> FEATURE:
<221> NAME/KEY: misc_feature
<222> LOCATION: (1204)..(1204)
<223> OTHER INFORMATION: n is a, c, g, or t
<220> FEATURE:
<221> NAME/KEY: misc_feature
<222> LOCATION: (1222)..(1222)
<223> OTHER INFORMATION: n is a, c, g, or t

<400> SEQUENCE: 30
ntttcttcat tcattcanga cagtctcgct ctgtnccag gctggagtgc anatctcagc      60
tcactgcang ccttccaggt tcaagnagtc tcctgcctca gcctcnagta gctgggatta    120
cagnaccacg cctggctaat tncatttta gtagagacgn cttcaccatg ttggccanaa     180
ctcctgacct caggtaatnt cccaaagtgc tgagattang tgagctaccg tgcccnggtg    240
gtcagggaag gcnaggcagg aggaacagcn ttcattcaac aaatatnttg cccaggctgg    300
agttnagctc actgcaacct ccacctccca gattcaagtg attctnaata gctgggacta    360
canatgtcac catgcccagn ttggccaggc tggtctnaac tcctggcctc aaanaatcta    420
cctgccttgg ntccaaagtg ctaggattac aggtgtgagc caccgnccca ggctggagtg    480
canggctcat tgcaacctcn acctcccggg ttcaagntca gcttcctgag tagctntaca    540
ggcacttgcc acngacaggg ttttgccatn ttggccaggc tggtctnaac tcctgacctc    600
aggtgatntc ccaaagtgct ggcattangg cttgagccac cacgnggagt ctcgctctgt    660
cngctggagt gcagtgacnt gatctcggct cactgcagnc tccgccttct gggttcanat    720
tctcctgcct cagcctcnag tagctgggac tacagnccac ctcgcctggc tantgttagc    780
caggatggtc tnctcgtgac ctcgtgatcn ccagcctcgg cctcccntga gatggagttt    840
cgcntcaggc tggagtgcaa tgnatctcag ctcactgcan gcctcccagg ttcaagnatt    900
ctcccacctc agcnagtagc tgggattaca gnggggtttc actatgttgg ccaagctggt    960
cttgaactcc tgacctcagg tgatntccca aagtgctggg attantggag gtagggcctg   1020
gntgaatgaa agaatgaant ttgggaggcc aaggtgggtn atcacctgag gtcaggagtt   1080
nagaccagcc tggccaancc tctactaaaa atacaaaaaa ttagctgggc gtntgcctgt   1140
aatcacagcn gaggctgagg caggagaatn gaggttgcag tgagccntgc cattgcactc   1200
cagnggcaac agagcgagac tn                                            1222

<210> SEQ ID NO 31
<211> LENGTH: 451
<212> TYPE: DNA
<213> ORGANISM: Unknown
<220> FEATURE:
<223> OTHER INFORMATION: The pattern is a 5'UTR mosaic composed of
      pyknons.
```

```
<220> FEATURE:
<221> NAME/KEY: misc_feature
<223> OTHER INFORMATION: n indicates a number of nucleotides that
      separate the surrounding pyknons, as specified in Figure 12.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (174)..(174)
<223> OTHER INFORMATION: n is a, c, g, or t
<220> FEATURE:
<221> NAME/KEY: misc_feature
<222> LOCATION: (191)..(191)
<223> OTHER INFORMATION: n is a, c, g, or t
<220> FEATURE:
<221> NAME/KEY: misc_feature
<222> LOCATION: (208)..(208)
<223> OTHER INFORMATION: n is a, c, g, or t
<220> FEATURE:
<221> NAME/KEY: misc_feature
<222> LOCATION: (225)..(225)
<223> OTHER INFORMATION: n is a, c, g, or t
<220> FEATURE:
<221> NAME/KEY: misc_feature
<222> LOCATION: (242)..(242)
<223> OTHER INFORMATION: n is a, c, g, or t
<220> FEATURE:
<221> NAME/KEY: misc_feature
<222> LOCATION: (259)..(259)
<223> OTHER INFORMATION: n is a, c, g, or t
<220> FEATURE:
<221> NAME/KEY: misc_feature
<222> LOCATION: (292)..(292)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (327)..(327)
<223> OTHER INFORMATION: n is a, c, g, or t
<220> FEATURE:
<221> NAME/KEY: misc_feature
<222> LOCATION: (344)..(344)
<223> OTHER INFORMATION: n is a, c, g, or t
```

```
<220> FEATURE:
<221> NAME/KEY: misc_feature
<222> LOCATION: (361)..(361)
<223> OTHER INFORMATION: n is a, c, g, or t
<220> FEATURE:
<221> NAME/KEY: misc_feature
<222> LOCATION: (382)..(382)
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (451)..(451)
<223> OTHER INFORMATION: n is a, c, g, or t

<400> SEQUENCE: 31
ngagtcttgc tctgttgnga ggctggagtg cagtgatctc agctcactgg angcctcctg      60
ggttcaagnt ctcaacctcc caagtntgcc accacacctg ccnttttag tagggatggn     120 ttgggcaggc tggtctnaac tcctgacctc aagntcccag agtgctggga ttantgagcc    180
accatgcctg ncctgtctct aaaacaanca gaaattttct ttttngagac agagtcttac    240
tntcgctcag gctggagtna tctcagctca ctgcaacctc tgcctcctgg tnctccttcc    300
tcagcctcna gtagctggga ttacacncca ccgcgcctgg ctanttggcc aggctggtct    360
naactcctga cctcaggtga tnagcctccc aaaatgctnc aggcatgagc caccgnctca    420
gtttcttcat ttngggttg ctgccagctg n                                    451

<210> SEQ ID NO 32
<211> LENGTH: 402
<212> TYPE: DNA
<213> ORGANISM: Unknown
<220> FEATURE:
<223> OTHER INFORMATION: The pattern is a 5'UTR mosaic composed of
      pyknons.
<220> FEATURE:
<221> NAME/KEY: misc_feature
<223> OTHER INFORMATION: n indicates a number of nucleotides that
      separate the surrounding pyknons, as specified in Figure 12.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (54)..(54)
<223> OTHER INFORMATION: n is a, c, g, or t
<220> FEATURE:
<221> NAME/KEY: misc_feature
<222> LOCATION: (72)..(72)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
```

<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (142)..(142)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (193)..(193)
<223> OTHER INFORMATION: n is a, c, g, or t
<220> FEATURE:
<221> NAME/KEY: misc_feature
<222> LOCATION: (210)..(210)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (248)..(248)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (298)..(298)
<223> OTHER INFORMATION: n is a, c, g, or t
<220> FEATURE:
<221> NAME/KEY: misc_feature
<222> LOCATION: (315)..(315)
<223> OTHER INFORMATION: n is a, c, g, or t
<220> FEATURE:
<221> NAME/KEY: misc_feature
<222> LOCATION: (332)..(332)
<223> OTHER INFORMATION: n is a, c, g, or t
<220> FEATURE:
<221> NAME/KEY: misc_feature
<222> LOCATION: (368)..(368)
<223> OTHER INFORMATION: n is a, c, g, or t
<220> FEATURE:
<221> NAME/KEY: misc_feature
<222> LOCATION: (385)..(385)
<223> OTHER INFORMATION: n is a, c, g, or t
<220> FEATURE:
<221> NAME/KEY: misc_feature
<222> LOCATION: (402)..(402)
<223> OTHER INFORMATION: n is a, c, g, or t

<400> SEQUENCE: 32

```
ntgctgggat tacaggcgcn accacgcccg gctaatnggg tttcactgtg ttgnaggatg      60
gtctctatct cngtgatatg cccgcctcnt cccaaagtgc tgggattaca ggcttgagcc     120
accgnggcct atttatttat tngagacgga gtgttgctnc ccaggctgga gtgcanggct     180
cactgcaacc tcngcctccc gggttcaagn attctcctgc ctcagcctcn agtagctggg     240
attacagnac acccggctaa ttttgtattt ttagtagaaa ngggtttctc catgttgnct     300
ggtttcgaac tccngtcat ctgcctgcct cntcccaaag tgctgggatt acaggcgtga     360
gccaccgntc tgtatttta aaaantaaat gatttgccca an                        402
```

<210> SEQ ID NO 33
<211> LENGTH: 550
<212> TYPE: DNA

-continued

```
<213> ORGANISM: Unknown
<220> FEATURE:
<223> OTHER INFORMATION: The pattern is a 5'UTR mosaic composed of
      pyknons.
<220> FEATURE:
<221> NAME/KEY: misc_feature
<223> OTHER INFORMATION: n indicates a number of nucleotides that
      separate the surrounding pyknons, as specificed in Figure 12.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (140)..(140)
<223> OTHER INFORMATION: n is a, c, g, or t
<220> FEATURE:
<221> NAME/KEY: misc_feature
<222> LOCATION: (158)..(158)
<223> OTHER INFORMATION: n is a, c, g, or t
<220> FEATURE:
<221> NAME/KEY: misc_feature
<222> LOCATION: (175)..(175)
<223> OTHER INFORMATION: n is a, c, g, or t
<220> FEATURE:
<221> NAME/KEY: misc_feature
<222> LOCATION: (192)..(192)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (233)..(233)
<223> OTHER INFORMATION: n is a, c, g, or t
<220> FEATURE:
<221> NAME/KEY: misc_feature
<222> LOCATION: (250)..(250)
<223> OTHER INFORMATION: n is a, c, g, or t
<220> FEATURE:
<221> NAME/KEY: misc_feature
<222> LOCATION: (267)..(267)
<223> OTHER INFORMATION: n is a, c, g, or t
<220> FEATURE:
<221> NAME/KEY: misc_feature
<222> LOCATION: (284)..(284)
<223> OTHER INFORMATION: n is a, c, g, or t
<220> FEATURE:
<221> NAME/KEY: misc_feature
<222> LOCATION: (301)..(301)
<223> OTHER INFORMATION: n is a, c, g, or t
```

```
<220> FEATURE:
<221> NAME/KEY: misc_feature
<222> LOCATION: (318)..(318)
<223> OTHER INFORMATION: n is a, c, g, or t
<220> FEATURE:
<221> NAME/KEY: misc_feature
<222> LOCATION: (335)..(335)
<223> OTHER INFORMATION: n is a, c, g, or t
<220> FEATURE:
<221> NAME/KEY: misc_feature
<222> LOCATION: (352)..(352)
<223> OTHER INFORMATION: n is a, c, g, or t
<220> FEATURE:
<221> NAME/KEY: misc_feature
<222> LOCATION: (370)..(370)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (404)..(404)
<223> OTHER INFORMATION: n is a, c, g, or t
<220> FEATURE:
<221> NAME/KEY: misc_feature
<222> LOCATION: (421)..(421)
<223> OTHER INFORMATION: n is a, c, g, or t
<220> FEATURE:
<221> NAME/KEY: misc_feature
<222> LOCATION: (439)..(439)
<223> OTHER INFORMATION: n is a, c, g, or t
<220> FEATURE:
<221> NAME/KEY: misc_feature
<222> LOCATION: (460)..(460)
<223> OTHER INFORMATION: n is a, c, g, or t
<220> FEATURE:
<221> NAME/KEY: misc_feature
<222> LOCATION: (478)..(478)
<223> OTHER INFORMATION: n is a, c, g, or t
<220> FEATURE:
<221> NAME/KEY: misc_feature
<222> LOCATION: (495)..(495)
<223> OTHER INFORMATION: n is a, c, g, or t
<220> FEATURE:
<221> NAME/KEY: misc_feature
<222> LOCATION: (512)..(512)
<223> OTHER INFORMATION: n is a, c, g, or t
<220> FEATURE:
<221> NAME/KEY: misc_feature
<222> LOCATION: (534)..(534)
<223> OTHER INFORMATION: n is a, c, g, or t

<400> SEQUENCE: 33
nacaacaccc aagtcctngc ctgagtgcag tggcnttctt caaagaagaa antttgagac      60
agagtctcnc ccaggctgga gtgcanggct cactacaacc tcngcctccc aggttcaaan    120
attctcctgc ctcagcctcn agtagctggg attacagnat agagatgggg tttcnttggc    180
caggctggtc tnaactcctg acctcaggtg atntcccaaa gtgctggat tancaccaca     240 cccagccatn attatgtttt ctaaaancag actctgcctc aaangagtct tgctctgttg    300
ncgctggagt gcagtggngg ctcactgcaa cctcngctcc caggttcaag cnagtagctg    360
ggactacagn acatccggct aattttnata gagacggggt tttnttggcc aggatggtct    420
nctcctgacc tcatgatcna gcctcccaaa gtgctggggn aggcatgagc cacccacgngt   480 cttgctctgt caccntgcag ccttgaactc cncctcctgc ctcagcctcc cganacaggt    540
atgtaccacc                                                           550

<210> SEQ ID NO 34
<211> LENGTH: 475
<212> TYPE: DNA
<213> ORGANISM: Unknown
```

-continued

```
<220> FEATURE:
<223> OTHER INFORMATION: The pattern is a 5'UTR mosaic composed of
      pyknons.
<220> FEATURE:
<221> NAME/KEY: misc_feature
<223> OTHER INFORMATION: n indicates a number of nucleotides that
      separate the surrounding pyknons, as specificed in Figure 12.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (89)..(89)
<223> OTHER INFORMATION: n is a, c, g, or t
<220> FEATURE:
<221> NAME/KEY: misc_feature
<222> LOCATION: (109)..(109)
<223> OTHER INFORMATION: n is a, c, g, or t
<220> FEATURE:
<221> NAME/KEY: misc_feature
<222> LOCATION: (127)..(127)
<223> OTHER INFORMATION: n is a, c, g, or t
<220> FEATURE:
<221> NAME/KEY: misc_feature
<222> LOCATION: (144)..(144)
<223> OTHER INFORMATION: n is a, c, g, or t
<220> FEATURE:
<221> NAME/KEY: misc_feature
<222> LOCATION: (161)..(161)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (218)..(218)
<223> OTHER INFORMATION: n is a, c, g, or t
<220> FEATURE:
<221> NAME/KEY: misc_feature
<222> LOCATION: (251)..(251)
<223> OTHER INFORMATION: n is a, c, g, or t
<220> FEATURE:
<221> NAME/KEY: misc_feature
<222> LOCATION: (268)..(268)
<223> OTHER INFORMATION: n is a, c, g, or t
<220> FEATURE:
<221> NAME/KEY: misc_feature
<222> LOCATION: (286)..(286)
<223> OTHER INFORMATION: n is a, c, g, or t
<220> FEATURE:
<221> NAME/KEY: misc_feature
<222> LOCATION: (303)..(303)
<223> OTHER INFORMATION: n is a, c, g, or t
<220> FEATURE:
<221> NAME/KEY: misc_feature
<222> LOCATION: (320)..(320)
<223> OTHER INFORMATION: n is a, c, g, or t
<220> FEATURE:
<221> NAME/KEY: misc_feature
<222> LOCATION: (353)..(353)
<223> OTHER INFORMATION: n is a, c, g, or t
<220> FEATURE:
<221> NAME/KEY: misc_feature
<222> LOCATION: (371)..(371)
<223> OTHER INFORMATION: n is a, c, g, or t
<220> FEATURE:
```

```
<221> NAME/KEY: misc_feature
<222> LOCATION: (390)..(390)
<223> OTHER INFORMATION: n is a, c, g, or t
<220> FEATURE:
<221> NAME/KEY: misc_feature
<222> LOCATION: (407)..(407)
<223> OTHER INFORMATION: n is a, c, g, or t
<220> FEATURE:
<221> NAME/KEY: misc_feature
<222> LOCATION: (424)..(424)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t

<400> SEQUENCE: 34
nagagtcttg ctctgtcgcc caggctggag tgcanggctc actgcaacct cngcctccca      60
ggttcaagna ttctcctgcc tcagcctcnt gtagctggga ttacaggcnc accatgcccg     120
gctaatntta tttttagtag aganttggcc aggctggtct naactcctga cctcaggtga     180
tntcccaaag tgctgggatt acaggcgtga gccaccgntg gtcttgctgt gtcacccagg     240
ctggagtgca ntcttgaatt cctgggcnaa gcctcccaag tagctncagg cacatactac     300
cantttttgt agagacaggn ttactatgtt gcccagactg gtcttgaact ccnattacag     360
gtgtgagcct ngtttttttg agacagggtn cccaggctgg agtgcanggc tcactgcagc     420
ctcncctccc aaggctcagg natcctcttg cctcagcnac caagtagctg ggacn          475

<210> SEQ ID NO 35
<211> LENGTH: 199
<212> TYPE: DNA
<213> ORGANISM: Unknown
<220> FEATURE:
<223> OTHER INFORMATION: The pattern is a 5'UTR mosaic composed of
      pyknons.
<220> FEATURE:
<221> NAME/KEY: misc_feature
<223> OTHER INFORMATION: n indicates a number of nucleotides that
      separate the surrounding pyknons, as specified in Figure 12.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (73)..(73)
<223> OTHER INFORMATION: n is a, c, g, or t
<220> FEATURE:
<221> NAME/KEY: misc_feature
<222> LOCATION: (91)..(91)
<223> OTHER INFORMATION: n is a, c, g, or t
<220> FEATURE:
<221> NAME/KEY: misc_feature
```

```
<222> LOCATION: (108)..(108)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (146)..(146)
<223> OTHER INFORMATION: n is a, c, g, or t
<220> FEATURE:
<221> NAME/KEY: misc_feature
<222> LOCATION: (182)..(182)
<223> OTHER INFORMATION: n is a, c, g, or t
<220> FEATURE:
<221> NAME/KEY: misc_feature
<222> LOCATION: (199)..(199)
<223> OTHER INFORMATION: n is a, c, g, or t

<400> SEQUENCE: 35
nggctggagg gcagaggncc caggctggag tgcangatct cggctcactg cgnattctcc      60
tgcctcagcc tcnagtagct gggattacag nccatcacgc ccggctantt ggtcaggcta     120
gtctnaactc ctgacctcag gtgatntccc aaagtgctgg gattacaggc gtgagccacc     180
gngcagagac tggagggan                                                  199

<210> SEQ ID NO 36
<211> LENGTH: 506
<212> TYPE: DNA
<213> ORGANISM: Unknown
<220> FEATURE:
<223> OTHER INFORMATION: The pattern is a 5'UTR mosaic composed of
      pyknons.
<220> FEATURE:
<221> NAME/KEY: misc_feature
<223> OTHER INFORMATION: n indicates a number of nucleotides that
      separate the surrounding pyknons, as specified in Figure 12.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (53)..(53)
<223> OTHER INFORMATION: n is a, c, g, or t
<220> FEATURE:
<221> NAME/KEY: misc_feature
<222> LOCATION: (105)..(105)
<223> OTHER INFORMATION: n is a, c, g, or t
<220> FEATURE:
<221> NAME/KEY: misc_feature
<222> LOCATION: (122)..(122)
<223> OTHER INFORMATION: n is a, c, g, or t
<220> FEATURE:
<221> NAME/KEY: misc_feature
<222> LOCATION: (143)..(143)
<223> OTHER INFORMATION: n is a, c, g, or t
<220> FEATURE:
<221> NAME/KEY: misc_feature
<222> LOCATION: (160)..(160)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (247)..(247)
```

```
<223> OTHER INFORMATION: n is a, c, g, or t
<220> FEATURE:
<221> NAME/KEY: misc_feature
<222> LOCATION: (280)..(280)
<223> OTHER INFORMATION: n is a, c, g, or t
<220> FEATURE:
<221> NAME/KEY: misc_feature
<222> LOCATION: (297)..(297)
<223> OTHER INFORMATION: n is a, c, g, or t
<220> FEATURE:
<221> NAME/KEY: misc_feature
<222> LOCATION: (314)..(314)
<223> OTHER INFORMATION: n is a, c, g, or t
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (349)..(349)
<223> OTHER INFORMATION: n is a, c, g, or t
<220> FEATURE:
<221> NAME/KEY: misc_feature
<222> LOCATION: (366)..(366)
<223> OTHER INFORMATION: n is a, c, g, or t
<220> FEATURE:
<221> NAME/KEY: misc_feature
<222> LOCATION: (383)..(383)
<223> OTHER INFORMATION: n is a, c, g, or t
<220> FEATURE:
<221> NAME/KEY: misc_feature
<222> LOCATION: (400)..(400)
<223> OTHER INFORMATION: n is a, c, g, or t
<220> FEATURE:
<221> NAME/KEY: misc_feature
<222> LOCATION: (419)..(419)
<223> OTHER INFORMATION: n is a, c, g, or t
<220> FEATURE:
<221> NAME/KEY: misc_feature
<222> LOCATION: (455)..(455)
<223> OTHER INFORMATION: n is a, c, g, or t
<220> FEATURE:
<221> NAME/KEY: misc_feature
<222> LOCATION: (472)..(472)
<223> OTHER INFORMATION: n is a, c, g, or t
<220> FEATURE:
<221> NAME/KEY: misc_feature
<222> LOCATION: (489)..(489)
<223> OTHER INFORMATION: n is a, c, g, or t
<220> FEATURE:
<221> NAME/KEY: misc_feature
<222> LOCATION: (506)..(506)
<223> OTHER INFORMATION: n is a, c, g, or t

<400> SEQUENCE: 36
ntctgttgcc aggctggagt gccgtggtgt gatctcggct cactgcaacc tcnctctcag      60
gttcaagcga ttctcctgcc tcagcctcct cagtagctgg gattnaggca tgcactacca     120
tntagagatg gggtttcacc acnttgccca ggctggtctn aactcctgac ctcaacntcc     180
caaagtgctg ggattacagg cgtgagccac cgncccggcc tgatttttn ctggataaag      240 agaatgngag tcttgctctg ttgctcaggc tggagtgcan gatctcagct cattgcngcc     300
ccccaggttc aagnttcctg cctcagcctc nagtagctgg gattacagna cacctggcta     360
attttnattt tagtagagat ggnttggcca ggatggtctn cctcaagtga tctgcctgnt     420
cccaaagtgc taggattaca ggtgtgagcc atcantttcc ttatctgtaa angaatgact     480
ttggggtant tctttctttt ccatgn                                          506

<210> SEQ ID NO 37
<211> LENGTH: 542
<212> TYPE: DNA
<213> ORGANISM: Unknown
<220> FEATURE:
```

-continued

```
<223> OTHER INFORMATION: The pattern is a 5'UTR mosaic composed of
      pyknons.
<220> FEATURE:
<221> NAME/KEY: misc_feature
<223> OTHER INFORMATION: n indicates a number of nucleotides that
      separate the surrounding pyknons, as specified in Figure 12.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (51)..(51)
<223> OTHER INFORMATION: n is a, c, g, or t
<220> FEATURE:
<221> NAME/KEY: misc_feature
<222> LOCATION: (68)..(68)
<223> OTHER INFORMATION: n is a, c, g, or t
<220> FEATURE:
<221> NAME/KEY: misc_feature
<222> LOCATION: (85)..(85)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (121)..(121)
<223> OTHER INFORMATION: n is a, c, g, or t
<220> FEATURE:
<221> NAME/KEY: misc_feature
<222> LOCATION: (138)..(138)
<223> OTHER INFORMATION: n is a, c, g, or t
<220> FEATURE:
<221> NAME/KEY: misc_feature
<222> LOCATION: (159)..(159)
<223> OTHER INFORMATION: n is a, c, g, or t
<220> FEATURE:
<221> NAME/KEY: misc_feature
<222> LOCATION: (176)..(176)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t
<220> FEATURE:
<221> NAME/KEY: misc_feature
<222> LOCATION: (230)..(230)
<223> OTHER INFORMATION: n is a, c, g, or t
<220> FEATURE:
<221> NAME/KEY: misc_feature
<222> LOCATION: (247)..(247)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (281)..(281)
<223> OTHER INFORMATION: n is a, c, g, or t
<220> FEATURE:
<221> NAME/KEY: misc_feature
<222> LOCATION: (300)..(300)
<223> OTHER INFORMATION: n is a, c, g, or t
<220> FEATURE:
<221> NAME/KEY: misc_feature
<222> LOCATION: (317)..(317)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
```

<222> LOCATION: (368)..(368)
<223> OTHER INFORMATION: n is a, c, g, or t
<220> FEATURE:
<221> NAME/KEY: misc_feature
<222> LOCATION: (387)..(387)
<223> OTHER INFORMATION: n is a, c, g, or t
<220> FEATURE:
<221> NAME/KEY: misc_feature
<222> LOCATION: (405)..(405)
<223> OTHER INFORMATION: n is a, c, g, or t
<220> FEATURE:
<221> NAME/KEY: misc_feature
<222> LOCATION: (441)..(441)
<223> OTHER INFORMATION: n is a, c, g, or t
<220> FEATURE:
<221> NAME/KEY: misc_feature
<222> LOCATION: (458)..(458)
<223> OTHER INFORMATION: n is a, c, g, or t
<220> FEATURE:
<221> NAME/KEY: misc_feature
<222> LOCATION: (491)..(491)
<223> OTHER INFORMATION: n is a, c, g, or t
<220> FEATURE:
<221> NAME/KEY: misc_feature
<222> LOCATION: (508)..(508)
<223> OTHER INFORMATION: n is a, c, g, or t
<220> FEATURE:
<221> NAME/KEY: misc_feature
<222> LOCATION: (525)..(525)
<223> OTHER INFORMATION: n is a, c, g, or t
<220> FEATURE:
<221> NAME/KEY: misc_feature
<222> LOCATION: (542)..(542)
<223> OTHER INFORMATION: n is a, c, g, or t

<400> SEQUENCE: 37

```
nacatatttt aaattctnga gtcttgctct gttgcccagg ctggagtgca ngtctcagct   60
cactgcangc ctcttgggtt caagntccta cctcagcctc ctnagtagct gggattacag  120
ntaccaccat gtccagcntt ttactagaga tggggttnt tggccaggct ggtctnctcc   180
tgacctcatg atcntcccaa agtgctggga ttacaggcat gagccaccgn gaatgggcaa  240
aagctgngtc ttgctctgtc accnaggcta gagtgcagtg nttcagctca ctgcaacctn  300
gcctcccggg ttcaagngcc tccacctcct gagcagctgg gattacaggn caccatgccc  360
ggctaatntg ttagccagga ttgtctnctc ttgacctcgt gatcntccca aagtgctggg  420
attacaggcg tgagccactg ncaatgtttt acagtttnct caaggttaca cagcgagtgt  480
gtgtgagaga naacccagga ggttgaanat ctgaccttc tctcntgtgc caggcccagg  540
gn                                                                 542
```

<210> SEQ ID NO 38
<211> LENGTH: 467
<212> TYPE: DNA
<213> ORGANISM: Unknown
<220> FEATURE:
<223> OTHER INFORMATION: The pattern is a 5'UTR mosaic composed of
      pyknons.
<220> FEATURE:
<221> NAME/KEY: misc_feature
<223> OTHER INFORMATION: n indicates a number of nucleotides that
      separate the surrounding pyknons, as specified in Figure 12.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)

-continued

```
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (206)..(206)
<223> OTHER INFORMATION: n is a, c, g, or t
<220> FEATURE:
<221> NAME/KEY: misc_feature
<222> LOCATION: (223)..(223)
<223> OTHER INFORMATION: n is a, c, g, or t
<220> FEATURE:
<221> NAME/KEY: misc_feature
<222> LOCATION: (240)..(240)
<223> OTHER INFORMATION: n is a, c, g, or t
<220> FEATURE:
<221> NAME/KEY: misc_feature
<222> LOCATION: (257)..(257)
<223> OTHER INFORMATION: n is a, c, g, or t
<220> FEATURE:
<221> NAME/KEY: misc_feature
<222> LOCATION: (274)..(274)
<223> OTHER INFORMATION: n is a, c, g, or t
<220> FEATURE:
<221> NAME/KEY: misc_feature
<222> LOCATION: (291)..(291)
<223> OTHER INFORMATION: n is a, c, g, or t
<220> FEATURE:
<221> NAME/KEY: misc_feature
<222> LOCATION: (309)..(309)
<223> OTHER INFORMATION: n is a, c, g, or t
<220> FEATURE:
<221> NAME/KEY: misc_feature
<222> LOCATION: (328)..(328)
<223> OTHER INFORMATION: n is a, c, g, or t
<220> FEATURE:
<221> NAME/KEY: misc_feature
<222> LOCATION: (345)..(345)
<223> OTHER INFORMATION: n is a, c, g, or t
<220> FEATURE:
<221> NAME/KEY: misc_feature
<222> LOCATION: (362)..(362)
<223> OTHER INFORMATION: n is a, c, g, or t
<220> FEATURE:
<221> NAME/KEY: misc_feature
<222> LOCATION: (379)..(379)
```

```
<223> OTHER INFORMATION: n is a, c, g, or t
<220> FEATURE:
<221> NAME/KEY: misc_feature
<222> LOCATION: (399)..(399)
<223> OTHER INFORMATION: n is a, c, g, or t
<220> FEATURE:
<221> NAME/KEY: misc_feature
<222> LOCATION: (416)..(416)
<223> OTHER INFORMATION: n is a, c, g, or t
<220> FEATURE:
<221> NAME/KEY: misc_feature
<222> LOCATION: (433)..(433)
<223> OTHER INFORMATION: n is a, c, g, or t
<220> FEATURE:
<221> NAME/KEY: misc_feature
<222> LOCATION: (450)..(450)
<223> OTHER INFORMATION: n is a, c, g, or t
<220> FEATURE:
<221> NAME/KEY: misc_feature
<222> LOCATION: (467)..(467)
<223> OTHER INFORMATION: n is a, c, g, or t

<400> SEQUENCE: 38
nttgtcgccc acgctggnat ctcagttcac tgcangcctc ccaggttcaa gntgcctcag      60
cttcccgana gctaggacta caggtnacgc tcagctaatt ttngatgggg ttttcccatn     120
ttggccaggc tggtctnaac tcctgacctc agancaggcg tgagccactg nacattttgg    180 tatgttntg aacaggcaac ttacanaata atattttctt cantgctgga gtgcaatggn     240
ggctcactgc aacctcngcc tcctgggttc aggnctcctg cctcagactc nagtagctgg    300
gattacagng cctgccacca cgcccggngt gtttcactat gttgngggct ggtctcgaac    360
tnctgccctc aggtgatcnt cccaaagtgc tgggattang gcgtgagcca ctgctntaga    420
tgaaacaaga ttntatgcat gtatctttan ttttttttta aagactn                   467

<210> SEQ ID NO 39
<211> LENGTH: 16
<212> TYPE: DNA
<213> ORGANISM: Unknown
<220> FEATURE:
<223> OTHER INFORMATION: The pattern is an example of a pyknon.

<400> SEQUENCE: 39
aaatgtgaag aatgtg                                                      16

<210> SEQ ID NO 40
<211> LENGTH: 16
<212> TYPE: DNA
<213> ORGANISM: Unknown
<220> FEATURE:
<223> OTHER INFORMATION: The pattern is an example of a pyknon.

<400> SEQUENCE: 40
tcatactgga gagaaa                                                      16

<210> SEQ ID NO 41
<211> LENGTH: 16
<212> TYPE: DNA
<213> ORGANISM: Unknown
<220> FEATURE:
<223> OTHER INFORMATION: The pattern is an example of a pyknon.

<400> SEQUENCE: 41
acaagtgtga agaatg                                                      16

<210> SEQ ID NO 42
<211> LENGTH: 16
<212> TYPE: DNA
```

-continued

```
<213> ORGANISM: Unknown
<220> FEATURE:
<223> OTHER INFORMATION: The pattern is an example of a pyknon.

<400> SEQUENCE: 42
catactgaag agaaac                                                       16

<210> SEQ ID NO 43
<211> LENGTH: 290
<212> TYPE: DNA
<213> ORGANISM: Unknown
<220> FEATURE:
<223> OTHER INFORMATION: The pattern is an amino acid coding region
      mosaic composed of pyknons.
<220> FEATURE:
<221> NAME/KEY: misc_feature
<223> OTHER INFORMATION: n indicates a number of nucleotides that
      separate the surrounding pyknons, as specified by Figure 13.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
```

```
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t

<400> SEQUENCE: 43
naaggaaaaa aacctttnag cagagcataa aaganattta cagtttaaaa anaaatgtga      60
agaatgtgnt catactggag agaaanaaat gtgaagaatg tgntcatact ggagagaaan    120
aaatgtgaag aatgtgnaaa tgtgaagaat gtgntcatac tggagagaaa naaatgtgaa    180
gaatgtgnaa atgtgaagaa tgtgntcata ctggagagaa anaaatgtga agaatgtgnt    240
catactggag agaaanaaat gtgaagaatg tgntcatact ggagagaaan              290

<210> SEQ ID NO 44
<211> LENGTH: 222
<212> TYPE: DNA
<213> ORGANISM: Unknown
<220> FEATURE:
<223> OTHER INFORMATION: The pattern is an amino acid coding region
      mosaic composed of pyknons.
<220> FEATURE:
<221> NAME/KEY: misc_feature
<223> OTHER INFORMATION: n indicates a number of nucleotides that
      separate the surrounding pyknons, as specified by Figure 13.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
```

```
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t

<400> SEQUENCE: 44
naaatgtgaa gaatgtgnaa atgtgaagaa tgtgntcata ctggagagaa antcatactg     60
gagagaaant catactggag agaaanaaat gtgaagaatg tgntcatact ggagagaaan    120
tcatactgga gagaaanaaa tgtgaagaat gtgntcatac tggagagaaa naaatgtaaa    180
gaatgtgntc atactggaga gaaanaaatg tgaagaatgt gn                       222

<210> SEQ ID NO 45
<211> LENGTH: 188
<212> TYPE: DNA
<213> ORGANISM: Unknown
<220> FEATURE:
<223> OTHER INFORMATION: The pattern is an amino acid coding region
      mosaic composed of pyknons.
<220> FEATURE:
<221> NAME/KEY: misc_feature
<223> OTHER INFORMATION: n indicates a number of nucleotides that
      separate the surrounding pyknons, as specified by Figure 13.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
```

```
<220> FEATURE:
<221> NAME/KEY: misc_feature
<222> LOCATION: (188)..(188)
<223> OTHER INFORMATION: n is a, c, g, or t

<400> SEQUENCE: 45
naaatgtgaa gaatgtgntc atactggaga gaaanaaatg tgaagaatgt gnaaatgtga        60
agaatgtgnc atactgaaga gaaacnaaat gtgaagaatg tgntgtgaaa aatgtggcan       120
aaatgtgaag aatgtgnaaa tgtgaagaat gtgnaaatgt gaagaatgtg ntcatactgg       180 agagaaan                                                               188

<210> SEQ ID NO 46
<211> LENGTH: 409
<212> TYPE: DNA
<213> ORGANISM: Unknown
<220> FEATURE:
<223> OTHER INFORMATION: The pattern is an amino acid coding region
      mosaic composed of pyknons.
<220> FEATURE:
<221> NAME/KEY: misc_feature
<223> OTHER INFORMATION: n indicates a number of nucleotides that
      separate the surrounding pyknons, as specified by Figure 13.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
```

```
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t
<220> FEATURE:
<221> NAME/KEY: misc_feature
<222> LOCATION: (273)..(273)
<223> OTHER INFORMATION: n is a, c, g, or t
<220> FEATURE:
<221> NAME/KEY: misc_feature
<222> LOCATION: (290)..(290)
<223> OTHER INFORMATION: n is a, c, g, or t
<220> FEATURE:
<221> NAME/KEY: misc_feature
<222> LOCATION: (307)..(307)
<223> OTHER INFORMATION: n is a, c, g, or t
<220> FEATURE:
<221> NAME/KEY: misc_feature
<222> LOCATION: (324)..(324)
<223> OTHER INFORMATION: n is a, c, g, or t
<220> FEATURE:
<221> NAME/KEY: misc_feature
<222> LOCATION: (341)..(341)
<223> OTHER INFORMATION: n is a, c, g, or t
<220> FEATURE:
<221> NAME/KEY: misc_feature
<222> LOCATION: (358)..(358)
<223> OTHER INFORMATION: n is a, c, g, or t
<220> FEATURE:
<221> NAME/KEY: misc_feature
<222> LOCATION: (375)..(375)
<223> OTHER INFORMATION: n is a, c, g, or t
<220> FEATURE:
<221> NAME/KEY: misc_feature
<222> LOCATION: (392)..(392)
<223> OTHER INFORMATION: n is a, c, g, or t
<220> FEATURE:
<221> NAME/KEY: misc_feature
<222> LOCATION: (409)..(409)
<223> OTHER INFORMATION: n is a, c, g, or t

<400> SEQUENCE: 46
naatttatat agaaatgntc ttttcaaaaa gcaantttac agttaagaaa antgataaat       60
atttgaaana aatgtaaaga atgtgnaaat gtgaagaatg tgntcatact ggagagaaan      120
acaagtgtga agaatgnaca agtgtgaaga atgnacactg gagagaaacc naaatgtgaa     180
gaatgtgntc atactggaga gaaantcata ctggagagaa anacaagtgt gaagaatgna     240
aatgtgaaga atgtgnacac tggagagaaa ccnaaatgtg aagaatgtgn tcatactgga     300
gagaaanaaa tgtgaagaat gtgncatact gaagagaaac ntgtgaaaaa tgtggcantc     360
atactggaga gaaanaaatg tgaagaatgt gnaaatgtga agaatgtgn                 409

<210> SEQ ID NO 47
<211> LENGTH: 239
<212> TYPE: DNA
<213> ORGANISM: Unknown
<220> FEATURE:
<223> OTHER INFORMATION: The pattern is an amino acid coding region
      mosaic composed of pyknons.
<220> FEATURE:
<221> NAME/KEY: misc_feature
<223> OTHER INFORMATION: n indicates a number of nucleotides that
      separate the surrounding pyknons, as specified by Figure 13.
<220> FEATURE:
<221> NAME/KEY: misc_feature
<222> LOCATION: (1)..(1)
<223> OTHER INFORMATION: n is a, c, g, or t
```

-continued

```
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t

<400> SEQUENCE: 47
naaatgtgaa gaatgtgnta aacaattctc aaaantcata ctggagagaa anaaatgtga      60
agaatgtgna aatgtgaaga atgtgncata ctgaagagaa acnaaatgtg aagaatgtgn     120
tcatactgga gagaaantgt gaaaaatgtg gcanaaatgt gaagaatgtg ncatactgaa     180
gagaaacnca tactgaagag aaacnaaatg tgaagaatgt gntcatactg gagagaaan     239

<210> SEQ ID NO 48
<211> LENGTH: 171
<212> TYPE: DNA
<213> ORGANISM: Unknown
<220> FEATURE:
<223> OTHER INFORMATION: The pattern is an amino acid coding region
      mosaic composed of pyknons.
<220> FEATURE:
<221> NAME/KEY: misc_feature
<223> OTHER INFORMATION: n indicates a number of nucleotides that
      separate the surrounding pyknons, as specified by Figure 13.
<220> FEATURE:
```

```
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t

<400> SEQUENCE: 48
ncagccagag cagggcanaa agaaacattt caaantcata ctggagagaa antcatactg       60
gagagaaana aatgtgaaga atgtgntcat actggagaga aantcatact ggagagaaan     120
aaatgtgaag aatgtgntca tactggagag aaanaaatgt gaagaatgtg n              171

<210> SEQ ID NO 49
<211> LENGTH: 205
<212> TYPE: DNA
<213> ORGANISM: Unknown
<220> FEATURE:
<223> OTHER INFORMATION: The pattern is an amino acid coding region
      mosaic composed of pyknons.
<220> FEATURE:
<221> NAME/KEY: misc_feature
<223> OTHER INFORMATION: n indicates a number of nucleotides that
      separate the surrounding pyknons, as specified by Figure 13.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
```

<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t

<400> SEQUENCE: 49
naaatgtgaa gaatgtgnaa atgtgaagaa tgtgnaaatg tgaagaatgt gntcatactg    60
gagagaaant catactggag agaaantcat actggagaga aanaattcat atggaattgn   120
aaatgtgaag aatgtgnact aatcataaga gaanacactg gagagaaacc naaatgtgaa   180
gaatgtgnaa atgtgaagaa tgtgn                                         205

<210> SEQ ID NO 50
<211> LENGTH: 256
<212> TYPE: DNA
<213> ORGANISM: Unknown
<220> FEATURE:
<223> OTHER INFORMATION: The pattern is an amino acid coding region
      mosaic composed of pyknons.
<220> FEATURE:
<221> NAME/KEY: misc_feature
<223> OTHER INFORMATION: n indicates a number of nucleotides that
      separate the surrounding pyknons, as specified by Figure 13.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:

```
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t
<220> FEATURE:
<221> NAME/KEY: misc_feature
<222> LOCATION: (222)..(222)
<223> OTHER INFORMATION: n is a, c, g, or t
<220> FEATURE:
<221> NAME/KEY: misc_feature
<222> LOCATION: (239)..(239)
<223> OTHER INFORMATION: n is a, c, g, or t
<220> FEATURE:
<221> NAME/KEY: misc_feature
<222> LOCATION: (256)..(256)
<223> OTHER INFORMATION: n is a, c, g, or t

<400> SEQUENCE: 50
naaaaatgtg gaaatgantt taataaattt tcacnaaatg taaagaatgt gnaaagaaat      60
tataccaana aatgtgaaga atgtgnaaat gtgaagaatg tgnaaatgtg aagaatgtgn     120
aaatgtaaag aatgtgnaca ctcctcagcc cttnacactg gagagaaacc naaatgtgaa    180
gaatgtgnaa atgtgaagaa tgtgnacaag tgtgaagaat gnaaatgtga agaatgtgnt    240
catactggag agaaan                                                    256

<210> SEQ ID NO 51
<211> LENGTH: 205
<212> TYPE: DNA
<213> ORGANISM: Unknown
<220> FEATURE:
<223> OTHER INFORMATION: The pattern is an amino acid coding region
      mosaic composed of pyknons.
<220> FEATURE:
<221> NAME/KEY: misc_feature
<223> OTHER INFORMATION: n indicates a number of nucleotides that
      separate the surrounding pyknons, as specified by Figure 13.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
```

```
<220> FEATURE:
<221> NAME/KEY: misc_feature
<222> LOCATION: (52)..(52)
<223> OTHER INFORMATION: n is a, c, g, or t
<220> FEATURE:
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t

<400> SEQUENCE: 51
ncagccagag cagggcanaa agaaacattt caaantcata ctggagagaa antcatactg      60
gagagaaana aatgtgaaga atgtgntcat actggagaga aantcatact ggagagaaan     120
aaatgtgaag aatgtgntca tactggagag aaanaaatgt gaagaatgtg ntcatactgg     180
agagaaanaa atgtgaagaa tgtgn                                           205

<210> SEQ ID NO 52
<211> LENGTH: 205
<212> TYPE: DNA
<213> ORGANISM: Unknown
<220> FEATURE:
<223> OTHER INFORMATION: The pattern is an amino acid coding region
      mosaic composed of pyknons.
<220> FEATURE:
<221> NAME/KEY: misc_feature
<223> OTHER INFORMATION: n indicates a number of nucleotides that
      separate the surrounding pyknons, as specified by Figure 13.
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (35)..(35)
<223> OTHER INFORMATION: n is a, c, g, or t
<220> FEATURE:
<221> NAME/KEY: misc_feature
<222> LOCATION: (52)..(52)
<223> OTHER INFORMATION: n is a, c, g, or t
<220> FEATURE:
```

```
<221> NAME/KEY: misc_feature
<222> LOCATION: (69)..(69)
<223> OTHER INFORMATION: n is a, c, g, or t
<220> FEATURE:
<221> NAME/KEY: misc_feature
<222> LOCATION: (86)..(86)
<223> OTHER INFORMATION: n is a, c, g, or t
<220> FEATURE:
<221> NAME/KEY: misc_feature
<222> LOCATION: (103)..(103)
<223> OTHER INFORMATION: n is a, c, g, or t
<220> FEATURE:
<221> NAME/KEY: misc_feature
<222> LOCATION: (120)..(120)
<223> OTHER INFORMATION: n is a, c, g, or t
<220> FEATURE:
<221> NAME/KEY: misc_feature
<222> LOCATION: (137)..(137)
<223> OTHER INFORMATION: n is a, c, g, or t
<220> FEATURE:
<221> NAME/KEY: misc_feature
<222> LOCATION: (154)..(154)
<223> OTHER INFORMATION: n is a, c, g, or t
<220> FEATURE:
<221> NAME/KEY: misc_feature
<222> LOCATION: (171)..(171)
<223> OTHER INFORMATION: n is a, c, g, or t
<220> FEATURE:
<221> NAME/KEY: misc_feature
<222> LOCATION: (188)..(188)
<223> OTHER INFORMATION: n is a, c, g, or t
<220> FEATURE:
<221> NAME/KEY: misc_feature
<222> LOCATION: (205)..(205)
<223> OTHER INFORMATION: n is a, c, g, or t

<400> SEQUENCE: 52
ntttacaaat aagaaaanaa atgtaaagaa tgtgncatac tgaagagaaa cnacaagtgt      60
gaagaatgna aatgtgaaga atgtgnaaat gtgaagaatg tgnaaatgtg aagaatgtgn     120
catactgaag agaaacnaaa tgtgaagaat gtgncatact gaagagaaac ntgaagaatg     180
tatcagantc atactggaga gaaan                                          205
```

TECHNIQUES FOR LINKING NON-CODING AND GENE-CODING DEOXYRIBONUCLEIC ACID SEQUENCES AND APPLICATIONS THEREOF

CROSS-REFERENCE TO RELATED APPLICATIONS

This application is a divisional of pending U.S. application Ser. No. 11/367,512, filed Mar. 3, 2006, the disclosure of which is incorporated by reference herein. The present application claims priority to U.S. provisional applications identified as: Ser. No. 60/658,251, filed Mar. 3, 2005, and entitled "Overrepresentation of Nucleotides in Human Chromosomes and in the 3' Untranslated Regions of Human Genes;" and Ser. No. 60/696,213, filed Jul. 1, 2005, and entitled "Techniques For Linking Non-Coding And Gene-Coding Deoxyribonucleic Acid Sequences," the disclosures of which are incorporated by reference herein.

FIELD OF THE INVENTION

The present invention relates to genes and, more particularly, to techniques for linking regions of a genome.

BACKGROUND OF THE INVENTION

It is known that the intergenic and intronic regions comprise most of the genomic sequence of higher organisms. The intergenic and intronic regions are collectively referred to as the "non-coding region" of an organism's genome, as opposed to the "gene-" or "protein-coding region" of the genome. Even though recent work suggested participation of the intergenic and intronic regions in a regulatory role, for the most part, their true function remains elusive. The search for conserved motifs, presumed to be regulatory and control signals, in regions upstream of the 5' untranslated regions (5'UTRs) of genes, has been the focus of research activities for many years.

More recently, researchers began studying the 3' untranslated regions (3'UTRs) of genes where they discovered conserved regions and showed them to be functionally significant, in direct analogy to the cis-motifs of promoter regions. Large-scale comparative analyses allowed researchers to also study conservation in the vicinity of genes and elsewhere in the genome with great success. However, these studies were carried out on only a handful of organisms at a time because of the magnitude of the necessary computations.

The analysis of 3'UTRs intensified further after it was discovered that they contain binding sites that are targeted by short interfering ribonucleic acids (RNAs) that induce the post-transcriptional control of the corresponding gene's expression through either messenger RNA (mRNA) degradation or translational inhibition. Accumulating evidence that non-coding RNAs control developmental and physiological processes and that a considerable part of the human genome is transcribed, has helped researchers identify "functional" elements in areas of the genome that are not associated with protein-coding regions.

Thus, techniques for efficiently and effectively identifying and associating non-coding regions with gene coding regions of a genome would be desirable.

SUMMARY OF THE INVENTION

Techniques for linking non-coding and gene coding regions of a genome are provided, in accordance with an illustrative embodiment of the present invention.

In a first aspect of the invention, a method of determining associations between non-coding sequences and gene coding sequences in a genome of an organism comprises the following steps. At least one conserved region is identified from a plurality of the non-coding sequences. The at least one conserved region is linked with one or more of the gene coding sequences of the genome. The at least one conserved region is associated with one or more biological processes of the organism.

In a second aspect of the invention, a method of designing one or more sequences of small interfering RNAs that can interact with one or more sites in a given transcript of a given sequence in a given organism and result in the down-regulation of the expression of the protein product encoded by the given transcript comprises the following steps. One or regions of interest are identified in the sequence of a given transcript. One or more regions are sub-selected from the collection of these regions. One or more derived sequences are generated from the sequence of the one or more sub-selected regions. The one or more derived sequences are used to create one more instances of the corresponding molecule that the one or more derived sequences represent. The one or more instances of the created molecule are used in an appropriate environment to regulate the expression of the given transcript.

In a third aspect of the invention, a method of engineering a given transcript of a given gene in a given organism in order to regulate its expression comprises the following steps. One or more regions of interest are identified in the sequence of a given transcript. One or more regions are sub-selected from the collection of these regions. The one or more sub-selected regions are used to make one or more modifications to the sequence of the given transcript.

A more complete understanding of the present invention, as well as further features and advantages of the present invention, will be obtained by reference to the following detailed description and drawings.

BRIEF DESCRIPTION OF THE DRAWINGS

FIG. 1 is a diagram illustrating an exemplary methodology for determining associations between non-coding and gene coding sequences in a genome of an organism, according to an embodiment of the present invention;

FIG. 2 is a diagram illustrating a probability density function and a cumulative distribution for lengths of patterns discovered in analyzed intergenic and intronic sequences of the human genome, according to an embodiment of the present invention;

FIG. 3 is a diagram illustrating a probability density function for a number of 16-mers with a given number of copies in a random input set, according to an embodiment of the present invention;

FIG. 4 is a diagram illustrating a preprocessing methodology, according to an embodiment of the present invention;

FIG. 5 is a diagram illustrating pattern specificity and number of appearances, according to an embodiment of the present invention;

FIG. 6 is a diagram illustrating a process for determining logically distinct patterns, according to an embodiment of the present invention;

FIG. 11 is a diagram illustrating combinatorial arrangements of pyknons in 3'UTRs, according to an embodiment of the present invention;

FIG. 12 is a diagram illustrating combinatorial arrangements of pyknons in 5'UTRs, according to an embodiment of the present invention;

FIG. 13 is a diagram illustrating combinatorial arrangements of pyknons in amino acid-coding regions, according to an embodiment of the present invention;

FIG. 15 is a diagram illustrating a partial list of biological processes whose corresponding genes show significant enrichment or depletion in pyknon instances in their 5'UTRs, CRs or 3'UTRs, according to an embodiment of the present invention;

FIG. 18 is a diagram illustrating the number of intergenic/intronic neighborhoods each of which contains the reverse complement of a pyknon and is predicted to fold into a hairpin-like structure, according to an embodiment of the present invention;

FIG. 19 is a diagram illustrating the number of positions per 10,000 nucleotides that human pyknons cover in other genomes, according to an embodiment of the present invention;

FIG. 20 is a diagram illustrating the number of human pyknons that can be found in the untranslated and coding regions of other genomes, and the number of intergenic/intronic positions that human pyknons cover in other genomes, according to an embodiment of the present invention;

DETAILED DESCRIPTION OF PREFERRED EMBODIMENTS

Figure 7:
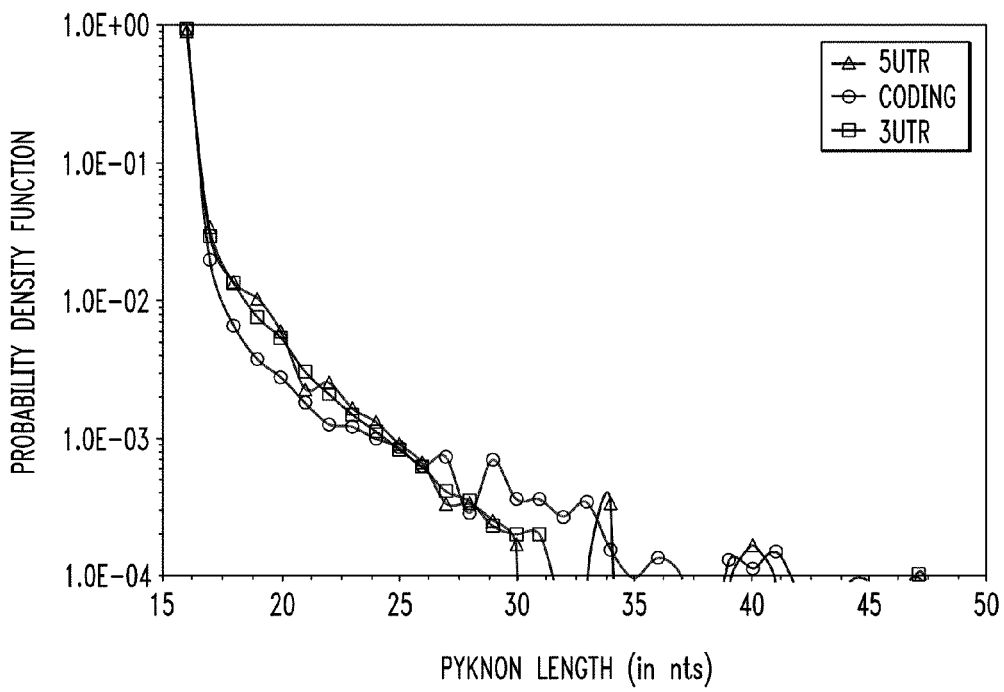
FIG. 7 is a diagram illustrating a probability density function for lengths of pyknons, according to an embodiment of the present invention.

The sequence listings referred to herein can be found in electronic text format as the file, 1500-675 PatentIn Sequence Listing.ST25, created on Wednesday, Jul. 12, 2006, having a size of 102 Kilobytes, the contents of which are incorporated by reference herein.

FIG. 1 is a diagram illustrating exemplary methodology 100 for determining associations between non-coding and gene coding sequences in a genome of an organism. In step 102, non-coding sequences from the genome of an organism are obtained. Preferably, the non-coding sequences comprise intergenic and/or intronic sequences. As used herein, the term "intergenic" refers generally to any portion of a deoxyribonucleic acid (DNA) strand that is between gene sequences. Further, as used herein, the term "intronic" refers to any portion of a DNA strand that is encompassed by an intron.

According to one exemplary embodiment, the genome comprises the human genome. Further, as will be described below, the starting point of the present techniques may be the genome of a single organism, e.g., the human genome.

In step 104, conserved regions in the intergenic/intronic sequences are identified. As will be described in detail below, these conserved regions may be identified by used pattern discovery techniques to identify patterns existing in the sequences.

In step 106, the identified conserved regions (also referred to as 'conserved motifs') of the intergenic/intronic non-coding sequences are linked to gene coding regions of the genome. Specifically, instances of the patterns, described, for example, in conjunction with the description of step 104, above, may be searched for in gene coding regions of the genome. For example, as will be described in detail below, sequences will be identified, e.g., that are at least 16 nucleotide bases in length and appear a minimum of 40 times in the non-coding region of a genome, and which also appear at least one time in the coding region of the genome. These identified sequences (motifs) link the coding and non-coding regions of the genome. As will also be described in detail below, linking the conserved regions and gene coding regions of the genome provides for an association to be made with the biological processes of the organism.

In step 108, as will be described in detail below, the identified motifs that link the non-genic and genic regions of a genome also provide for an association between these motifs and specific biological processes that even persists in organisms beyond the human genome.

As used herein, the phrase "conserved region" may also be referred to as a "conserved motif" or a "conserved block" or "an exceptionally-well-conserved block (EWCB)" or a "pyknon." The term "pyknon" is from the Greek adjective πυκνός/πυκνή/πυκνόν meaning "serried, dense, frequent."

Accordingly, using an unsupervised pattern discovery method, we processed the human intergenic and intronic regions and catalogued all variable-length patterns with identically conserved copies and multiplicities above what is expected by chance. Among the millions of discovered patterns, we found a subset of 127,998 patterns, termed pyknons, which have one or more additional non-overlapping instances in the untranslated and protein-coding regions of 30,675 transcripts from 20,059 human genes. The pyknons are found to arrange combinatorially in the 5' untranslated, coding, and 3' untranslated regions of numerous human genes where they form mosaics. Consecutive instances of pyknons in these regions exhibit a strong bias in their relative placement favoring distances of about 22 nucleotides. We also found that pyknons are enriched in a statistically significant manner in genes involved in specific processes, e.g., cell communication, transcription, regulation of transcription, signaling, transport, etc. For about $\frac{1}{3}^{rd}$ of the pyknons, the intergenic/intronic instances of their reverse complement lie within 382, 244 non-overlapping regions, typically 60-80 nucleotides long, which are predicted to form double-stranded, energetically stable, hairpin-shaped RNA secondary structures; additionally, the pyknons subsume about 40% of the known microRNA sequences, thus suggesting a possible link with post-transcriptional gene silencing and RNA interference. Cross-genome comparisons revealed that many of the pyknons are also present in the 3'UTRs of genes from other vertebrates and invertebrates where they are over-represented in similar biological processes as in the human genome. These novel and unexpected findings suggest potential functional connections between the coding and non-coding parts of the human genome.

Thus, in accordance with an illustrative methodology of the invention, we examine whether highly specific patterns exist within a single genome that may act as targets or sources for such putative regulatory activity or as a 'vocabulary' for yet undiscovered mechanisms. Our analysis represents a substantial point of departure from previous efforts. First, we carry out all of the analysis on a single genome. Second, we seek patterns in the intergenic and intronic regions of the genome (not the UTRs or protein coding) regions. Third, the pattern instances transcend chromosomal boundaries. And, fourth, we rely on the unsupervised discovery of conserved motifs instead of searching schemes. In particular, we sought to discover identically conserved, variable-length motifs of certain minimum length but unlimited maximum length in human intergenic and intronic regions. We discovered more than 66 million motifs with multiplicities well above what is expected by chance. A sizeable subset of these motifs, referred to as the pyknons, have one or more additional instances in the untranslated and coding regions of almost all known human genes and exhibit properties that suggest the possibility of an extensive link between the non-genic and genic regions of the genome and a connection with post-transcriptional gene silencing (PTGS) and RNA interference (RNAi).

As described, for example, in conjunction with the description of step 104 of FIG. 1, above, according to the techniques described herein, a pattern discovery step may be performed. We used the parallel version of a pattern discovery algorithm described in I. Rigoutsos et al., *Combinatorial Pattern Discovery in Biological Sequences: the TEIRESIAS Algorithm,* 14 BIOINFORMATICS 1, pgs. 55-67 (January 1998) (hereinafter "Rigoutsos"), the disclosure of which is incorporated by reference herein. The pattern discovery (Teiresias) algorithm seeks variable-length motifs that are identically conserved across all of their instances, comprise a minimum of L=16 nucleotides and appear a minimum of K=40 copies in the processed input (see below regarding the values of L, K). The algorithm guarantees the reporting of all composition-maximal and length-maximal patterns satisfying these parameters. The input comprised the intergenic and intronic sequences (step 102 of FIG. 1) of the human genome from ENSEMBL Rel. 31 (see Stabenau, A., McVicker, G., Melsopp, C., Proctor, G., Clamp, M. & Birney, E. (2004) *Genome Res* 14, 929-33) for a total of 6,039,720,050 nucleotides. The input did not include the reverse complement of the 5' untranslated, amino acid coding or 3' untranslated regions of any human genes. This exclusion ensures that any discovered patterns are not connected in any way to sequences of known genes, protein motifs or domains. The algorithm ran on a shared-memory architecture with 128 Gigabytes of main memory and 8 processors running at a clock frequency of 1.75 GHz, and generated an initial set $P_{init}$ of 66+ million statistically significant patterns (see below). Most of the patterns in $P_{init}$ were a few tens of nucleotides in length. FIG. 2 shows the probability density function (in black) and cumulative distribution (in light gray) for the lengths of the more than 66 million patterns discovered in the analyzed intergenic and intronic sequences of the human genome. These patterns form the set $P_{init}$. As can be seen from FIG. 2, more than 95% of all discovered patterns are shorter than 100 nucleotides. Note that the primary Y-axis is logarithmic whereas the secondary is linear.

The Teiresias discovery algorithm that we used for this analysis requires the setting of three parameters: L, W and K. The parameter L controls the minimum possible size of the discovered patterns but has no bearing on the patterns' maximum length; the latter is not constrained in any way. The parameter W satisfies the inequality $W \geq L$ and controls the 'degree of conservation' across the various instances of the reported patterns: smaller (respectively, larger) values of W will tolerate fewer (respectively, more) mismatches across the instances. Since for this analysis, we are interested only in patterns with identically conserved instances, we set W=L (i.e., the patterns contained no "wild cards"). Finally, the parameter K controls the minimum required number of appearances before a pattern can be reported by the algorithm.

For a given choice of L, W and K, the algorithm guarantees the reporting of all patterns that have K or more appearances in the processed input and are such that any L consecutive (but not necessarily contiguous) positions span at most W positions. These patterns are generally overlapping: a given sequence location can simultaneously appear in multiple, distinct, non-redundant patterns. It is also important to stress three properties of the algorithm. First, as stated above, the value L does not impose any constraint on the maximum length of a pattern which is unbounded. Second, each reported pattern will be maximal in composition, i.e., it cannot be made more specific by specifying the value of a wild-card without decreasing the number of locations where it appears. And, third, each reported pattern will be maximal in length, i.e., it cannot be made longer without decreasing the number of locations where it appears. In this discussion, we use the terms pattern, block and motif interchangeably.

Opting for small L values generally permits the identification of shorter conserved motifs that may be present in the processed input, in addition to all longer ones—see above properties. Generally, for short motifs to be claimed as statistically significant they need to have a large number of copies in the processed input; requiring a lot of copies runs the risk of discarding bona fide motifs. On the other hand, larger values of L will generally permit the identification of statistically significant motifs even if these motifs repeat only a small number of times. This happens at the expense of significant decreases in sensitivity; i.e. bona fide motifs will be missed.

For our analysis, we have selected L=16, a value that strikes a balance between the desirable sensitivity (which favors lower L values) and achievable specificity (which favors higher L values). We stress that the maximality properties of the pattern discovery step ensure that we will be able to report any and all motifs that are 16 nucleotides or longer. And as explained above, we will set W=L.

The last parameter that needs to be set is K, the required number of appearances for a pattern to be reported. K needs to be set to a value that can ensure that the reported patterns could not have been derived from a random database with the same size as the input at hand. In order to determine this value, we used several randomly-shuffled versions of our intergenic and intronic input (of approximately 6 billion bases) and inthere sought frequent, fixed-size 16-mers with all low-complexity 16-mers removed by NSEG (see Wootton, J. C. & Federhen, S. (1993) *Computers in Chemistry* 17, 149-163). The idea here is that if a randomly-shuffled version of our input set cannot give rise to any 16-mers that appear more than $K_X$ times, then it will also be true that no patterns exist in the input set that are longer than 16 nucleotides and have more than $K_X$ copies. Several iterations of this process allowed us to establish that $K_X$=23. FIG. 3 shows the probability density function for the number of 16-mers with a given number of copies in the random input set—note that both the X and Y axes are logarithmic. From this, it follows that a randomly-shuffled version of our input set cannot possibly give rise to patterns which are longer than 16 nucleotides and have more than 23 copies: in fact, as a pattern increases in length, the number of times it appears in a given input set can only decrease. We thus opted for the even larger threshold of K=40 for our pattern discovery step.

Before we sought to discover patterns in the intergenic and intronic regions of the human genome, we preprocessed the sequences and removed: a) all the regions that corresponded to 5' untranslated, coding and 3' untranslated regions of known genes; and, b) all the regions that were the reverse complement of 5' untranslated, coding and 3' untranslated regions of known genes. We show this preprocessing step pictorially in FIG. 4. The genomic input before the preprocessing step is shown above the arrow, and the input upon which pattern discovery is run is shown below the arrow.

Under the assumption that all four nucleotides are equiprobable (i.e., $p_A = p_T = p_C = p_G = 1/4$), independent, and, identically distributed, we estimate the probability p of a pattern of length l to be $p = 4^{-l}$. We can compute the probability $Pr_k$ to observe k instances of a given pattern in a database of size D (D$\gg$1) to be $Pr_k \approx (pD)^k e^{-pD}/k!$ (Poisson distribution). The least specific pattern that our method will discover is one that is the shortest possible (i.e., l=L=16) and appears the smallest allowed number of times (i.e., k=K=40): if D=6.0×10$^9$ bases (=all chromosomes and both strands), then $Pr_k$=1.95×10$^{-43}$.

We now revisit this calculation by taking into account the nucleotides' natural probability of occurrence. Using ENSEMBL Release 31 from May 2005 (based on NCBI Assembly 35 from July 2004) as our database D, we see that the fraction of bases that are undetermined across the 24 human chromosomes ranges from roughly 1.2 to 61.0% for the Y chromosome. Of course, the following constraints should apply: $p_A = p_T$ and $p_C = p_G$. Since the fractions of nucleotides that are undetermined are not equal, the required balance between A/T and C/G is only approximately preserved. Ignoring the unspecified positions and recomputing ratios based on the remaining bases, we find that $p_A = p_T \approx 3/10$ and $p_C = p_G \approx 2/10$.

Let us consider a block of size l and let "match" indicate the match between the i-th character of this block and a character c at position in a database D of nucleotide sequences.

Then it is easy to see that:

$$Pr(\text{match}) = Pr(\text{match with } c) = Pr(\text{match} \wedge (c \text{ is one of } A, C, G, T))$$

$$= Pr((\text{match} \wedge c = A) \vee (\text{match} \wedge c = C) \vee (\text{match} \wedge c = G) \vee (\text{match} \wedge c = T))$$

$$= Pr(\text{match} \mid A)Pr(A) + Pr(\text{match} \mid C)Pr(C) + Pr(\text{match} \mid G)Pr(G) + Pr(\text{match} \mid T)P(T)$$

$$= Pr(A)Pr(A) + Pr(C)Pr(C) + Pr(G)Pr(G) + Pr(T)P(T)$$

$$= Pr(A)^2 + Pr(C)^2 + Pr(G)^2 + Pr(T)^2$$

$$= p_A^2 + p_C^2 + p_G^2 + p_T^2 = 0.3^2 + 0.3^2 + 0.2^2 + 0.2^2 = 0.26$$

In this analysis, we consider blocks of length l with l$\geq$16. Naturally, these shortest blocks will be associated with the largest probability p of observing a pattern accidentally—the value p decreases as the value of l increases. The probability that a block of length l=16 will have one instance in the database D is then $p_1 \triangleq Pr(\text{match})^{16} = (0.26)^{16}$ or $p_1 = 4.4 \times 10^{-10}$.

An alternative way to approach this is to assume that the block of length l is constructed by drawing from the same nucleotide distribution that gives rise to the database D. Then, a block of length l=16 would comprise $p_A * 16 \approx 5$ A's, $p_C * 16 \approx 5$ C's, $p_G * 16 \approx 3$ G's and $p_T * 16 \approx 3$ T's. Then, the probability that this block will arise accidentally is $p_2 \triangleq p_A^5 * p_C^5 * p_G^3 * p_T^3 = 3.8 \times 10^{-10}$.

We can compute the probability of finding k accidental instances in a database D that contains 6×10$^9$ bases where each of the instances is independent of all the preceding instances using the Poisson distribution $Pr_k (pD)^k e^{-pD}/k!$. The probability $Pr_k$ that a 16-mer will appear k times with k=40 is equal to 4.5*10$^{-33}$ (resp. 2.6*10$^{-35}$) if $p_1$ (resp. $p_2$) is used in the calculation.

We thus can see that even if we take into account the natural frequency of appearance in the human genome of each of the four nucleotides, the probability that one of our discovered blocks is accidental remains very small even for blocks of size 16 that appear only 40 times.

Alternatively, we can estimate the significance of our patterns using z-scores: for the least specific patterns of length 16 that have exactly 40 identical copies we obtain the remarkably-high value of z=32.66. Longer patterns and patterns with more intergenic/intronic copies have even higher z-scores. These analyses confirm in different ways that every one of our discovered patterns is statistically significant and not the result of a random process. These conclusions hold true for the reverse complements of the discovered patterns as well and for the pyknons that are a subset of the discovered patterns $P_{init}$.

It is to be noted that we will use the terms "coding" and "coding region" (abbreviated as CR and CRs) to refer to the translated, amino-acid coding part of exons.

We now describe the step of determining which of the discovered patterns have additional instances in the 5'UTRs, CRs or 3'UTRs of known genes. Once the pattern discovery step has produced the set $P_{init}$ of variable length patterns, we processed it to identify 'logically distinct' patterns using the following approach. Let there be a recurrent logical unit which appears several times in the intergenic/intronic regions of the human genome; each one of its instances is assumed to have different lengths that reflect varying degrees of conservation. For simplicity, we assume here that different degrees of conservation will result in variable length instances of the pattern. We only seek patterns with identically-conserved instances so this is a correct assumption. For example's sake, we will assume that all variations of the logical unit contain an intact copy of an 18-nucleotide core motif; let TCCCATAC-CACGGGGATT (SEQ ID NO: 1) represent this core. As the instances of the logical unit become longer and thus more specific, the number of appearances in the input decreases. FIG. 5 shows this example in more detail. Several hypothetical variations of the logical unit are aligned around the common core motif and the number of instances is listed next to each variation.

We reasoned that these patterns should be processed in order of decreasing value of the total number of positions that they span: this number is simply the product of each pattern's length by the number of times it appears in the input. As patterns are examined in turn, some of them are selected and kept whereas others collide with earlier-made selections.

Two collision scenarios are possible and we examine them with the help of FIG. 6. Two blocks, light and darker gray, are shown therein together with a 'reference set' of sequences. The light gray block corresponds to a pattern that has already been examined and placed at all its instances. The instances of the darker gray block show the intended placements for the pattern currently under consideration. The blocks collide at two locations (they overlap in the first and second sequence) but the rest of their instances are disjoint. We have two possibilities regarding the handling of collisions. The darker gray block is kept if and only if there is at least one other location in the reference sequence set where it can be placed without generating a collision (e.g. the fifth and sixth sequences in FIG. 6). Alternatively, the darker gray block is kept if and only if it generates no collisions whatsoever with any block that has already been selected and placed. We have opted for the stricter, second choice: if a pattern's instance uses a position that has already been claimed by an earlier-selected pattern, then the pattern under consideration will be discarded and not considered further. Generally, it will be redundant variations of the same pattern that will generate collisions: only one pattern will be used to represent a core motif such as the one shown in FIG. 5.

The one remaining element is to decide which sequences to use as the reference set. We have chosen to use each of the 5'UTRs, CRs, and 3'UTRs in turn. Sub-selecting among the patterns in $P_{init}$ with the help of each of the 5' untranslated, coding and 3' untranslated regions gives rise to the pattern collections $P_{5'UTR}$, $P_{CODING}$ and $P_{3'UTR}$ respectively. The union of these sets, $P_{5'UTR} \cup P_{CODING} \cup P_{3'UTR}$ comprises the pyknons, i.e., patterns that were originally discovered in the intergenic and intronic regions of the human genome and which have additional instances in the 5' untranslated, coding and 3' untranslated regions of known human genes.

We used the above steps to determine which of the discovered patterns has additional instances in the untranslated and coding regions of genes. After filtering the surviving patterns for low-complexity with NSEG (Wootton, J. C. & Federhen, S. (1993) *Computers in Chemistry* 17, 149-163), we generated three patterns sets $P_{5'UTR}$, $P_{CODING}$ and $P_{3'UTR}$ that contained 12,267, 54,396 and 67,544 patterns respectively and had additional instances in 5'UTRs, CRs and 3'UTRs. The union of $P_{5'UTR} \cup P_{CODING} \cup P_{3'UTR}$ contained 127,998 patterns indicating that the three pattern sets are largely disjoint. We refer to these 127,998 patterns as pyknons.

We know describe some properties of the pyknons. The three patterns sets $P_{5'UTR}$, $P_{CODING}$ and $P_{3'UTR}$ contain 12,267, 54,396 and 67,544 blocks respectively. The union $P_{5'UTR} \cup P_{CODING} \cup P_{3'UTR}$ comprises the 127,998 pyknons. In FIG. 7, we show the probability density function for the length of the pyknons; the function is shown separately for each of the three subsets that make up the pyknon collection. Note that the Y-axis is logarithmic.

The patterns in each of the three collections, $P_{5'UTR}$, $P_{CODING}$ and $P_{3'UTR}$, fall into one of two types. "Type-A" patterns are patterns whose reverse complement is also present in the same collection (note that reverse palindromes are included among the type-A patterns). "Type-B" patterns are patterns whose reverse complement is absent from the collection. The breakdown for each of $P_{5'UTR}$, $P_{CODING}$ and $P_{3'UTR}$ is as follows: $P_{5'UTR}$ contains 217 type-A blocks and 11,835 type-B blocks; $P_{CODING}$ contains 1,038 type-A blocks and 52,330 type-B blocks; and $P_{3'UTR}$ contains 2,501 type-A blocks and 62,577 type-B blocks. The clear majority of the blocks in each of the three collections are type-B blocks.

Figure 8:
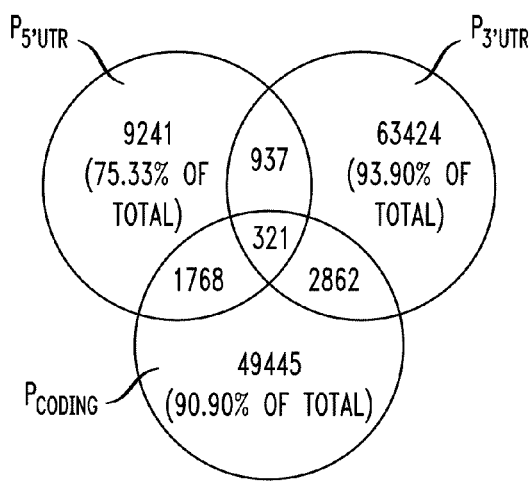
FIG. 8 is a diagram illustrating a number of blocks that are shared by three sets whose union makes up a pyknon collection, according to an embodiment of the present invention.

With respect to their content, the three collections are largely disjoint, a characteristic that presumably reflects sequence differences that are inherent to the actual 5'UTRs, CRs and 3'UTRs. FIG. 8 shows pictorially the relationship among the members of the three sets $P_{5'UTR}$, $P_{CODING}$ and $P_{3'UTR}$: note the small cardinalities of the various intersections.

Figure 9:
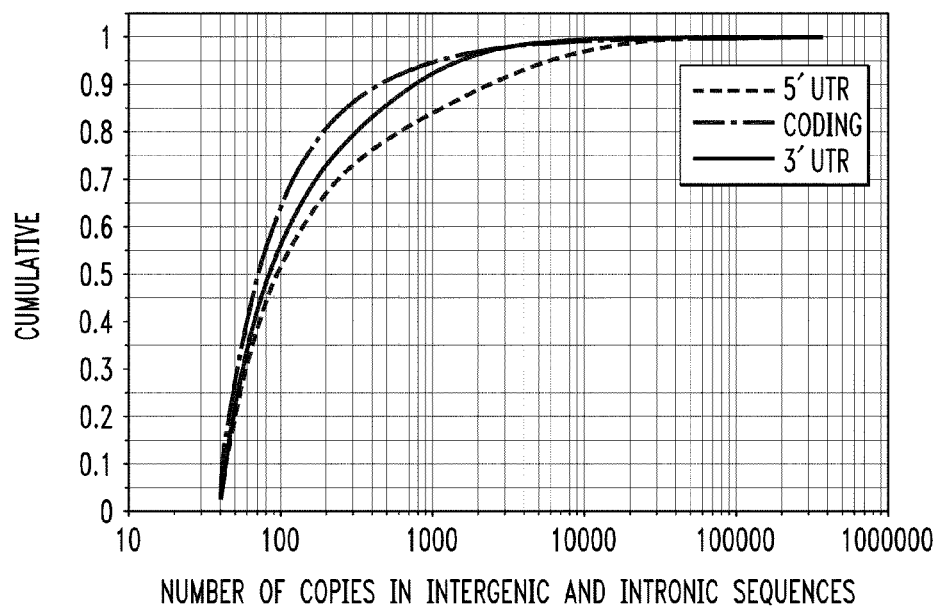
FIG. 9 is a diagram illustrating a cumulative function for a number of intergenic and intronic copies of pyknons, according to an embodiment of the present invention.

Finally, we comment on the number of intergenic and intronic copies of a pyknon. This number spans a very wide range of values with the most frequent pyknon having 356, 989 copies—the minimum number of copies is, by design, equal to K=40. For about 95% of the pyknons, their intergenic/intronic copies are fewer than 2,000. FIG. 9 shows the cumulative distributions for the number of intergenic and intronic copies of the pyknons—the distribution is again shown separately for each of $P_{5'UTR}$, $P_{CODING}$ and $P_{3'UTR}$ in order to highlight the similarities and differences of the three sets.

Figure 10:
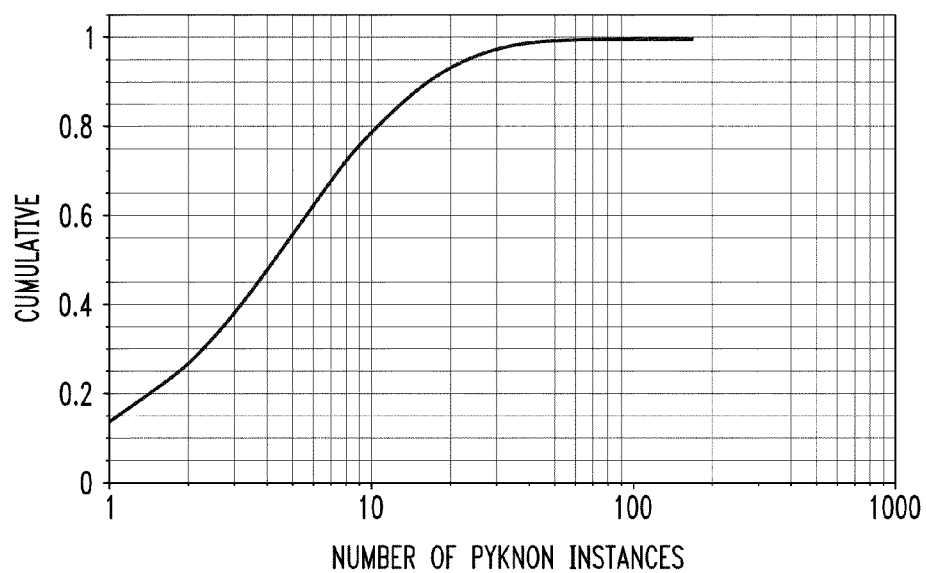
FIG. 10 is a diagram illustrating a cumulative function showing what percentage of affected transcripts contain N or more pyknon instances, according to an embodiment of the present invention.

The pyknons also exhibit a number of properties that connect the non-genic and genic regions of the human genome, as well as other genomes, in unexpected ways. In particular:

The pyknons have one or more instances within nearly all known genes. The 127,998 pyknons that we originally discovered in the human intergenic and intronic regions have an additional 226,874 non-overlapping copies in the 5'UTRs, CRs or 3'UTRs of 20,059 genes (30,675 transcripts). That is, more than 90% of all human genes contain one or more pyknon instances. The pyknons in $P_{5'UTR}$ cover 3.82% of the 6,947,437 nucleotides in human 5'UTRs; the pyknons in $P_{CODING}$ cover 3.04% of the 50,737,024 nucleotides in human CRs; and, the pyknons in $P_{3'UTR}$ cover 7.33% of the 25,597,040 nucleotides in human 3'UTRs. The distribution of pyknons in the various transcripts is not uniform. FIG. 10 shows the cumulative for the number of transcripts with a given number of pyknons instances in them. As can be seen, about 52% of the 30,675 affected transcripts contain four or more pyknon instances; of these about 2,200 transcripts contain 20 or more pyknon instances in them.

The pyknons arrange combinatorially in many human 5'UTRs, CRs and 3'UTRs forming mosaics. In those cases where we find many pyknons in one transcript, the pyknons arrange combinatorially and form mosaics. FIG. 11 shows an example of such a combinatorial arrangement in the 3'UTRs of birc4 (an apoptosis inhibitor) and nine other human genes. The 3'UTR of birc4 contains 100 instances of 95 distinct pyknons: of these, 22 are also present in the 3'UTRs of the other nine genes shown. One or more instances of the 95 pyknons from birc4's 3'UTR exist in the 3'UTRs of 2,306 transcripts (data not shown).

We next show two more examples, one involving 5' untranslated and the other involving coding regions. It is important to stress here that the pyknons are initially discovered in an input that includes neither untranslated/amino-acid-coding sequences nor their reverse-complement; thus, pyknon arrangements such as the ones shown in the following two examples represent non-trivial findings from the standpoint of statistical significance. FIG. 12 shows an example of combinatorial rearrangement in the 5'UTRs of ENSG00000196809 a gene of unknown function and 8 more human genes. 63 distinct pyknons have a total of 65 instances in the 5'UTR of ENSG00000196809. Of the 63 pyknons in the 5'UTR of ENSG00000196809, nine are also shared with the remaining eight genes of the shown group.

FIG. 13 shows an example of combinatorial rearrangement in human coding regions with the help of the amino-acid-coding sequences from 10 distinct genes: 9 pyknons have a total of 124 instances in the coding regions of the shown transcripts with several of the conserved pyknons appearing twice or more in a given sequence.

Recall that we initially discovered the pyknons in an input that included neither transcribed gene-related sequences nor their reverse-complement. Thus, finding so many pyknons with instances in human 5'UTRs, CRs and 3'UTRs is significant, especially in view of the three striking examples of combinatorial rearrangements shown above.

The pyknons account for $\frac{1}{6}^{th}$ of the human intergenic and intronic regions. The intergenic and intronic copies of the pyknons span 692,393,548 positions on the forward and reverse strands. For those pyknons whose reverse complements are not already in the list of 127,998 pyknons, their Watson-strand instances impose constraints on their Crick-strand instances. Considering this and recalculating shows that 898,424,004 positions, i.e., about $\frac{1}{6}^{th}$ of the human intergenic/intronic regions, are covered by pyknons and their reverse complement.

The pyknons are non-redundant. We clustered the pyknons using a scheme based on BLASTN (Altschul, S. F., Gish, W., Miller, W., Myers, E. W. & Lipman, D. J. (1990) *J Mol Biol* 215, 403-10). Two pyknons are redundant if they agree on at least X % of their positions. Since our collection includes pyknon pairs whose members are the reverse complement of one another, we had to ensure that the clustering scheme did not over-count: when comparing sequences A and B, we examined for redundancy the pair (A,B) and the pair (reverse-complement-of-A,B). Clustering at X=70, 80 and 90%, we generated clusters with 32621, 44417 and 89159 pyknons respectively. The high numbers of surviving clusters show that the pyknons are largely distinct.

We next describe the BLASTN-based clustering scheme. Let us assume that we are given a set of N sequences of nucleic acids of variable length, and a user-defined threshold X for the permitted, maximum remaining pair-wise sequence similarity. Then, we carry out the following steps:

sort the N sequences in order of decreasing length;
let $S_i$ denote the i-th sequence of the sorted set;
let $S_l$ be the longest sequence of the sorted set;
CLEANED_UP_SET←$S_l$
for i=2 through N do
  use $S_i$ as query to run BLAST against the current contents of CLEAN
  if the top BLAST hit T agrees with $S_i$ or with the reverse complement of $S_i$ at more than X % of T's positions then
    make $S_i$ a member of the cluster represented by T;
    discard $S_i$;
  else
    CLEANED_UP_SET←CLEANED_UP_SET_U {$S_i$};
end-for-loop Upon termination, the set CLEANED_UP_SET contains sequences no pair of which agrees on more than X % of the positions in the shorter of the two sequences.

Figure 14:
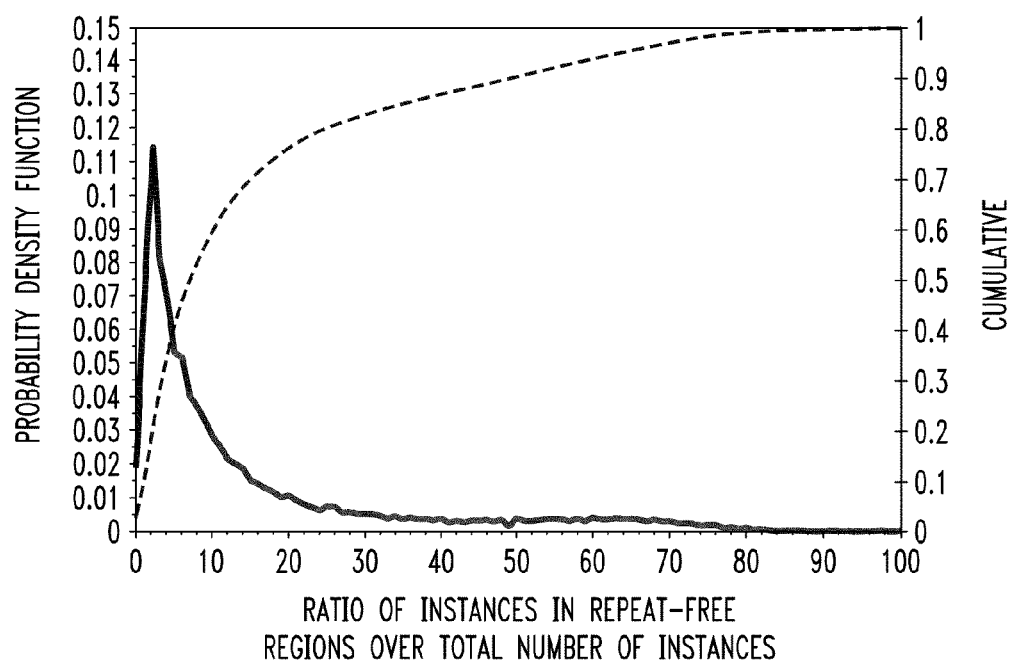
FIG. 14 is a diagram illustrating a probability density function and corresponding cumulative function for variable representing the fraction of pyknon instances located in repeat-free regions, according to an embodiment of the present invention.

On pyknons and repeat elements. 1,292 pyknons (1.0%) have instances occurring exclusively inside repeat elements as determined with the help of RepeatMasker (Smit, A. & Green, P. RepeatMasker: ftp.genome.washington.edu/RM/RepeatMasker.html). Seventy-nine pyknons have instances exclusively in repeat-free regions. And, the remaining 126,627 pyknons (98.9% of total) have instances both inside repeat elements and in repeat-free regions. A question that arises here is what fraction, on average, of the total number of copies of pyknons is generated from repeat-free regions. We have computed the probability density and cumulative functions for this fraction, and plot them in FIG. 14. As can be seen, about 60% of the pyknons have more than 90% of their copies inside repeat elements. However, the remaining 40% of the pyknons, which amounts to a little more than 50,000 pyknons, have between 10% and 100% of their instances in regions that are free of repeats.

The pyknons are distinct from the "ultraconserved elements." 52 pyknons have instances in 46 of the 481 ultraconserved elements (Bejerano, G., Pheasant, M., Makunin, I., Stephen, S., Kent, W. J., Mattick, J. S. & Haussler, D. (2004) *Science* 304, 1321-5) and cover 0.67% of the 126,007 positions: uc.73+ contains four pyknons; uc.23+, uc.66+, uc.143+ and uc.414+ each contain two pyknons; the remaining 41 elements contain a single pyknon each.

The pyknons are associated with specific biological processes. For 663 GO terms (Ashburner, M., Ball, C. A., Blake, J. A., Botstein, D., Butler, H., Cherry, J. M., Davis, A. P., Dolinski, K., Dwight, S. S., Eppig, J. T., Harris, M. A., Hill, D. P., Issel-Tarver, L., Kasarskis, A., Lewis, S., Matese, J. C., Richardson, J. E., Ringwald, M., Rubin, G. M. & Sherlock, G. (2000) *Nat Genet* 25, 25-9) describing biological processes at varying levels of detail, we found that the corresponding genes had either a significant enrichment or a significant depletion in pyknon instances. FIG. 15 shows a partial list of GO terms that are enriched or depleted in pyknons.

We determined these associations as follows: each gene was included in a list n times, where n is the number of pyknons found in its 5' untranslated, coding or 3' untranslated region, respectively—to avoid over-counting, pyknons with multiple instances in the transcript(s) of a given gene were counted only once. For the sets of sequences belonging to human 5'UTRs, CRs and 3'UTRs, respectively, the binomial distribution was used to estimate the significance of enrichment (or depletion) of pyknons encountered in a group of genes associated with a certain term, compared to the expected frequency of this term in a background set comprising all genes with 5' untranslated, coding or 3' untranslated regions respectively.

Two control tests helped ensure the significance of our findings. First, we generated gene lists identical to the ones derived from the real data but which were created by random associations with pyknons: we found that only 1 of the generated 84,780 p-values exceeded our selected significance threshold of a Bonferroni-corrected |log(p-value)| of about 2.3 (data not shown). Second, we examined the relation between GO-process associations and the amount of sequence covered by the pyknons: this test allowed us to rule out the possibility that the derived significant enrichment/depletion were due to variations in sequence length for the genes associated with given cellular processes.

Figure 16:
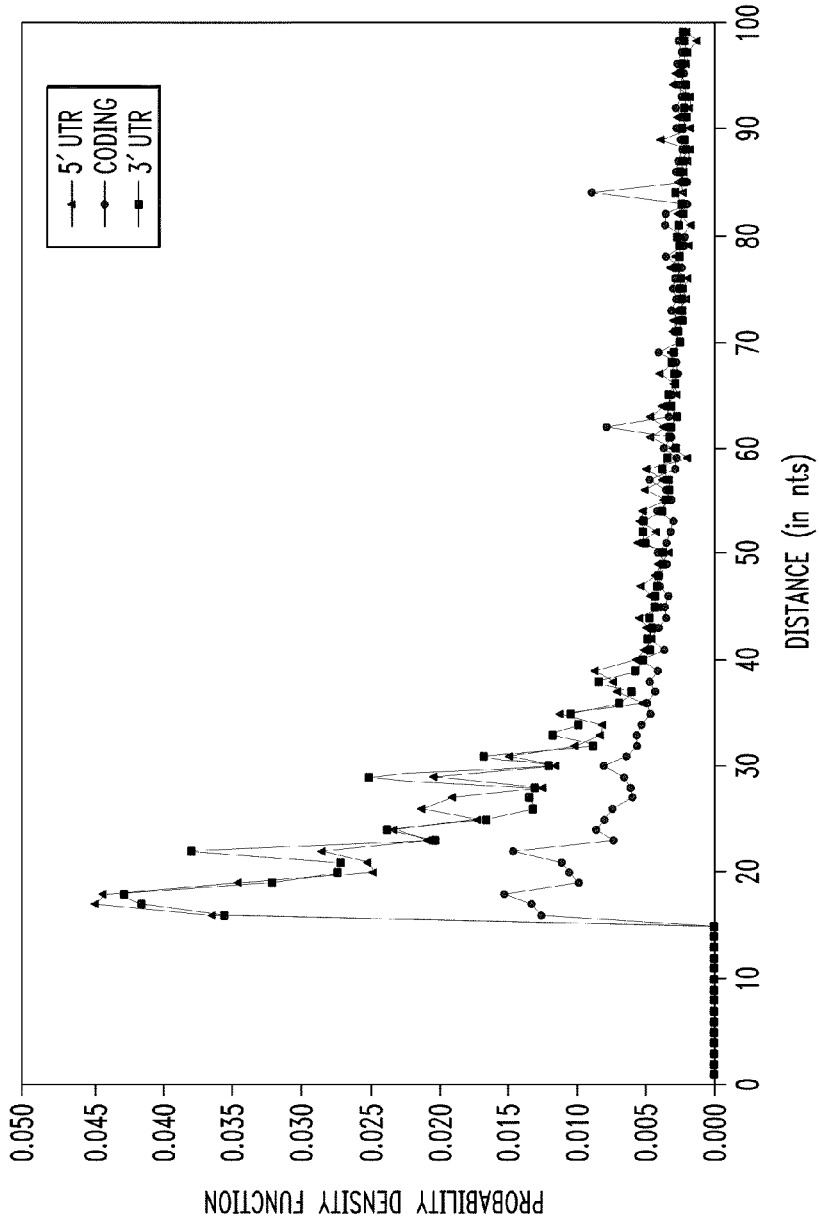
FIG. 16 is a diagram illustrating probability density functions for the distance between starting points of consecutive instances of pyknons, according to an embodiment of the present invention.

The relative positioning of pyknons in 5'UTRs, CRs and 3'UTRs is strongly biased but consecutive pyknon instances are not correlated. We examined the distances between consecutive pyknons, independently for each of the 5'UTRs, CRs and 3'UTRs. FIG. 16 shows the calculated probability density functions. Given the stringent criteria, we used when selecting pyknons, the coverage of each region is not dense, hence the tail-heavy distributions. The three curves have similar shapes, pronounced peaks at abscissas 18 and 22, and an overall preference for distances between 18 and 31 nucleotides.

Figure 17A:
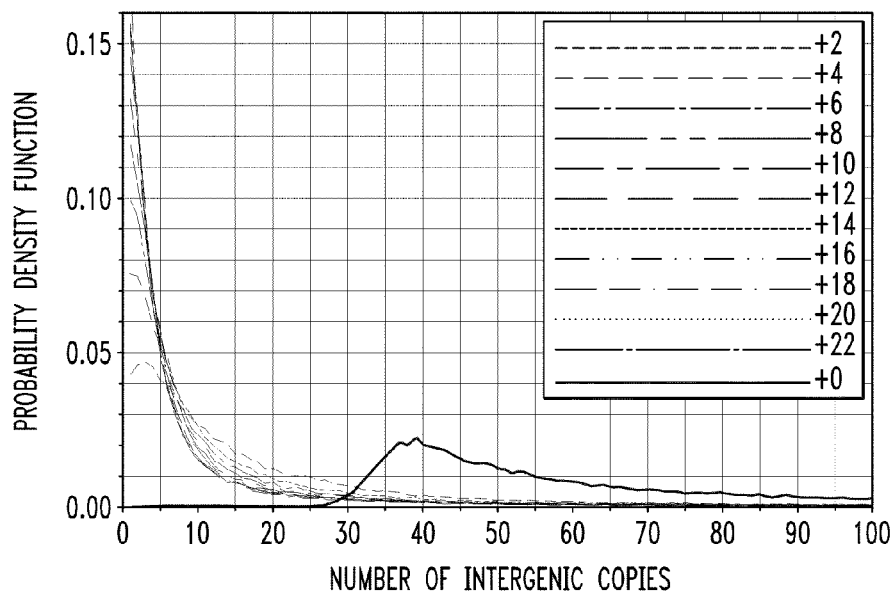
FIG. 17 is a diagram illustrating probability density functions for the number of intergenic and intronic copies of variable-length strings derived by counting instances of 3'UTR-conserved pyknons after shifting, according to an embodiment of the present invention.
Figure 17B:
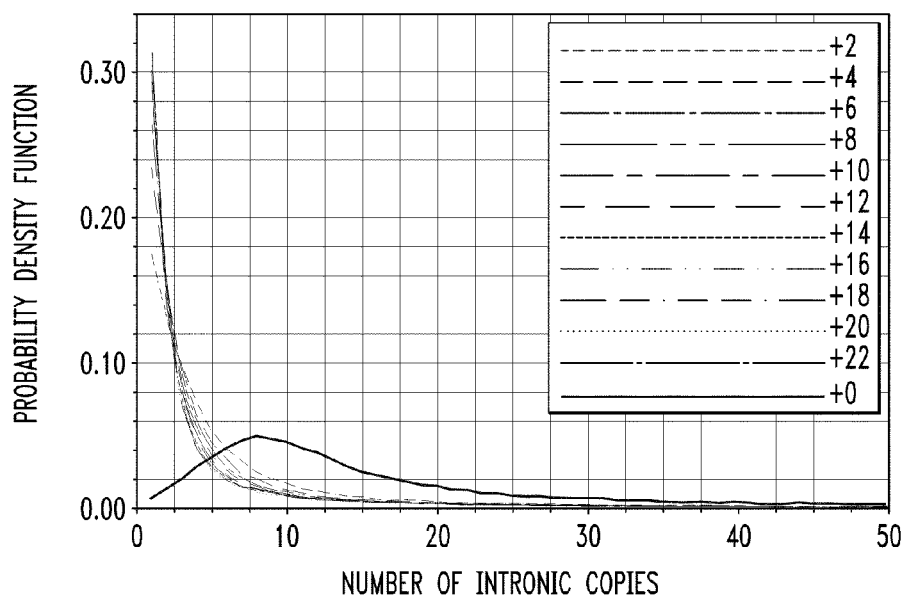

We next examined whether or not the pyknons are fragments of larger conserved regions. Let b denote a pyknon and let us assume that, unbeknownst to us, b is part of a larger-size conserved unit B. Then B will correspond to a larger area than the instance carved out by b, and thus there will be length(B)–length(b)+1 strings in the immediate neighborhood of b whose intergenic and intronic counterparts have as many identically-conserved copies as B. We tested this possibility in 3'UTRs by taking each instance of a pyknon, shifting it by +d (resp. –d), generating a new string and locating the new string's instances in the human intergenic and intronic regions. Had b been part of a larger logical unit, then for some values of d the number of intergenic and intronic copies of the newly formed string would have remained identical to those of b. On the other hand, if b were not part of a larger unit, then the new string would now cross the "natural boundaries" of the underlying presumed logical units and the new string's intergenic/intronic copies would be reduced drastically. Given the strict criteria that we used in identifying pyknons, it is possible that we discarded blocks that are conserved in intergenic/intronic regions and have instances in human coding regions. In this case, a shift of +/–d may end up generating a string that was not included in our set of pyknons but continues to have numerous intergenic/intronic copies. FIG. 17 shows the results obtained for the 3'UTRs for d ∈ and separately for intergenic (top half) and intronic (bottom half) regions; the curves for d=0 correspond to the pyknons in $P_{3'UTR}$. Note that even for a small shift of d=2 positions, the derived, shifted strings have strikingly fewer copies than the pyknons in $P_{3'UTR}$, and this holds true for both the intergenic and intronic instances. We obtained similar results for negative d's (data not shown).

The pyknons are possibly linked to PTGS. The most conspicuous feature of FIG. 16 is the strong preference for distances typically encountered in the context of PTGS. By definition, the 127,998 pyknons have one or more instances in the untranslated and coding regions of human genes: for each pyknon, we generated its reverse complement $\bar{\beta}$, identified all of $\bar{\beta}$'s intergenic and intronic instances, and predicted the RNA structure and folding energy of the immediately surrounding neighborhoods using the Vienna package (Hofacker, I. L., Fontana, W., Stadler, P., Bonhoeffer, L. S., Tacker, M. & Schuster, P. (1994) *Monatshefte f. Chemie* 125, 167-188). We discarded structures whose predicted folding energies were >–30 Kcal/mol, and structures (including ones with favorable folding energies) that were predicted to locally self-hybridize, even if the involved positions represented a miniscule fraction of the total length of the regions under consideration. We also discarded structures that contained either a single large bulge or many unmatched bases. Each of the surviving regions was predicted to fold into a hairpin-shaped RNA structure that had a straightforward arm-loop-arm architecture, contained very small bulges if any, and was energetically very stable. The analysis identified 380,084 non-overlapping regions predicted to form hairpin-shaped structures (298,197 in intergenic and 81,887 in intronic sequences). These 380,084 regions contained instances of the reverse complement of 37,421 pyknons (29.23% of total). In terms of length, the clear majority of these regions are between 60 and 80 nucleotides long.

FIG. 18 shows the density of the surviving regions per 10,000 nucleotides and for each chromosome separately. The density is reported for each chromosome and separately for the intergenic and intronic regions. Per unit length, there are more predicted hairpins in intronic rather than intergenic regions but the shear difference in the magnitude of these regions results in the intergenic regions contributing the bulk of the hairpins. Interestingly, the density of discovered hairpins is not constant across chromosomes: chromosomes 16, 17, 19 and 22 who are the most densely-packed in terms of predicted hairpins are also among the shortest in length. We emphasize that the average pyknon has length similar to that of a typical microRNA and that there is a straightforward sense-antisense relationship between segments of the 380,084 hairpins and the pyknons instances in human 5'UTRs/CRs/3'UTRs. Also note that the regions containing the 81,887 intronic hairpins will be transcribed: these regions account for 21,727 of the 37,421 pyknons that are linked to hairpins.

If pyknons are indeed connected to PTGS, then two hypotheses arise from FIG. 16: a) in addition to 3'UTRs, gene silencing is likely effected through the 5'UTRs and amino acid coding regions; and, b) RNAi products in animals likely form distinct quantized categories based on size and have preferences for lengths of 18, 22, 24, 26, 29, 30 and 31 nucleotides.

The pyknons relate to known microRNAs. We formed the union of the RFAM (Griffiths-Jones, S., Bateman, A., Marshall, M., Khanna, A. & Eddy, S. R. (2003) *Nucleic Acids Res* 31, 439-41) and pyknon collections, and clustered it with the above-described BLASTN-based scheme, using a threshold of pair-wise remaining sequence similarity of 70%; i.e., we allowed up to six mismatches in 22 nucleotides. When comparing two sequences A and B, we avoided over-counting by examining for redundancy the pairs (A,B) and (reverse-complement-of-A,B). In total, 1,087 known microRNAs clustered with 689 pyknons across 279 of the 32,994 formed clusters.

The pyknons relate to recently discovered 3'UTR motifs. We compared the pyknons in $P_{3'UTR}$ to the 72 8-mer motifs that were recently reported to be conserved in human, mouse, rat and dog 3'UTRs (Xie, X., Lu, J., Kulbokas, E. J., Golub, T. R., Mootha, V., Lindblad-Toh, K., Lander, E. S. & Kellis, M. (2005) *Nature* 434, 338-45). We say that one of these 8-mers coincides with a pyknon of length l if one of the following conditions holds: the 8-mer agrees with letters 1-7 through l of a pyknon ('type 0' agreement); the 8-mer agrees with letters 1-8 through l-1 ('type 1' agreement); or, the 8-mer agrees with letters 1-9 through l-2 ('type 2' agreement). Of the 72 reported conserved 8-mers, 39 were in 'type 0' agreement, 10 in 'type 1' agreement, and seven in 'type 2' agreement with one or more pyknons from $P_{3'UTR}$. Six of the 8-mers did not match at all any of the pyknons in $P_{3'UTR}$. In summary, the pyknons that we have derived by intragenomic analysis overlap with 56 out of the 72 motifs that were discovered through cross-species comparisons.

Human pyknons are also present in other genomes where they associate with similar biological processes. In FIG. 19, and for each of 7 genomes in turn, we show how many positions in region X of the genome at hand are covered by the human pyknons contained in set $P_X$, X={5'UTR,CODING,3'UTR}. We account for length differences across genomes by reporting the number of covered positions per 10,000 nucleotides. FIG. 20 shows how many of the human pyknons contained in set $P_X$ can also be found in the region X of the genome under consideration, X={5'UTR,CODING,3'UTR}. FIG. 20 also shows the total number of intergenic and intronic positions covered by those of the human pyknons that are also in other genomes. Notably, the human genome contains more than 600 million nucleotides that are associated with identical copies of pyknons and are absent from the mouse and rat genomes. Interestingly, the human pyknons have many instances in the intergenic and intronic regions of the phylogenetically distant worm and fruit-fly genomes covering about 1.6 million nucleotides in each.

A set of 6,160 human-genome-derived pyknons are simultaneously present in human 3'UTRs (5,752 genes) and mouse 3'UTRs (4,905 genes) whereas a second set of 388 pyknons are simultaneously present in human 3'UTRs (565 genes), mouse 3'UTRs (673 genes) and fruit-fly 3'UTRs (554 genes). Strikingly, we found these two sets of common pyknons to be significantly over-represented in the same biological processes in these other genomes (i.e. mouse and fruit-fly) as in the human genome, even though the pyknons were initially discovered by processing the human genome in isolation (data not shown). The common processes include regulation of transcription, cell communication, signal transduction etc. Finally, for each of the 388 pyknons in this second set, we manually analyzed about 130 nucleotide-long neighborhoods centered on the instances of each pyknon across the human, mouse and fruit-fly 3'UTRs and for a total of more than 4,000 such neighborhoods: notably, we did not find any instance of syntenic conservation across the three genomes.

Accordingly, as explained above, we explored the existence of sequence-based links between coding and non-coding regions of the human genome and identified 127,998 pyknons with a combined 226,874 non-overlapping instances in the 5'UTRs, CRs or 3'UTRs of 30,675 transcripts from 20,059 human genes. In transcripts that contained multiple pyknon instances, we found that the pyknons arrange themselves combinatorially forming mosaics. Statistical analysis revealed that the untranslated and/or coding regions of genes associated with specific biological processes are significantly enriched/depleted in pyknons.

We also found that the pyknon placement in 5'UTRs, CRs and 3'UTRs is strongly biased: the starting positions of consecutive pyknons show a clear preference for distances between 18 and 31 nucleotides. Importantly, we found an apparent lack of correlation between consecutive pyknon instances in these regions. The observed bias in the relative placement of the pyknons is conspicuously reminiscent of lengths that are associated with small RNA molecules that induce PTGS, suggesting the hypothesis that the pyknons' instances correspond to binding sites for microRNAs. Analysis of the regions immediately surrounding the intergenic and intronic instances of the reverse complement of the 127,998 discovered pyknons revealed that 30.0% of the pyknons have instances within about 380,000 distinct, non-overlapping regions between 60 and 80 nucleotides in length that are predicted to fold into hairpin-shaped RNA secondary structures with folding energies $\leq$−30 Kcal/mol. Many of these predicted hairpin-shaped structures are located inside known introns and thus will be transcribed. Our analysis also suggests that PTGS may be effected though the genes' 5'UTR and amino acid regions, in addition to their 3'UTRs. Another resulting hypothesis is that RNAi products in animals likely fall into distinct categories that are quantized in terms of size and have preferences for lengths of 18, 22, 24, 26, 29, 30 and 31 nucleotides. Notably, through sequence-based analysis, we showed that about 40% of the known microRNAs are similar to 689 pyknons, and that the pyknons subsume 56 of the 72 recently reported 3'UTR motifs, lending further support to the possibility of a connection between the pyknons and RNAi/PTGS.

The intergenic/intronic copies of the 127,998 pyknons constrain approximately 900 million nucleotides of the human genome. Instances of human pyknons can also be found in other genomes namely *C. elegans, D. melanogaster, G. gallus, M. musculus, R. norvegicus* and *C. familiaris*. The number of human pyknons that can be located in the 5'UTRs, CRs and 3'UTRs of other genomes decreases with phylogenetic distance. Strikingly, the pyknons that we found inside mouse and fruit-fly 3'UTRs were over-represented in the same biological processes as in the human genome. On a related note, more than 600 million bases, which correspond to identically conserved intergenic and intronic copies of human pyknons, are not present in the mouse and rat genomes.

The fact that some of the intergenic/intronic copies of pyknons originate in repeat elements may lead one to assume that our analysis has merely 'rediscovered' such elements. However, as mentioned above, more than 50,000 of the pyknons have many of their instances in repeat-free regions. Moreover, the typical length of a pyknon is substantially smaller than, e.g., that of an ALU. It was recently reported that genes can achieve evolutionary novelty through the 'careful' incorporation of ALUs in their coding regions (Twashita, S., Osada, N., Itoh, T., Sezaki, M., Oshima, K., Hashimoto, E., Kitagawa-Arita, Y., Takahashi, I., Masui, T., Hashimoto, K. & Makalowski, W. (2003) *Mol Biol Evol* 20, 1556-63; and Lev-Maor, G., Sorek, R., Shomron, N. & Ast, G. (2003) *Science* 300, 1288-91). Also, the "pack-mule" paradigm revealed that entire genes, large fragments from a single gene, or fragments from multiple genes can be 'hijacked' by transposable elements (Jiang, N., Bao, Z., Zhang, X., Eddy, S. R. & Wessler, S. R. (2004) *Nature* 431, 569-73). However, 'fortuitous coincidence' is generally considered the prevailing mechanism by which such potential is unleashed. Contrasting this, the combinatorial arrangement of the pyknons within the untranslated and coding regions of genes together with the large number of instances in these regions and the association of pyknons with specific biological processes suggests that their placement is not accidental and likely serves a specific purpose. Our findings do not rule out a link with transposable elements. On the contrary, the findings seem to support a dynamic view of a genome (Jorgensen, R. A. (2004) *Cold Spring Harb Symp Quant Biol* 69, 349-54) that has learned to respond, and likely continues to respond, to environmental challenges or "stress" in a controlled, organized manner.

Taken together, the results suggest the existence of an extensive link between the non-coding and gene-coding parts in animal genomes. It is conceivable that this link could be the result of integration into the genome of dsRNA-breakdown products. Since many genes are known to give rise to antisense transcripts, it is possible that these genes were at some point subjected to RNAi-mediated dsRNA breakdown which in turn gave rise to products about 20 nucleotides in length. The latter, through repeated integration, could have eventually given rise to the numerous intergenic and intronic copies of the pyknons that we have identified. However, this explanation would have to be reconciled with four of our findings. First, the pyknons have identically conserved copies in non-genic regions. Second, pyknons appear to favor a specific size and, in genic regions, a specific relative placement. Third, slight modification of the 3'UTR instances of the pyknons by either prepending or appending immediately neighboring positions results in new strings whose intergenic and intronic copies are markedly decreased. And fourth, we can discover human pyknons in other organisms such as the mouse and the fruit-fly where they exhibit a persistent enrichment within specific processes yet are not the result of syntenic conservation. It may well be that we are seeing traces of an organized, coordinated activity that involves nearly all known genes. The existence of a pyknon-based regulatory layer that is massive in scope and extent, originates in the non-coding part of the genome, operates through the genes' untranslated and coding regions, and, is likely linked to PTGS, is a tantalizing possibility. Moreover, the observed disparity in the number of intergenic/intronic positions covered by human pyknons in the human and the phylogenetically-close mouse/rat genomes suggests that pyknons and thus the presumed regulatory layer may be organism-specific to some degree ("pyknome"). Addressing such questions might eventually help explain the apparent lack of correlation between the number of amino-acid coding genes in an organism and the organism's apparent complexity.

In the above description, and in order to identify motifs that are present in both non-genic and genic regions, we proceeded by first carrying out pattern discovery in the intergenic and intronic regions of the human genome. Once those patterns were determined, we identified additional instances for them in the genic regions of the genome and in particular in the 5' untranslated, amino acid coding and 3' untranslated regions of the genes. In other words, the computational analysis flowed from the non-genic to the genic-regions. But there is nothing that inherently prevents us from carrying out the computation in the other direction, i.e., from the genic to the non-genic regions, although there is potential for a loss in sensitivity that might result in the identification of smaller sets of motifs linking non-genic with genic regions. One could carry out the genic/non-genic analysis in a number of ways. For example, one could use a pattern discovery method to process the full collection of 5' untranslated, amino acid coding and 3' untranslated regions (with the regions processed separately or together), identifying recurrent motifs contained therein, and finally establishing links with the non-genic regions of the genome by locating the intergenic and intronic copies for these motifs.

Instead of working with the full length sequences of the genes' untranslated and coding regions, an alternative method would be to delineate areas of interest in these regions (effectively subselecting), analyzing those areas to derive motifs, and finally locating additional instances of these motifs in the non-genic parts of the genome. Such areas of interest could, for example, be known or putative microRNA binding sites. Alternatively, the areas of interest could be what, in our work on the problem of RNA interference, we refer to as "target islands." A detailed description of the work is described in the U.S. patent application identified as Ser. No. 11/351,821, filed on Feb. 10, 2006, and entitled "System and Method for Identification of MicroRNA Target Sites and Corresponding Targeting MicroRNA Sequences," the disclosure of which is incorporated herein.

Summarily, our approach for finding microRNA target sites is known as rna22 and proceeds as follows: it discovers statistically significant patterns that are contained in the sequences of known microRNAs, generates their reverse complement, identifies all the instances of these reverse-complement patterns in a region of interest (namely one of 5'UTRs, CRs or 3'UTRs) and finally reports groups of consecutive locations from the region of interest as long as they are 'hit' a minimum number of times by these patterns. Generally, the groups of consecutive locations that rna22 reports will be variable in length and may correspond to one or more binding sites: consequently, and so as to not loose generality, we have been referring to them as "target islands."

Let us assume that target islands are available for the region of interest. One could proceed by doing an all-against-all comparison of the target islands forming clusters. Any two target-islands that end up in the same cluster have the property that their corresponding sequences share a substantial portion of their extent, say a minimum of N locations. Initially, each target island is in its own cluster. There is always the possibility that the thresholds used in the various stages of the process are too stringent, thus resulting in the method to miss some target-islands that could have otherwise become members of some cluster c. In order to account for this, one could enhance the cluster-forming process as follows. Using the Clustal-W multiple alignment algorithm (Chenna, R., Sugawara, H., Koike, T., Lopez, R., Gibson, T. J., Higgins, D. G. & Thompson, J. D. (2003) *Nucleic Acids Res* 31, 3497-500), we could align the sequences in cluster c and extract the core region of the alignment, then use it to search the sequences of interest for instances of the core region that were skipped because of the employed thresholds. If a given cluster contains more than one core regions then it can be replaced by as many new clusters as the number of its distinct core regions. For each one of the formed clusters whose core region that resulted from the Clustal-W alignment of its members is at least N nucleotides in length, we report the region as a (genic) motif.

Optionally, one can discard core regions that exhibit low-complexity using the NSEG algorithm (Wootton, J. C. & Federhen, S. (1993) *Computers in Chemistry* 17, 149-163). These motifs are then sought in the corresponding genome's intergenic/intronic regions instances to establish links between coding and non-coding parts of the genome. Finally, it is clear that instead of clustering the target islands to determine motifs, one could simply use a pattern discovery approach and subselect among the reported patterns to keep only those that, for example, satisfy a minimum length requirement, or some other property.

Given the above description, a few points should be noted. First, it is clear that the method which we have described and the ensuing analysis is not specific to the human genome; in fact, it can be carried out separately in other eukaryotic genomes such as chimpanzee, mouse, rat, dog, chicken, fruit-fly, worm, etc. It is expected that the resulting pyknomes will have non-zero intersections with one another but will likely also contain organism-specific pyknons. Whether generated from the human or some other genome, the pyknons are statistically significant and link the non-genic and genic regions of the genome at hand. The links that are instantiated by the pyknons are 'natural' in that they involve large numbers of sequences that occur naturally in the genome at hand. Consequently, the pyknons would form natural candidates for a number of processes that to date have been carried out using schemes that make use of local information alone and do not take into account long-range conservations of the kind that we presented in our discussion.

Figure 21:
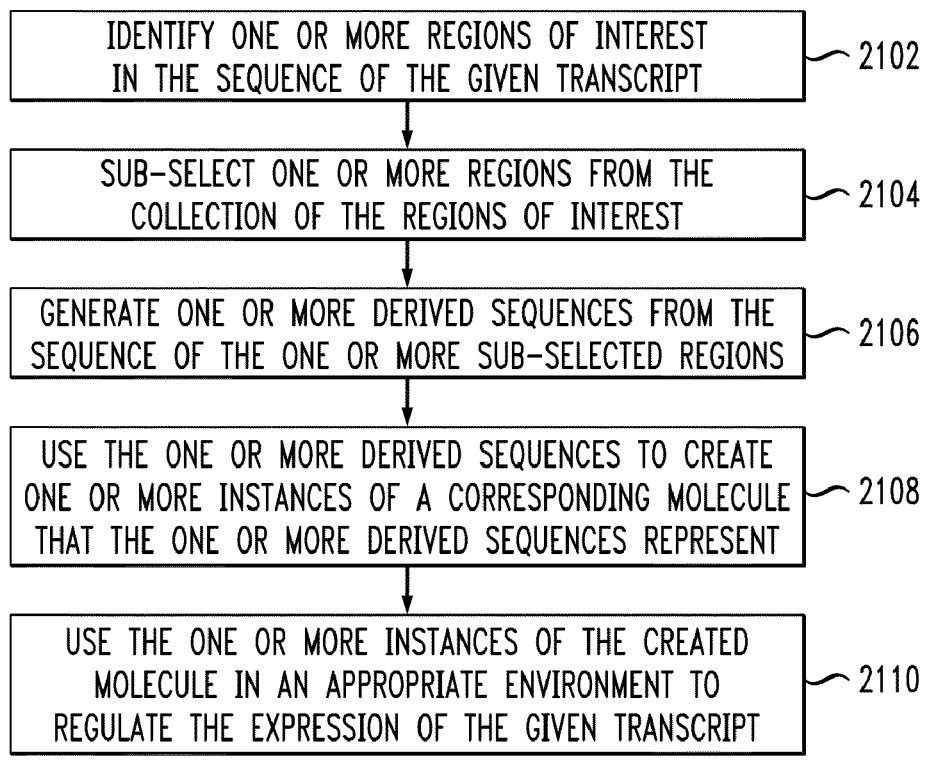
FIG. 21 is a diagram illustrating a first methodology for using pyknons, according to an embodiment of the present invention.

One such application would be the design of small interfering RNAs (siRNAs) to regulate the gene expression of one specific gene. Some of our pyknons have the property of being shared by two or more genes which allows the design of siRNAs that can interfere with a cluster of genes at once. As illustrated in the flow diagram of FIG. 21, a method for designing one or more sequences of siRNAs that can interact with one or more sites in a given transcript of a given sequence in a given organism and result in the down-regulation of the expression of the protein product encoded by the given transcript can comprise the following steps. One or regions of interest are identified in the sequence of a given transcript (step 2102). One or more regions are sub-selected from the collection of these regions (step 2104). One or more derived sequences are generated from the sequence of the one or more sub-selected regions (step 2106). The one or more derived sequences are used to create one more instances of the corresponding molecule that the one or more derived sequences represent (step 2108). The one or more instances of the created molecule are used in an appropriate environment to regulate the expression of the given transcript (step 2110).

Further, the method of designing one or more siRNAs may use a region of interest in the collection of regions of interest identified to be an instance of a motif that has one or more copies in the intergenic and intronic regions of the genome of interest, and one or more copies in the untranslated and amino acid coding regions of one or more genes in the genome of interest, each such region of interest being computed using the method and system for finding pyknons described above.

The method may use a region of interest in the collection of regions of interest identified using a method that is based on pattern discovery, for example, the method described in the above-referenced U.S. patent application identified as Ser. No. 11/351,821. A region of interest in the collection of regions of interest can also be identified to be a target island that is computed using the method also described in the above-referenced U.S. patent application identified as Ser. No. 11/351,821.

The method of designing one or more siRNAs may also use a region of interest, for example, located in the 5' untranslated region of the given transcript, located in the amino acid coding region of the given transcript, or located in the 3' untranslated region of the given transcript.

As detailed above, the method of designing one or more siRNAs can be used where the genome of interest is a eukaryotic genome, and wherein the eukaryotic genome is, for example, is the human genome, the mouse genome, the rat genome, the dog genome, the fruit fly genome, or the worm genome.

Also, the method of designing one or more siRNAs may use a region of interest that is sub-selected based on one or more of its attributes. These attributes may include, for example, the region's length and the region's location in the transcript.

The method of designing one or more siRNAs can also use a derived sequence that is, for example, the reverse complement of the sequence of the one or more sub-selected regions, or a near-reverse complement of the sequence of the one or more sub-selected regions, i.e. it contains mismatches at one or more locations.

The method of designing one or more siRNAs can be used such that the one or more copies of the molecule can be built using any of a set of biochemical processes.

Another application would involve the rational use of pyknons to appropriately engineer a transcript of interest in order to control its expression (either up-regulate or down-regulate) in a specific tissue or for a specific cellular process. For example, one could remove one or more of the pyknons existing in the transcript of interest leading to an up-regulation of the transcript. Alternatively, one could down-regulate the transcript of interest by adding more instances of existing pyknons and rely on the naturally occurring agent that targets this pyknon to induce down-regulation. Or one could add the sequence of a pyknon that is not among those contained in the transcript and selective control the transcript's expression by adding or removing appropriately generated instances of the reverse complement of the pyknon.

Figure 22:
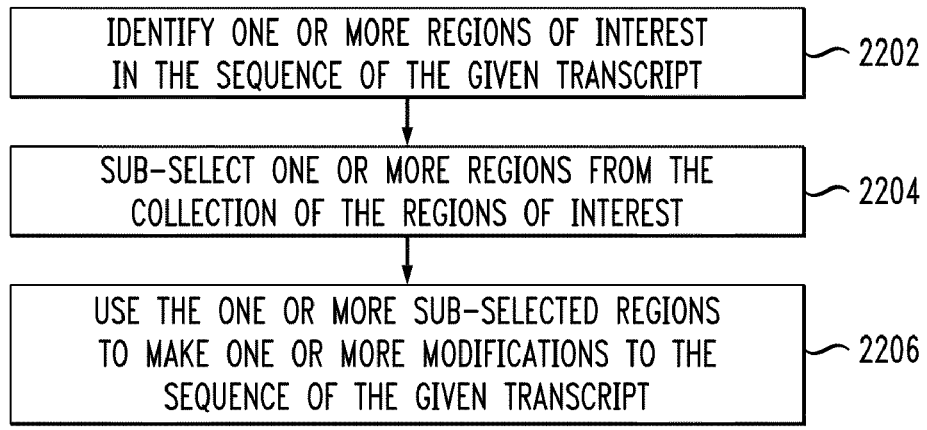
FIG. 22 is a diagram illustrating a second methodology for using pyknons, according to an embodiment of the present invention.

As illustrated in the flow diagram of FIG. 22, a method for engineering a given transcript of a given gene in a given organism in order to regulate its expression may comprise the following steps. One or more regions of interest are identified in the sequence of a given transcript (step 2202). One or more regions are sub-selected from the collection of these regions (step 2204). The one or more sub-selected regions are used to make one or more modifications to the sequence of the given transcript (step 2206).

Further, the method of engineering a given transcript to regulate gene expression can comprise many of the same steps as mentioned above in the method for designing one or more siRNAs. For example, the method of engineering a given transcript to regulate gene expression may use a region of interest in the collection of regions of interest identified to be an instance of a motif that has one or more copies in the intergenic and intronic regions of the genome of interest, and one or more copies in the untranslated and amino acid coding regions of one or more genes in the genome of interest. The motif can be computed, for example, using the pyknons discovery method and system described above.

Also, as above, the method of engineering a given transcript to regulate gene expression may use a region of interest in the collection of regions of interest computed using a method that is based on pattern discovery, for example, the method described in the above-referenced U.S. patent application identified as Ser. No. 11/351,821.

The present method may also use a region of interest, for example, located in the 5' untranslated region of the given transcript, located in the amino acid coding region of the given transcript, or located in the 3' untranslated region of the given transcript.

Also, similar to the above methodology, the method of engineering a given transcript to regulate gene expression may use a region of interest that is sub-selected based on one or more of its attributes including, for example, the region's length and the region's location in the transcript. Additional attributes may include the association of the region with a given biological process, the region's association with a given tissue, and the region's association with a given cellular compartment.

Further, the method of engineering a given transcript to regulate gene expression can include a modification that, for example, comprises an extension of the sequence of the given transcript, or a shortening of the sequence of the given transcript. The extension can, for example, comprise one or more instances of a region of interest, and the shortening can, for example, comprise one or more instances of a region of interest.

Another application of pyknons, for example, would be the measuring of the impact that one or more pyknons can have on a gene's regulation "by proxy." This would entail the engineering of an assay that involves a reporter gene (for example, luciferase) and instances of the one or more pyknons placed downstream from the region that codes for the reporter's amino acid sequence. Then, one can measure the impact on the expression of the reporter gene by using various combinations of appropriately generated instances of the reverse complement of these pyknons. The observations made in the context of the reporter assay can then be carried over to the gene that is studied. Additional applications are also possible if one assumes that for the organism that is being studied the sequences of the corresponding pyknons are available.

Figure 23:
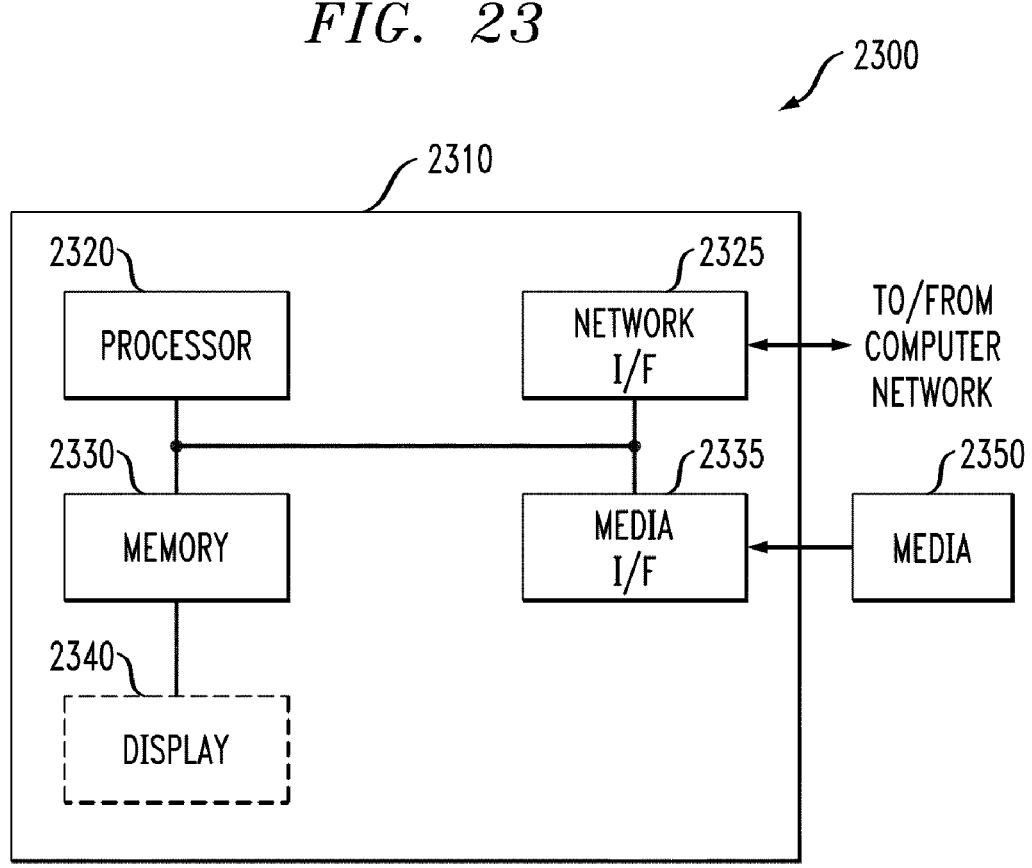
FIG. 23 is a block diagram of an exemplary hardware implementation of one or more of the methodologies of the present invention, according to an embodiment of the present invention.

FIG. 23 is a block diagram of an exemplary hardware implementation of one or more of the methodologies of the present invention. That is, apparatus 2300 may implement one or more of the steps/components described above in the context of FIGS. 1-22. Apparatus 2300 comprises a computer system 2310 that interacts with media 2350. Computer system 2310 comprises a processor 2320, a network interface 2325, a memory 2330, a media interface 2335 and an optional display 2340. Network interface 2325 allows computer system 2310 to connect to a network, while media interface 2335 allows computer system 2310 to interact with media 2350, such as a Digital Versatile Disk (DVD) or a hard drive.

As is known in the art, the methods and apparatus discussed herein may be distributed as an article of manufacture that itself comprises a computer-readable medium having computer-readable code means embodied thereon. The computer-readable program code means is operable, in conjunction with a computer system such as computer system 2310, to carry out all or some of the steps to perform one or more of the methods or create the apparatus discussed herein. For example, the computer-readable code is configured to implement a method of determining associations between non-coding sequences and gene coding sequences in a genome of an organism, by the steps of identifying at least one conserved region from a plurality of the non-coding sequences; and linking the at least one conserved region with one or more of the gene coding sequences of the genome to associate the at least one conserved region with one or more biological processes of the organism. The computer-readable medium may be a recordable medium (e.g., floppy disks, hard drive, optical disks such as a DVD, or memory cards) or may be a transmission medium (e.g., a network comprising fiber-optics, the world-wide web, cables, or a wireless channel using time-division multiple access, code-division multiple access, or other radio-frequency channel). Any medium known or developed that can store information suitable for use with a computer system may be used. The computer-readable code means is any mechanism for allowing a computer to read instructions and data, such as magnetic variations on a magnetic medium or height variations on the surface of a compact disk.

Memory 2330 configures the processor 2320 to implement the methods, steps, and functions disclosed herein. The memory 2330 could be distributed or local and the processor 2320 could be distributed or singular. The memory 2330 could be implemented as an electrical, magnetic or optical memory, or any combination of these or other types of storage devices. Moreover, the term "memory" should be construed broadly enough to encompass any information able to be read from or written to an address in the addressable space accessed by processor 2320. With this definition, information on a network, accessible through network interface 2325, is still within memory 2330 because the processor 2320 can retrieve the information from the network. It should be noted that each distributed processor that makes up processor 2320 generally contains its own addressable memory space. It should also be noted that some or all of computer system 2310 can be incorporated into an application-specific or general-use integrated circuit.

Optional video display 2340 is any type of video display suitable for interacting with a human user of apparatus 2300. Generally, video display 2440 is a computer monitor or other similar video display.

Although illustrative embodiments of the present invention have been described herein with reference to the accompanying drawings, it is to be understood that the invention is not limited to those precise embodiments, and that various other changes and modifications may be made by one skilled in the art without departing from the scope or spirit of the invention.

What is claimed is:

1. A method of engineering a given transcript of a given gene in a given organism in order to regulate expression of the given transcript, wherein the method is run on a system comprising one or more distinct components, each of the one or more distinct components being embodied on a tangible computer-readable recordable storage medium, the method comprising:

identifying one or more regions of interest in a sequence of the given transcript, wherein identifying one or more regions of interest in a sequence of the given transcript is carried out by a component executing on a hardware processor;

sub-selecting, within the one or more identified regions of interest, a motif, wherein sub-selecting a motif comprises identifying one or more identically conserved copies of the motif in intergenic and intronic regions of the genome of interest and identifying one or more additional copies in untranslated and amino acid coding regions of one or more genes in the genome of interest, wherein sub-selecting a motif further comprises using a pattern discovery technique with a pre-determined parameter of minimum size of discovered pattern and a pre-determined parameter of minimum required number of discovered copies before a pattern can be deemed as identified, and further wherein sub-selecting a motif is carried out by a component executing on a hardware processor; and using the one or more sub-selected regions to make one or more modifications to the sequence of the given transcript, wherein using the one or more sub-selected regions to make one or more modifications to the sequence of the given transcript is carried out by a component executing on a hardware processor.

2. The method of claim 1, where the motif is computed using a process wherein associations are determined between non-coding sequences and gene coding sequences in a genome of an organism, the process comprising the steps of:

identifying at least one conserved region from a plurality of the non-coding sequences;

linking the at least one conserved region with one or more of the gene coding sequences of the genome; and associating the at least one conserved region with one or more biological processes of the organism.

3. The method of claim 1, wherein a region of interest in the collection of regions of interest is computed using a pattern discovery technique.

4. The method of claim 1, wherein a region of interest is located in a 5' untranslated region of the given transcript.

5. The method of claim 1, wherein a region of interest is located in an amino acid coding region of the given transcript.

6. The method of claim 1, wherein a region of interest is located in a 3' untranslated region of the given transcript.

7. The method of claim 1, wherein a region of interest is sub-selected based on one or more of its attributes.

8. The method of claim 7, wherein an attribute is length of the region.

9. The method of claim 7, wherein an attribute is location of the region in the transcript.

10. The method of claim 7, wherein an attribute is association of the region with a given biological process.

11. The method of claim 7, wherein an attribute is association of the region with a given tissue.

12. The method of claim 7, wherein an attribute is association of the region with a given cellular compartment.

13. The method of claim 1, wherein a modification comprises an extension of the sequence of the given transcript.

14. The method of claim 13, wherein the extension comprises one or more instances of a region of interest.

15. The method of claim 1, wherein a modification comprises a shortening of the sequence of the given transcript.

16. The method of claim 15, wherein the shortening comprises one or more instances of a region of interest.

* * * * *